(12) United States Patent
Allan et al.

(10) Patent No.: US 8,519,134 B2
(45) Date of Patent: Aug. 27, 2013

(54) ARYL-PYRIDINE DERIVATIVES AS ALDOSTERONE SYNTHASE INHIBITORS

(75) Inventors: Martin Allan, Cambridge, MA (US); Sylvie Chamoin, Saint Louis (FR); Qi-Ying Hu, Needham, MA (US); Hidetomo Imase, Somerville, MA (US); Julien Papillon, Somerville, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/509,646

(22) PCT Filed: Nov. 16, 2010

(86) PCT No.: PCT/EP2010/067536
§ 371 (c)(1),
(2), (4) Date: May 14, 2012

(87) PCT Pub. No.: WO2011/061168
PCT Pub. Date: May 26, 2011

(65) Prior Publication Data
US 2012/0316195 A1    Dec. 13, 2012

Related U.S. Application Data

(60) Provisional application No. 61/261,948, filed on Nov. 17, 2009.

(51) Int. Cl.
*C07D 221/02* (2006.01)
*A61K 31/44* (2006.01)

(52) U.S. Cl.
USPC .......................................... 546/112; 514/299

(58) Field of Classification Search
USPC ........................................ 546/112; 514/299
See application file for complete search history.

(56) References Cited

U.S. PATENT DOCUMENTS

| | | | |
|---|---|---|---|
| 4,018,777 | A | 4/1977 | Zaugg et al. |
| 6,225,316 | B1 | 5/2001 | Bos et al. |
| 8,030,334 | B2 | 10/2011 | Adams et al. |
| 2010/0261698 | A1 | 10/2010 | Adams et al. |
| 2010/0292225 | A1 | 11/2010 | Chamoin et al. |
| 2011/0082129 | A1 | 4/2011 | Adams et al. |
| 2012/0071512 | A1 | 3/2012 | Adams et al. |
| 2012/0071514 | A1 | 3/2012 | Hu et al. |

FOREIGN PATENT DOCUMENTS

| | | |
|---|---|---|
| EP | 2218464 A1 | 8/2010 |
| JP | 2000327659 | 11/2000 |
| WO | 0050401 A1 | 8/2000 |
| WO | 02094823 A1 | 11/2002 |
| WO | 04000814 A1 | 12/2003 |
| WO | 2009/017822 A2 | 2/2009 |
| WO | 2009062676 A2 | 5/2009 |
| WO | 2009077367 A1 | 6/2009 |
| WO | 2009100130 A1 | 8/2009 |
| WO | 2009103652 A1 | 8/2009 |
| WO | 2009/156462 A2 | 12/2009 |
| WO | 2010023317 A1 | 3/2010 |
| WO | 2010055128 A1 | 5/2010 |
| WO | 2010057833 A1 | 5/2010 |
| WO | 2010/117090 A1 | 10/2010 |

OTHER PUBLICATIONS

Campbell et al., Bioorganic & Medicinal Chemistry Letters, 1(12):695-698 (1991).
Heim et al., J. Med. Chem., 51(16):5064-5074 (2008).
Voets et al., "Heteroaryl Substituted Naphthalenes and Structurally Modified Derivatives: Selective Inhibitors of CYP11B2 for the Treatment of Congestive Heart Failure and Myocarial Fibrosis," Journal of Medicinal Chemistry 48 (21):6632-6642 (Nov. 1, 2005).
Buerik et al., "The Human Steroid Hydroxylases CYP11B1 and CYP11B2," Biological Chemistry 383(1):1537-1551 (Oct. 1, 2002).
Ulmschneider et al., "Development and evaluation of a pharmacophoric model for inhibitors of aldosterone synthase (CYP11B2)," Bioorganic and Medicinal Chemistry Letters 16(1):25-30 (Jan. 1, 2005).

*Primary Examiner* — John Mabry
(74) *Attorney, Agent, or Firm* — Sophie Binet Cross

(57) ABSTRACT

The present invention provides a compound of formula (I) or a pharmaceutically acceptable salt thereof, wherein $R^1$, $R^2$, $R^3$, $R^4$, $R^5$ and n are defined herein. The invention also relates to a method for manufacturing compounds of the invention, and their therapeutic uses. The present invention further provides a combination of pharmacologically active agents and a pharmaceutical composition.

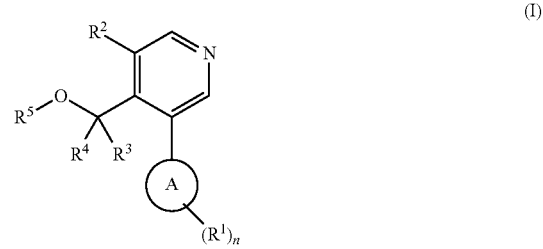

(I)

13 Claims, No Drawings

ARYL-PYRIDINE DERIVATIVES AS ALDOSTERONE SYNTHASE INHIBITORS

This application is a US National Phase filing of International Application No. PCT/EP2010/067536 filed Nov. 16, 2010, and claims priority to U.S. Application Ser. No. 61/261,948 filed Nov. 17, 2009, the contents of which are incorporated herein by reference in their entirety.

BACKGROUND OF THE INVENTION

The mineralocorticoid hormone aldosterone is produced by the adrenal gland and acts on the distal tubules and collecting ducts of the kidney to increase reabsorption of ions and water in the kidney. Aldosterone causes conservation of sodium, secretion of potassium, increased water retention, and increased blood pressure.

Aldosterone has been implicated in the pathogenesis of cardiovascular diseases such as hypertension and heart failure. In clinical trials, treatment with the nonselective mineralocorticoid receptor antagonist (MRA) spironolactone or the selective MRA eplerenone significantly reduced morbidity and mortality among patients with heart failure or myocardial infarction already taking an angiotensin-converting enzyme inhibitor or a β-blocker. However, significant side effects such as gynecomastia and impotence were observed in male patients receiving spironolactone while hyperkalemia was seen in patients taking either drug.

SUMMARY OF THE INVENTION

The invention pertains to the compounds, methods for using them, and uses thereof as described herein. Examples of compounds of the invention include the compounds according to any of Formulae I to V, or a pharmaceutically acceptable salt thereof, and the compounds of the examples.

The invention therefore provides a compound of the Formula I:

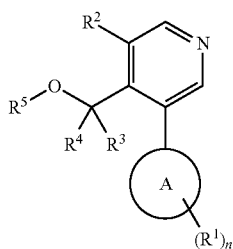

I wherein:
A is phenyl, naphthyl or a heteroaryl selected from the group consisting of benzimidazolyl, azaindolyl, quinolinyl, benzothienyl, benzoxazolyl, thienyl, benzothiazolyl and benzofuranyl;
$R^1$ for each occurrence, is independently halogen, $C_{1-6}$-alkyl, $C_{3-7}$-cycloalkyl, $C_{1-6}$-alkoxy, —S—$C_{1-6}$-alkyl, S—$C_{6-10}$-aryl, $C_{6-10}$-aryl, $C_{6-10}$-aryl-$C_{1-6}$-alkyloxy, heteroaryl, heterocyclyl, $C_{6-10}$-aryloxy, heteroaryloxy, heterocycyloxy, cyano, $NR^aR^b$, nitro, C(O)—$C_{1-6}$-alkyl, C(O)O—$C_{1-6}$-alkyl, C(O)O—$C_{6-10}$aryl, C(O)O-heteroaryl, C(O)$NR^aR^b$, $NR^aC(O)$—$C_{1-6}$-alkyl, $NR^aC(O)$—$C_{6-10}$-aryl, $NR^aC(O)$-heteroaryl, $NR^a$-heterocyclyl, carboxy, sulfonyl, sulfamoyl or sulfonamido, in which each alkyl, alkoxy, aryl, heteroaryl and heterocyclyl are optionally substituted with one or more groups selected from the group consisting of halo, $C_{1-6}$-alkyl, $C_{1-6}$-alkoxy, hydroxy, halo-$C_{1-6}$-alkyl, $C_{6-10}$-aryl, heteroaryl, $C_{6-10}$-aryloxy and $C_{3-7}$cycloalkyl; or two adjacent $R^1$ form together with the atoms to which they are attached a 5- or 6-membered saturated heterocyclyl; with the proviso that two adjacent $R^1$ do not form together with A ring an indolinone, a benzoxazolone, a benzimidazolone or a benzothiazolone;
$R^a$ and $R^b$ for each occurrence, are independently H, $C_{1-6}$-alkyl, $C_{3-7}$-cycloalkyl, $C_{6-10}$-aryl, heterocyclyl, heteroaryl or $R^a$ and $R^b$ which are attached to the same nitrogen may form together with the nitrogen to which they are attached a 5- to 7-membered saturated heterocyclyl;
$R^2$ is H, $C_{1-6}$-alkyl, $C_{1-6}$-alkoxy, halo-$C_{1-6}$-alkyl, $C_{3-7}$-cycloalkyl, cyano or halogen;
$R^3$ and $R^4$ are independently H, $C_{1-6}$-alkyl or $C_{3-7}$cycloalkyl; wherein alkyl can be optionally substituted with $C_{1-6}$alkoxy, halogen, hydroxy, or $R^3$ and $R^4$ can form together with the atoms to which they are attached a 4- to 7-membered heterocyclyl or a 3- to 7-membered cycloalkyl; and when A is naphthyl or benzothiazole then one of $R^3$, $R^4$ is other than H;
$R^5$ is H or $C_{1-6}$-alkyl; or $R^5$ and $R^3$ or $R^5$ and $R^4$ form together with the atoms to which they are attached a 4- to 7-membered saturated heterocyclyl; or $R^5$ and $R^2$ form together with the atoms to which they are attached a 5- to 7-membered ring saturated heterocyclyl which may be optionally substituted with oxo;
n is 0, 1, 2, 3, 4 or 5;
with the proviso that compound of Formula I is not (3-o-tolylpyridin-4-yl)methanol, (3-methoxy-5-phenylpyridin-4-yl)methanol, (3-(2-fluorophenyl)-5-methoxypyridin-4-yl)methanol, (3-(4-fluorophenyl)-5-methoxypyridin-4-yl)methanol, (3-fluoro-5-(4-fluorophenyl)pyridin-4-yl)methanol, (3-(4-fluorophenyl)pyridin-4-yl)methanol, (3-fluoro-5-phenylpyridin-4-yl)methanol, (3-chloro-5-phenylpyridin-yl)methanol, (3-chloro-5-(2-fluorophenyl)pyridin-4-yl)methanol, (3-fluoro-5-(2-fluorophenyl)pyridin-4-yl)methanol, (3-(2-fluorophenyl)pyridin-4-yl)methanol, (3-phenylpyridin-4-yl)methanol, (3-chloro-5-(4-fluorophenyl)pyridin-4-yl)methanol, (3-chloro-5-(3-fluorophenyl)pyridin-4-yl)methanol, (3-fluoro-5-(3-fluorophenyl)pyridin-4-yl)methanol, (3-(3-fluorophenyl)-5-methoxypyridin-4-yl)methanol or (3-(3-fluorophenyl)pyridin-4-yl)methanol, or a pharmaceutically acceptable salt thereof.

In another embodiment, the invention pertains, to a method for treating a disorder or disease mediated by aldosterone synthase and/or 11-beta hydroxylase (CYP11B1) in a subject by administering to the subject a therapeutically effective amount of a compound according to anyone of Formulae I to V, or a pharmaceutically acceptable salt thereof, such that the disorder or disease mediated by aldosterone synthase and/or CYP11B1 in the subject is treated.

In yet another embodiment, the invention pertains to a method for treating a subject for hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive cortisol level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess, comprising administering to the subject a therapeutically effective amount of a compound according to anyone of Formulae I to V, or a pharmaceutically acceptable salt thereof, such that the subject is treated.

In yet another embodiment, the invention pertains to pharmaceutical compositions, comprising an effective amount of a compound according to anyone of Formulae I to V, or a pharmaceutically acceptable salt thereof, wherein said effective amount is effective to treat a disorder or disease mediated by aldosterone synthase and/or CYP11B1.

In still another embodiment, the invention pertains, at least in part, to combinations including pharmaceutical combinations of one or more therapeutically active agents.

In another embodiment, the invention pertains to a method for inhibiting aldosterone synthase and/or CYP11B1 in a subject by administering to the subject a therapeutically effective amount of a compound according to anyone of Formulae I to V, or a pharmaceutically acceptable salt thereof, such that aldosterone synthase and/or CYP11B1 is inhibited.

DETAILED DESCRIPTION OF THE INVENTION

Definition:

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 20 carbon atoms. Preferably the alkyl comprises 1 to 6 carbon atoms, and more preferably 1 to 4 carbon atoms. Representative examples of alkyl include methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl. The term "$C_{1-6}$alkyl" refers to a hydrocarbon having from one to six carbon atoms.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. The term "halo-$C_{1-6}$alkyl" refers to a hydrocarbon having from one to six carbon atoms and being substituted by one or more halo groups.

The term "alkenyl" refers to a branched or unbranched hydrocarbon having at least one carbon-carbon double bond. The term "$C_{2-6}$alkenyl" refers to a hydrocarbon having from two to six carbon atoms and comprising at least one carbon-carbon double bond. Representative examples of alkenyl are vinyl, prop-1-enyl, allyl, butenyl, isopropenyl or isobutenyl.

The term "alkynyl" refers to a branched or unbranched hydrocarbon having at least one carbon-carbon triple bond. The term "$C_{2-6}$alkynyl" refers to a hydrocarbon having from two to six carbon atoms and comprising at least one carbon-carbon triple bond. Representative examples of $C_{2-6}$alkynyl are ethynyl, prop-1-ynyl, butynyl, isopropynyl or isobutynyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1 to 6, more preferably about 1 to 4 carbons.

As used herein, the term "cycloalkyl" refers to saturated or partially unsaturated monocyclic, bicyclic or tricyclic hydrocarbon groups of 3-12 carbon atoms, preferably 3-8, or 3-7 carbon atoms. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2]octyl. Exemplary tricyclic hydrocarbon groups include adamantyl. The term "$C_{3-7}$ cycloakyl" refers to a cyclic hydrocarbon groups having 3 to 7 carbon atoms.

The term "aryl" refers to monocyclic or bicyclic aromatic hydrocarbon groups having 6-10 carbon atoms in the ring portion. The term "aryl" also refers to a group in which an aromatic ring is fused to one or more cycloalkyl rings or heterocyclyl rings, where the radical or point of attachment is on the aromatic ring or on the fused cycloalkyl or heterocyclyl ring. Representative examples of aryl are phenyl, naphthyl, indanyl or tetrahydronaphthyl, hexahydroindyl. The term "$C_{6-10}$ aryl" refers to an aromatic hydrocarbon groups having 6 to 10 carbon atoms in the ring portion.

The term "arylalkyl" is an alkyl substituted with aryl. Representative examples of arylalkyl are benzyl or Phenyl-CH$_2$CH$_2$—.

The term "aryloxy" includes an —O-aryl moiety, wherein aryl is defined herein.

The term "arylalkyloxy" refers to an —O-arylalkyl moiety, wherein arylalkyl is defined herein.

The term "Heteroaryl" includes aromatic monocyclic or bicyclic heteroaryl, containing from 5-10 ring members selected from carbon atoms and 1 to 5 heteroatoms, and each heteroatoms is independently selected from O, N or S, where O and S can be oxidized to various oxidation states. Typical monocyclic heteroaryl groups include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, or pyridyl-4-yl, pyridazin-3-yl, pyridazin-4-yl, pyrazin-3-yl, 2-pyrazin-2-yl, pyrazin-4-yl, pyrazin-5-yl, 2-, 4-, or 5-pyrimidin-2-yl, pyrimidin-4-yl and pyrimidin-5-yl. The term "heteroaryl" also refers to a group in which a heteroaromatic ring is fused to one or more aryl, cycloaliphatic, or heterocyclyl rings, where the radical or point of attachment is on the heteroaromatic ring or on the fused aryl, cycloaliphatic or heterocyclyl rings. Representative examples of bicyclic heteroaryl are indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl.

The term "heteroarylalkyl" refers to $C_{1-7}$ alkyl substituted with heteroaryl.

The term "heteroaryloxy" includes an —O-heteroaryl moiety, wherein heteroaryl is defined herein.

As used herein, the term "heterocyclyl" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. In one embodiment, heterocyclyl moiety represents a saturated monocyclic ring containing from 5-7 ring atoms and containing 1, 2 or 3 heteroatoms. The heterocyclyl group can be attached at a heteroatom or a carbon atom. The heterocyclyl can include fused or bridged rings as well as spirocyclic rings. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

The term heterocyclyloxy includes an —O-heterocyclyl, wherein heterocyclyl is defined herein.

The term "hydroxy" or "hydroxyl" includes groups with an —OH.

The term "halogen" includes fluorine, bromine, chlorine, iodine.

The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus. In one embodiment, "heteroatom" includes nitrogen, sulfur and oxygen.

The term "sulfonyl" includes R—SO$_2$—, wherein R is hydrogen, $C_{1-6}$ alkyl, $C_{2-6}$ alkenyl, $C_{2-6}$ alkynyl, $C_{6-10}$ aryl, heteroaryl, $C_{6-10}$ aryl $C_{1-6}$ alkyl, heteroaryl $C_{1-6}$ alkyl, $C_{1-7}$ alkoxy, $C_{6-10}$ aryloxy, heteroaryloxy, heterocyclyloxy, $C_{3-7}$ cycloalkyl, $C_{3-7}$cycloalkyl $C_{1-6}$ alkyl, heterocyclyl or heterocyclyl-$C_{1-6}$ alkyl. The term "sulfonyl" also includes both substituted and unsubstituted moieties which may be substituted with one or more $C_{1-4}$ alkyl, $C_{2-6}$ alkenyl, $C_{2-6}$ alkynyl, $C_{3-7}$ cycloalkyl, halogen, hydroxy or $C_{1-6}$ alkoxy groups.

The term "sulfonamido" includes $C_{1-6}$ alkyl-S(O)$_2$—NH—, $C_{2-6}$ alkenyl-S(O)$_2$—NH—, $C_{2-8}$ alkynyl-S(O)$_2$NH—, $C_{3-7}$cycloalkyl-S(O)$_2$NH—, $C_{6-10}$ aryl-S(O)$_2$—NH—, $C_{6-10}$ aryl $C_{1-6}$ alkyl-S(O)$_2$—NH—, heteroaryl-S(O)$_2$—NH—, heteroaryl $C_{1-6}$ alkyl-S(O)$_2$—NH—, heterocyclyl-S(O)$_2$—NH—, heterocyclyl-S(O)$_2$—NH—, $C_{1-6}$ alkyl-S(O)$_2$—N($C_{1-7}$ alkyl)-, $C_{2-6}$ alkenyl-S(O)$_2$—N($C_{1-7}$ alkyl)-, $C_{2-7}$ alkynyl-S(O)$_2$N($C_{1-7}$alkyl)-, $C_{3-7}$cycloalkyl-S(O)$_2$N($C_{1-6}$alkyl)-, $C_{6-10}$ aryl-S(O)$_2$—N($C_{1-6}$alkyl)-, $C_{6-10}$ aryl $C_{1-6}$alkyl-S(O)$_2$—N($C_{1-6}$alkyl)-, heteroaryl-S(O)$_2$—N($C_{1-6}$ alkyl)-, heteroaryl $C_{1-6}$ alkyl-S(O)$_2$—N($C_{1-6}$alkyl)-, heterocyclyl-S(O)$_2$—N($C_{1-6}$ alkyl)-, heterocyclyl-S(O)$_2$—N($C_{1-6}$ alkyl)-. The term "sulfamido" also include both substituted and unsubstituted moieties which may be substituted with one or more $C_{1-6}$alkyl, $C_{2-6}$alkenyl, $C_{2-6}$ alkynyl, $C_{3-7}$cycloalkyl, halogen, hydroxy or $C_{1-6}$ alkoxy groups.

The term "sulfamoyl" includes H$_2$NS(O)$_2$—, $C_{1-6}$ alkyl-NHS(O)$_2$—, ($C_{1-6}$alkyl)$_2$NS(O)$_2$—, $C_{6-10}$ aryl-NHS(O)$_2$—, $C_{1-6}$alkyl($C_{6-10}$ aryl)-NS(O)$_2$, ($C_{6-10}$ aryl)$_2$NS(O)$_2$, heteroaryl-NHS(O)$_2$—, ($C_{6-10}$ aryl $C_{1-6}$alkyl)-NHS(O)$_2$—, (heteroaryl $C_{1-6}$ alkyl)-NHS(O)$_2$—. The term includes both substituted and unsubstituted sulfamoyl moieties which may be substituted with one or more $C_{1-6}$alkyl, $C_{2-6}$alkenyl, $C_{2-6}$alkynyl, $C_{3-7}$cycloalkyl, halogen, hydroxy or $C_{1-6}$alkoxy groups.

The term "carboxy" refers to carboxylic acid.
Compound of the Invention:

Various embodiments of the invention are described herein. It will be recognized that features specified in each embodiment may be combined with other specified features to provide further embodiments.

In one embodiment, the invention pertains to compounds of Formula I or a pharmaceutically acceptable salt thereof, wherein:

A is phenyl, naphthyl or benzofuranyl;

$R^1$ for each occurrence, is independently halogen, $C_{1-6}$-alkyl, $C_{3-7}$cycloalkyl, $C_{1-6}$-alkoxy, S—$C_{1-6}$-alkyl, —S—$C_{6-10}$-aryl, $C_{6-10}$-aryl, $C_{6-10}$-aryl-$C_{1-6}$-alkyloxy, heteroaryl, heterocyclyl, $C_{6-10}$aryloxy, heteroaryloxy, heterocyclyloxy, cyano, NR$^a$R$^b$, nitro, C(O)—$C_{1-6}$-alkyl, C(O)O—$C_{1-6}$-alkyl, C(O)O—$C_{6-10}$aryl, C(O)O-heteroaryl, C(O)NR$^a$R$^b$, NR$^a$C(O)—$C_{1-6}$-alkyl, NR$^a$C(O)—$C_{6-10}$-aryl, NR$^a$C(O)-heteroaryl, NR$^a$-heterocyclyl, carboxy, sulfonyl, sulfamoyl or sulfonamido, in which each alkyl, alkoxy, aryl, heteroaryl and heterocyclyl are optionally substituted with halo, $C_{1-6}$-alkyl, $C_{1-6}$-alkoxy, hydroxy, halo-$C_{1-6}$-alkyl, $C_{6-10}$-aryl, heteroaryl, $C_{6-10}$-aryloxy or $C_{3-7}$cycloalkyl;

$R^a$ and $R^b$ for each occurrence, are independently H, $C_{1-6}$-alkyl, $C_{3-7}$-cycloalkyl, $C_{6-10}$-aryl, heterocyclyl, heteroaryl or $R^a$ and $R^b$ which are attached to the same nitrogen, may form together with the nitrogen to which they are attached a 5- to 7-membered saturated heterocyclyl;

$R^2$ is H, $C_{1-6}$-alkyl, $C_{1-6}$-alkoxy, halo-$C_{1-6}$-alkyl, $C_{3-7}$-cycloalkyl, cyano or halogen;

$R^3$ and $R^4$ are independently H, $C_{1-6}$-alkyl or $C_{3-2}$cycloalkyl; wherein alkyl can be optionally substituted with $C_{1-6}$alkoxy, halogen, hydroxy, or $R^3$ and $R^4$ can form together with the atoms to which they are attached a 4- to 7-membered heterocyclyl or a 3- to 7-membered cycloalkyl; and when A is naphthyl then one of $R^3$, $R^4$ is other than H;

$R^5$ is H or $C_{1-6}$-alkyl; or $R^5$ and $R^3$ form together with the atoms to which they are attached a 4- to 7-membered saturated heterocyclyl; or $R^5$ and $R^2$ form together with the atoms to which they are attached a 5- to 7-membered ring saturated heterocyclyl which may be optionally substituted with oxo;

n is 0, 1, 2, 3, 4 or 5;

with the proviso that compound of Formula I is not (3-o-tolylpyridin-4-yl)methanol, (3-methoxy-5-phenylpyridin-4-yl)methanol, (3-(2-fluorophenyl)-5-methoxypyridin-4-yl)methanol, (3-(4-fluorophenyl)-5-methoxypyridin-4-yl)methanol, (3-fluoro-5-(4-fluorophenyl)pyridin-4-yl)methanol, (3-(4-fluorophenyl)pyridin-4-yl)methanol, (3-fluoro-5-phenylpyridin-4-yl)methanol, (3-chloro-5-phenylpyridin-yl)methanol, (3-chloro-5-(2-fluorophenyl)pyridin-4-yl)methanol, (3-fluoro-5-(2-fluorophenyl)pyridin-4-yl)methanol, (3-(2-fluorophenyl)pyridin-4-yl)methanol, (3-phenylpyridin-4-yl)methanol, (3-chloro-5-(4-fluorophenyl)pyridin-4-yl)methanol, (3-chloro-5-(3-fluorophenyl)pyridin-4-yl)methanol, (3-fluoro-5-(3-fluorophenyl)pyridin-4-yl)methanol, (3-(3-fluorophenyl)-5-methoxypyridin-4-yl)methanol or (3-(3-fluorophenyl)pyridin-4-yl)methanol.

In another embodiment, the invention pertains to compounds of Formula I or a pharmaceutically acceptable salt thereof, wherein:

A is phenyl, naphthyl or benzofuranyl;

$R^1$ for each occurrence, is independently halogen, $C_{1-6}$-alkyl, $C_{3-7}$-cycloalkyl, $C_{1-6}$-alkoxy, S—$C_{1-6}$-alkyl, —S—$C_{6-10}$-aryl, $C_{6-10}$-aryl-$C_{1-6}$-alkyloxy, heteroaryl, heterocyclyl, $C_{6-10}$aryloxy, heteroaryloxy, heterocyclyloxy, cyano, $NR^aR^b$, nitro, C(O)—$C_{1-6}$-alkyl, C(O)O—$C_{1-6}$-alkyl, C(O)O—$C_{6-10}$ aryl, C(O)O-heteroaryl, C(O)$NR^aR^b$, $NR^aC(O)$—$C_{1-6}$-alkyl, $NR^aC(O)$—$C_{6-10}$-aryl, $NR^aC(O)$-heteroaryl, $NR^a$-heterocyclyl, carboxy, sulfonyl, sulfamoyl or sulfonamido, in which each alkyl, alkoxy, aryl, heteroaryl and heterocyclyl are optionally substituted with halo, $C_{1-6}$-alkyl, $C_{1-6}$-alkoxy, hydroxy, halo-$C_{1-6}$-alkyl, $C_{6-10}$-aryl, heteroaryl, $C_{6-10}$-aryloxy or $C_{3-7}$cycloalkyl;

$R^a$ and $R^b$ for each occurrence, are independently H, $C_{1-6}$-alkyl, $C_{3-7}$-cycloalkyl, $C_{6-10}$-aryl, heterocyclyl, heteroaryl or $R^a$ and $R^b$ which are attached to the same nitrogen, may form together with the nitrogen to which they are attached a 5- to 7-membered saturated heterocyclyl;

$R^2$ is H, $C_{1-6}$-alkoxy, halo-$C_{1-6}$-alkyl or halogen;

$R^3$ and $R^4$ are independently H, $C_{1-6}$-alkyl or $C_{3-7}$cycloalkyl; wherein alkyl can be optionally substituted with $C_{1-6}$alkoxy, halogen, hydroxy, or $R^3$ and $R^4$ can form together with the atoms to which they are attached a 4- to 7-membered heterocyclyl or a 3- to 7-membered cycloalkyl; and when A is naphthyl then one of $R^3$, $R^4$ is other than H;

$R^5$ is H or $C_{1-6}$-alkyl; or $R^5$ and $R^3$ form together with the atoms to which they are attached a 4- to 7-membered saturated heterocyclyl; or $R^5$ and $R^2$ form together with the atoms to which they are attached a 5- to 7-membered ring saturated heterocyclyl which may be optionally substituted with oxo;

n is 0, 1, 2, 3, 4 or 5;

with the proviso that compound of Formula I is not (3-o-tolylpyridin-4-yl)methanol, (3-methoxy-5-phenylpyridin-4-yl)methanol, (3-(2-fluorophenyl)-5-methoxypyridin-4-yl)methanol, (3-(4-fluorophenyl)-5-methoxypyridin-4-yl)methanol, (3-fluoro-5-(4-fluorophenyl)pyridin-4-yl)methanol, (3-(4-fluorophenyl)pyridin-4-yl)methanol, (3-fluoro-5-phenylpyridin-4-yl)methanol, (3-chloro-5-phenylpyridin-yl)methanol, (3-chloro-5-(2-fluorophenyl)pyridin-4-yl)methanol, (3-fluoro-5-(2-fluorophenyl)pyridin-4-yl)methanol, (3-(2-fluorophenyl)pyridin-4-yl)methanol, (3-phenylpyridin-4-yl)methanol, (3-chloro-5-(4-fluorophenyl)pyridin-4-yl)methanol, (3-chloro-5-(3-fluorophenyl)pyridin-4-yl)methanol, (3-fluoro-5-(3-fluorophenyl)pyridin-4-yl)methanol, (3-(3-fluorophenyl)-5-methoxypyridin-4-yl)methanol or (3-(3-fluorophenyl)pyridin-4-yl)methanol.

Certain compounds of Formula I wherein $R^3$ is H, include compounds of Formula II:

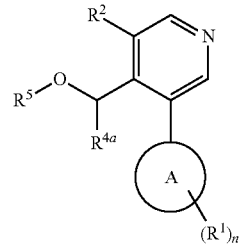

II or a pharmaceutically acceptable salt thereof, wherein A, $R^1$, $R^2$, $R^5$ and n have the definitions of Formula I, supra, and $R^{4a}$ is $C_{1-6}$-alkyl or $C_{3-7}$cycloalkyl; wherein alkyl can be optionally substituted with alkoxy, halogen or hydroxy or $R^{4a}$ and $R^5$ form together with the atoms to which they are attached a 4- or 7-membered heterocyclyl.

Certain compounds of Formula I or II include compounds of Formula III:

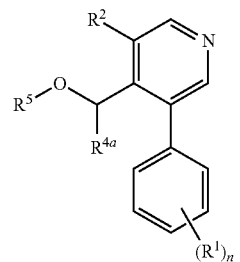

III or a pharmaceutically acceptable salt thereof, wherein $R^1$, $R^2$, $R^{4a}$, $R^5$ and n have the definitions of Formulae I and II, supra. In one aspect of this embodiment, n is 1 or 2, $R^1$ is in the para position and is CN, and the optional $R^1$ substituent is in the meta position and is $C_{1-6}$-alkyl, $C_{1-6}$alkoxy or halo. The para and meta positions are the positions with reference to the point of attachment of the phenyl to the pyridine moiety.

Certain compounds of Formula I or II include compounds of Formula IV:

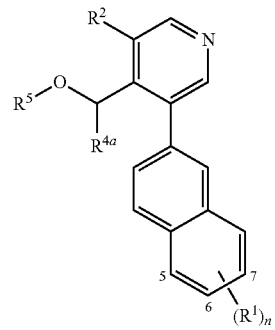

IV or a pharmaceutically acceptable salt thereof, wherein $R^1$, $R^2$, $R^{4a}$, and n have the definitions of Formulae I and II, supra. In one aspect of this embodiment, n is 1 or 2, $R^1$ for each occurrence is independently $C_{1-6}$-alkoxy, cyano or halo and $R^1$ is in the 6- or 7-position of the naphthyl.

Certain compounds of Formula I or II include compounds of Formula IV:

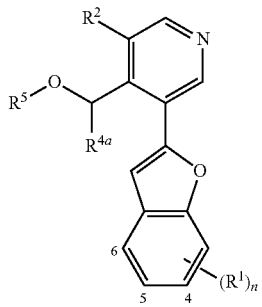

or a pharmaceutically acceptable salt thereof, wherein $R^1$, $R^2$, $R^{4a}$, $R^5$ and n have the definitions of Formulae I and II, supra. In one aspect of this embodiment, n is 1 or 2, $R^1$ at each occurrence is independently CN or halo and $R^1$ is at the 4-, 5- or 6-position of the benzofuranyl.

In one embodiment, the invention pertains to compounds of Formula I or a pharmaceutically acceptable salt thereof, wherein $R^3$ and $R^4$ are independently $C_{1-6}$-alkyl; wherein alkyl can be optionally substituted with $C_{1-6}$alkoxy, halogen, hydroxy or $R^3$ and $R^4$ can form together with the atoms to which they are attached a 4- to 7-membered heterocyclyl or a 3- to 7-membered cycloalkyl. In a further aspect of this embodiment, $R^3$ and $R^4$ are independently $C_{1-6}$-alkyl; wherein alkyl can be optionally substituted with $C_{1-6}$alkoxy, halogen, hydroxy.

In one embodiment, the invention pertains to compounds according to anyone of Formulae I to V or of any classes and subclasses described supra, or a pharmaceutically acceptable salt thereof, wherein n is 1 or 2 and each $R^1$ is independently halo, $C_{1-6}$-alkyl, cyano, —S—$C_{1-6}$-alkyl, $C_{1-6}$-alkoxy, halo-$C_{1-6}$-alkoxy, $C_{1-6}$-alkoxy-$C_{1-6}$-alkoxy, s-alkyl, di-$C_{1-6}$-alkylamino, $C_{1-4}$-alkylamino or heterocyclyl. In another aspect of this embodiment, n is 1 or 2 and $R^1$ is independently halo, $C_{1-6}$-alkyl, cyano, or $C_{1-6}$-alkoxy.

In another embodiment, the invention pertains to compounds according to Formula I or II, wherein A is phenyl, n is 2 and $R^1$ is halo, $C_{1-6}$-alkyl, cyano, or $C_{1-6}$-alkoxy.

In another embodiment, the invention pertains to compounds according to anyone of Formulae I to V or of any classes and subclasses described supra, or a pharmaceutically acceptable salt thereof, wherein $R^2$ is H or halo. In one aspect of this embodiment $R^2$ is halo. In a further aspect of this embodiment $R^2$ is fluoro or chloro.

In another embodiment, the invention pertains to compounds according to anyone of Formulae I to V or a pharmaceutically acceptable salt thereof, wherein $R^5$ is H or $C_{1-6}$-alkyl; or $R^5$ and $R^{4a}$ or $R^5$ and $R^4$ form together with the atoms to which they are attached a 4- to 7-membered ring saturated heterocyclyl. In one aspect of this embodiment, $R^5$ is H.

In another embodiment, the invention pertains to compounds according to anyone of Formulae II, III IV and V or a pharmaceutically acceptable salt thereof, wherein $R^{4a}$ is $C_{1-6}$ alkyl optionally substituted with $C_{1-6}$alkoxy, halogen or hydroxy. In one aspect of this embodiment $R^{4a}$ is methyl.

In yet another embodiment, the invention pertains to compounds according to anyone of Formulae II, III, IV and V wherein the stereochemistry at the —CH($R^{4a}$)— chiral center is (S). In another embodiment, the invention pertains to compounds of Formulae II, III, IV and V wherein the stereochemistry at the —CH($R^{4a}$)— chiral center is (R).

In another embodiment, some compounds of the invention may have selectivity for aldosterone synthase (CYP11B2) relative to 11-beta hydroxylase (CYP11B1).

In another embodiment n, $R^1$, $R^2$, $R^3$, $R^4$, $R^5$ groups are those defined by the n, $R^1$, $R^2$, $R^3$, $R^4$, $R^5$ groups in the Examples section below.

In another embodiment, individual compounds according to the invention are those listed in the Examples section below, or a pharmaceutically acceptable salt thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S). The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80 enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric add, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^{1}H$, $^{2}H$ or D, $^{3}H$); any carbon represented by "C" in any of the formulae herein is intended to represent all isotopic forms of carbon (e.g. $^{11}C$, $^{13}C$, $^{14}C$); any nitrogen represented by "N" is intended to represent all isotopic forms of nitrogen (e.g. $^{14}N$, $^{15}N$). Other examples of isotopes that are included in the invention include isotopes of oxygen, sulfur, phosphorous, fluorine, iodine and chlorine, such as $^{18}F$ $^{31}P$, $^{32}P$, $^{35}S$, $^{35}Cl$, $^{125}I$. The invention includes various isotopically labeled compounds as defined herein, for example those into which radioactive isotopes, such as $^{3}H$, $^{13}C$, and $^{14}C$ are present. In one embodiment, the atoms in the formulae herein occur in their natural abundance. In another embodiment, one or more hydrogen atom may be enriched in $^{2}H$; or/and one or more carbon atom may be enriched in $^{11}C$, $^{13}C$ or $^{14}C$; or/and one or more nitrogen may be enriched in $^{14}N$. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula I, II, III, IV or V. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-enriched compounds of formula I, II, III, IV or V can generally be prepared by conventional techniques known to those skilled in the art or by processes analogous to those described in the accompanying Examples and Preparations using an appropriate isotopically-enriched reagent in place of the non-enriched reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula I, II, III, IV or V that contain groups capable of acting as donors and/or acceptors for hydrogen bonds may be capable of forming co-crystals with suitable co-crystal formers. These co-crystals may be prepared from compounds of formula I, II, III, IV or V by known co-crystal forming procedures. Such procedures include grinding, heating, co-subliming, co-melting, or contacting in solution compounds of formulae I to V with the co-crystal former under crystallization conditions and isolating co-crystals thereby formed. Suitable co-crystal formers include those described in WO 2004/078163. Hence the invention further provides co-crystals comprising a compound of formula I, II, III, IV or V.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or amelioration of a symptom, alleviation of a condition, slow or delay disease progression, or prevention of a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by aldosterone synthase and/or CYP11B1, or (ii) associated with aldosterone synthase and/or CYP11B1 activity, or (iii) characterized by abnormal activity of aldosterone synthase and/or CYP11B1; or (2) reduce or inhibit the activity of aldosterone synthase and/or CYP11B1; or (3) reduce or inhibit the expression of aldosterone synthase and/or CYP11B1. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of aldosterone synthase and/or CYP11B1; or at least partially reduce or inhibit the expression of aldosterone synthase and/or CYP11B1.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased tipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

General Synthetic Aspect:

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

The compounds of the invention can be synthesized using the methods described in the following schemes, examples, and by using art recognized techniques. All compounds described herein are included in the invention as compounds. Compounds of the invention may be synthesized according to at least one of the methods described in schemes 1 to 3.

Scheme 1 describes a general synthetic route to compounds of Formula (I): 3-bromopyridine (a) undergoes metallation in the presence of base (e.g. LDA) and is subsequently treated with carbonyl compound (b) to generate the alcohol (c). Alcohol c undergoes a coupling reaction with various boronic acids or esters (e) using standard Suzuki coupling conditions to generate the desired compound of Formula I. Alternatively, metallation of 3-bromopyridine (a) and trapping of the anion with an acid chloride (e.g. R$^3$C(O)Cl) or anhydride generates the corresponding carbonyl compound (f). Subsequently, ketone (f) undergoes Suzuki coupling with boronic acid or ester (e) to generate intermediate (g). Intermediate (g) undergoes nucleophilic addition with the nucleophile R$^1$M (e.g. R$^1$M is a hydride, a Grignard reagent, an organolithium reagent, an organozinc reagent or other organometallic reagent) to generate the desired compound of Formula I.

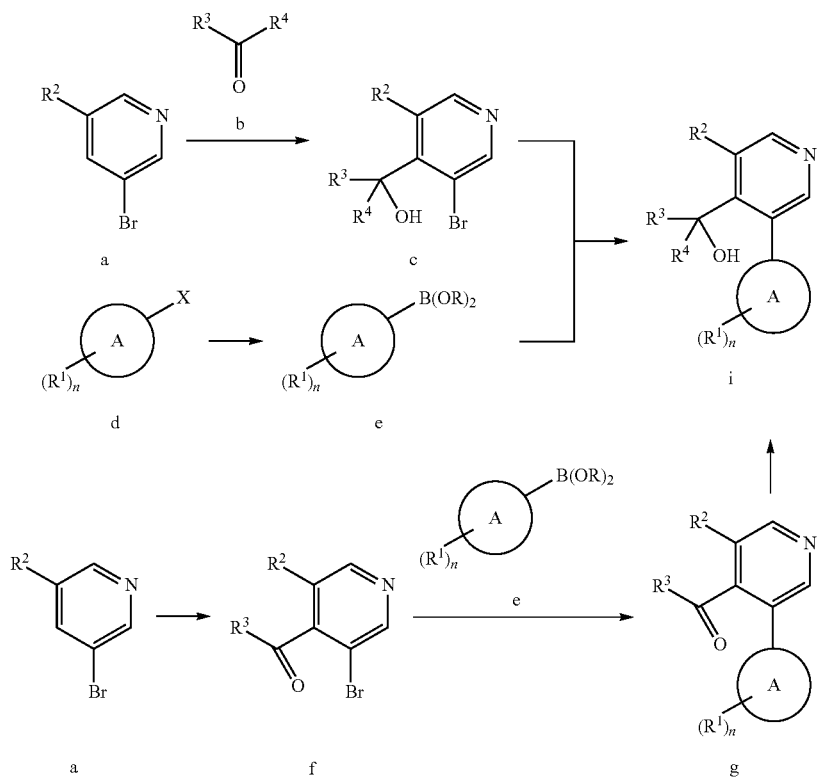

Scheme 1

Boronic acids or esters (e) wherein R is H or alkyl, are commercially available or are prepared from the corresponding halide or triflate (d) (e.g. X is Br, I, OTf) using Miyaura boration condition.

Furthermore, optionally substituted benzofuran can be treated with n-BuLi and trimethylborate, followed by hydrolysis with HCl to generate benzofuran-2-ylboronic acid.

Scheme 2 illustrates the synthesis of Compounds of Formula I or II wherein R$^3$ is H.

Scheme 2

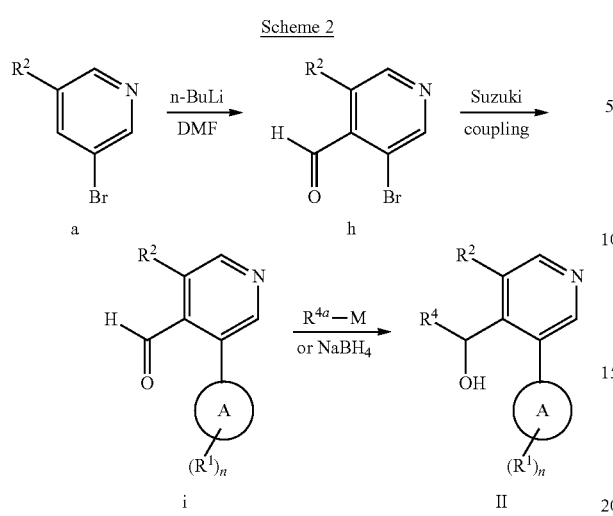

3-bromopyridine is treated with n-BuLi and DMF to generate aldehyde (h). Intermediate (h) subsequently undergoes coupling reaction with boronic acid or ester (e) using standard Suzuki coupling conditions as described in Scheme 1 to generate a compound of Formula I or II. Alternatively aldehyde (h) can be reduced to the alcohol using a reducing agent such as for example NaBH$_4$ to generate a compound of Formula I or II wherein R$^4$ is H.

Scheme 3 illustrates the synthesis of compounds of Formula I or II wherein A is benzothiazolyl, benzimidazolyl or benzoxazolyl.

Scheme 3

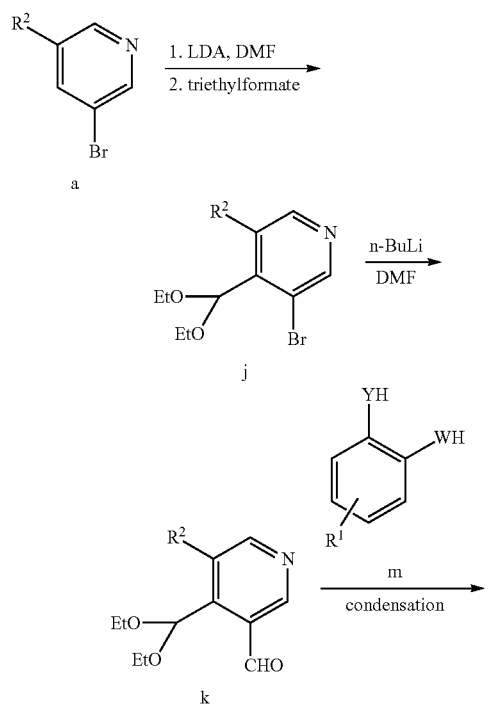

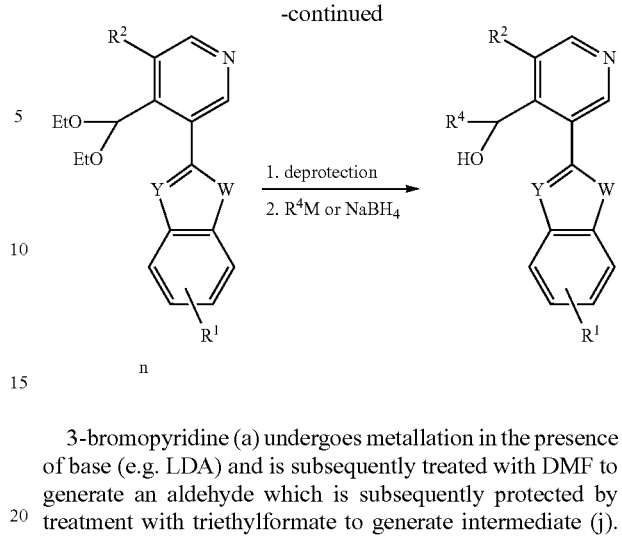

3-bromopyridine (a) undergoes metallation in the presence of base (e.g. LDA) and is subsequently treated with DMF to generate an aldehyde which is subsequently protected by treatment with triethylformate to generate intermediate (j). Intermediate (j) is then treated with n-BuLi, followed by addition of DMF to generate aldehyde (k). Aldehyde (k) subsequently undergoes condensation with various reagents (m) wherein Y and W are independently N, NH, N-methyl, O or S, to generate intermediate (n). After deprotection of the aldehyde followed with manipulation of the aldehyde group by known methods (e.g. nucleophilic addition of R$^4$M as previously described or reduction of aldehyde with NaBH$_4$), the desired compound of Formula I or II wherein A benzothiazolyl, benzimidazolyl or benzoxazolyl is obtained.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

In another aspect, the present invention provides a pharmaceutical composition comprising a compound of the present invention or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds according to anyone of formulae I to V in free form or in pharmaceutically acceptable salt form, exhibit valuable pharmacological properties, e.g. aldosterone synthase and/or CYP11B1 modulating properties, e.g. as indicated in in vitro and in vivo tests as provided in the next sections and are therefore indicated for therapy.

Compounds of the invention may be useful in the treatment of an indication selected from: hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive Cortisol level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess. Thus, as a further embodiment, the present invention provides the use of a compound according to anyone of formulae I to V or a pharmaceutically acceptable salt thereof in therapy. In a further embodiment, the therapy is selected from a disease which is ameliorated by inhibition of aldosterone synthase and/or CYP11B1. In another embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

In another embodiment, the invention provides a method of treating a disease which is ameliorated by inhibition of aldosterone synthase and/or CYP11B1 comprising administration of a therapeutically acceptable amount of a compound according to anyone of formulae I to V. In a further embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

The pharmaceutical composition or combination of the present invention can be in unit dosage of about 0.01-500 mg of active ingredient(s) for a subject of about 50-70 kg, or about 0.01-250 mg or about 0.01-150 mg or about 0.01-100 mg, or about 0.01-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.0001-500 mg/kg, or between about 0.0001-100 mg/kg, or between about 0.0003-10 mg/kg.

The activity of a compound according to the present invention can be assessed by the following in vitro & in vivo methods.

The activity of a compound according to the present invention can be assessed by the in vitro methods described below, and/or by the following in vitro & in vivo methods well-described in the art. See Fieber, A et al. (2005), "Aldosterone Synthase Inhibitor Ameliorates Angiotensin II—Induced Organ Damage," *Circulation,* 111:3087-3094.

In particular, the aldosterone synthase inhibitory activities in vitro can be determined by the following assay.

Human adrenocortical carcinoma NCI-H295R cell line was obtained from American Type Culture Collection (Manassas, Va.). Insulin/transferrin/selenium (ITS)-A supplement (100×), DMEM/F-12, antibiotic/antimycotic (100×), and fetal bovine serum (FBS) were purchased from Invitrogen (Carlsbad, Calif.). Anti-mouse PVT scintillation proximity assay (SPA) beads and NBS 96-well plates were obtained from GE Health Sciences (Piscataway, N.J.) and Corning (Acton, Mass.), respectively. Solid black 96-well flat bottom plates were purchased from Costar (Corning, N.Y.). Aldosterone and angiotensin (Ang II) were purchased from Sigma (St. Louis, Mo.). D-[1,2,6,7-$^3$H(N)]aldosterone was acquired from PerkinElmer (Boston, Mass.). Nu-serum was a product of BD Biosciences (Franklin Lakes, N.J.).

For in vitro measurement of aldosterone activity, human adrenocortical carcinoma NCI-H295R cells are seeded in NBS 96-well plates at a density of 25,000 cells/well in 100 μl of a growth medium containing DMEM/F12 supplemented with 10% FCS, 2.5% Nu-serum, 1 μg ITS/ml, and 1× antibiotic/antimycotic. The medium is changed after culturing for 3 days at 37° C. under an atmosphere of 5% $CO_2$/95% air. On the following day, cells are rinsed with 100 μl of phosphate-buffered saline (PBS) and incubated with 100 μl of treatment medium containing 1 μM Ang II and a compound at different concentrations in quadruplicate wells at 37° C. for 24 hr. At the end of incubation, 50 μl of medium is withdrawn from each well for measurement of aldosterone production by an SPA using mouse anti-aldosterone monoclonal antibodies.

Measurement of aldosterone activity can also be performed using a 96-well plate format. Each test sample is incubated with 0.02 μCi of D-[1,2,6,7-$^3$H(N)]aldosterone and 0.3 μg of anti-aldosterone antibody in PBS containing 0.1% Triton X-100, 0.1% bovine serum albumin, and 12% glycerol in a total volume of 200 μl at room temperature for 1 hr. Anti-mouse PVT SPA beads (50 μl) are then added to each well and incubated overnight at room temperature prior to counting in a Microbeta plate counter. The amount of aldosterone in each sample is calculated by comparing with a standard curve generated using known quantities of the hormone.

The in vitro inhibitory activities for CYP11B1 can be determined by the following assay.

The cell line NCI-H295R was originally isolated from an adrenocortical carcinoma and has been characterized in the literature through the stimulable secretion of steroid hormones and the presence of the enymes essential for steroidogenesis. Thus, the NCI-H295R cells have CYP11 B1 (steroid 11 β-hydroxylase). The cells show the physiological property of zonally undifferentiated human foetal adrenocortical cells which, however, have the capacity to produce the steroid hormones which are formed in the three, phenotypically distinguishable zones in the adult adrenal cortex.

The NCI-H295R cells (American Type Culture Collection, ATCC, Rockville, Md., USA) are grown in Dulbeoco's Modified Eagle'Ham F-12 Medium (DME/F12), which has been supplemented with Ulroser SF Serum (Soprachem, Cergy-Saint-Christophe, France), insulin, transferrin, selenite (I-T-S, Becton Dickinson Biosiences, Franklin lakes, NJ, USA) and antibiotics in 75 cm$^2$ cell culture vessels at 37° C. and in a 95% air-5% carbon dioxide atmosphere. The cells are subsequently transferred for colony formation into a 24-well incubation vessel. They are cultivated there in DME/F12 medium, which is now supplemented with 0.1% bovine serum instead of Ultroser SF for 24 hours. The experiment is initiated by cultivating the cells in DME/F12 medium which is supplemented with 0.1% bovine serum albumin and test compound, in the presence or absence of cell stimulants, for 72 hours. The test substance is added in a concentration range from 0.2 nanomolar to 20 millimolar. Cell stimulants which can be used are angiotensin 11 (1D or 100 nanomolar), potassium ions (16 millimolar), forskolin (10 micromolar) or a combination of two stimulants.

The excretion of aldosterone, cortisol, corticosterone and estradiol/estrone into the culture medium can be detected and quantified by commercially available, specific monoclonal antibodies in radioimmunoassays in accordance with the manufacturers instructions.

Inhibition of the release of certain steroids can be used as a measure of the respective enzyme inhibition by the added test compounds. The dose-dependent inhibition of enzymic activity by a compound is calculated by means of an inhibition plot which is characterized by an IC50.

The IC50 values for active test compounds are ascertained by a simple linear regression analysis in order to construct inhibition plots without data weighting. The inhibition plot is calculated by fitting a 4-parameter logistic function to the raw data points using the least squares method. The equation of the 4-parameter logistic function is calculated as follows: $Y=(d-a)/((1+(x/c)b))+a$, where: a=minimum data level, b=gradient, I c=ICED, d=maximum data level, x=inhibitor concentration.

The inhibition activity of aldosterone production can also be expressed in percentage inhibition (% inhibition) at a given concentration (e.g. % inhibition at 1 μM), which is the aldosterone level when the cell is treated with the given concentration of a compound of this invention (e.g. concentration of 1 μM) versus the aldosterone excretion when cell is free of the compound of the invention:

% inhibition aldosterone production=$[(Y-X)/Y]\times 100$ wherein X is the level of aldosterone when the cell is treated with a compound according to anyone of Formulae I to V, or a pharmaceutically acceptable salt thereof; and Y is the level of aldosterone when the cell is free of compound according to anyone of Formulae I to V.

The inhibition activity of CYP11B1 production can also be expressed in percentage inhibition (% inhibition) at a given concentration (e.g. % inhibition at 1 μM), which is the cortisol level when cell is treated with the given concentration of a compound of the invention (e.g. concentration of 1 μM) versus the cortisol excretion when cell is free of the compound of the invention.

% inhibition cortisol production=$[(Y'-X')/Y']\times 100$ wherein X' is the level of cortisol when the cell is treated with a compound according to anyone of Formulae I to V, or a pharmaceutically acceptable salt thereof; and Y' is the level of cortisol when the cell is free of compound according to anyone of Formulae I to V.

Using the test assays for measuring inhibition of CYP11B1 (cortisol) and CYP11B2 (aldosterone), as described above, compounds of the invention exhibited inhibitory efficacy as shown in Table 1, provided infra.

TABLE 1

Inhibitory Activity of Compounds

| Example # | Aldosterone (cell) nM | Cortisol (cell) nM |
|---|---|---|
| 46 | 76.5 | 672.5 |
| 37 | 120 | 12607 |

TABLE 1-continued

Inhibitory Activity of Compounds

| Example # | Aldosterone (cell) nM | Cortisol (cell) nM |
|---|---|---|
| 32 | 154 | 15035 |
| 16 (enantiomer-2) | 106 | 9418 |
| 5 (enantiomer-1) | 41.5 | 366.5 |
| 13d (enantiomer-2) | 2.5 | 1067 |
| 24 | 261.5 | |
| 14 (enantiomer-1) | 132 | 3387 |
| 28 (enantiomer-1) | 23.5 | 782.5 |
| 30 | 144.5 | 4236 |

The compound of the present invention, or a pharmaceutically acceptable salt thereof, may be administered either simultaneously with, or before or after, one or more other therapeutic agent. The compound of the present invention, or a pharmaceutically acceptable salt thereof, may be administered separately, by the same or different route of administration, or together in the same pharmaceutical composition as the other agents.

In one embodiment, the invention provides a product comprising a compound according to anyone of formulae I to V or a pharmaceutically acceptable salt thereof, and at least one other therapeutic agent as a combined preparation for simultaneous, separate or sequential use in therapy. In one embodiment, the therapy is the treatment of a disease or condition mediated by aldosterone synthase and/or CYP11B1. Products provided as a combined preparation include a composition comprising the compound according to anyone of formulae I to V, or a pharmaceutically acceptable salt thereof, and the other therapeutic agent(s) together in the same pharmaceutical composition, or the compound according to anyone of formulae I to V, or a pharmaceutically acceptable salt thereof, and the other therapeutic agent(s) in separate form, e.g. in the form of a kit.

In one embodiment, the invention provides a pharmaceutical composition comprising a compound according to anyone of formulae I to V, or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound according to anyone of formulae I to V, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention, or a pharmaceutically acceptable salt thereof, and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention, or a pharmaceutically acceptable salt thereof, and the other therapeutic agent. Accordingly, the invention provides the use of a compound according to anyone of formulae I to V, or a pharmaceutically acceptable salt thereof, for treating a disease or condition mediated by aldosterone synthase and/or CYP11B1, wherein the medicament is prepared for administration with another therapeutic agent. The invention also provides the use of another therapeutic agent for treating a disease or condition mediated by aldosterone synthase and/or CYP11B1, wherein the medicament is administered with a compound according to anyone of formulae I to V, or a pharmaceutically acceptable salt thereof.

The invention also provides a compound according to anyone of formulae I to V, or a pharmaceutically acceptable salt thereof, for use in a method of treating a disease or condition mediated by aldosterone synthase and/or CYP11B1, wherein the compound according to anyone of formulae I to V, or a pharmaceutically acceptable salt thereof, is prepared for administration with another therapeutic agent. The invention also provides another therapeutic agent for use in a method of treating a disease or condition mediated by aldosterone synthase and/or CYP11B1, wherein the other therapeutic agent is prepared for administration with a compound anyone of formulae I to V, or a pharmaceutically acceptable salt thereof. The invention also provides a compound according to anyone of formulae I to V, or a pharmaceutically acceptable salt thereof, for use in a method of treating a disease or condition mediated by aldosterone synthase and/or CYP11B1, wherein the compound according to anyone of formulae I to V, or a pharmaceutically acceptable salt thereof, is administered with another therapeutic agent. The invention also provides another therapeutic agent for use in a method of treating a disease or condition mediated by aldosterone synthase and/or CYP11B1, wherein the other therapeutic agent is administered with a compound according to anyone of formulae I to V, or a pharmaceutically acceptable salt thereof.

The invention also provides the use of a compound according to anyone of formulae I to V, or a pharmaceutically acceptable salt thereof, for treating a disease or condition mediated by aldosterone synthase and/or CYP11B1, wherein the patient has previously (e.g. within 24 hours) been treated with another therapeutic agent. The invention also provides the use of another therapeutic agent for treating a disease or condition mediated by aldosterone synthase and/or CYP11B1, wherein the patient has previously (e.g. within 24 hours) been treated with a compound according to anyone of formulae I to V, or a pharmaceutically acceptable salt thereof.

In one embodiment, the other therapeutic agent is selected from: HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker, or a CETP inhibitor.

In still another embodiment, the invention pertains, at least in part, to methods wherein the compound of the invention (e.g., a compound of according to anyone of Formulae I to V or a compound otherwise described herein) is administered in combination with a second agent.

The term "in combination with" a second agent or treatment includes co-administration of the compound of the invention (e.g., a compound according to anyone of Formulae I to V or a compound otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g., an aldosterone synthase associated disorder, such as, for example, hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, and fibrinoid necrosis of coronary arteries. Furthermore, the second agent may be any agent of benefit to the patient when administered in combination with the administration of a compound of the invention.

Examples of second agents include HMG-Co-A reductase inhibitors, angiotensin II receptor antagonists, angiotensin converting enzyme (ACE) Inhibitors, calcium channel blockers (CCB), dual angiotensin converting enzyme/neutral endopeptidase (ACE/NEP) inhibitors, endothelin antagonists, renin inhibitors, diuretics, ApoA-I mimics, anti-diabetic agents, obesity-reducing agents, aldosterone receptor blockers, endothelin receptor blockers, and CETP inhibitors.

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

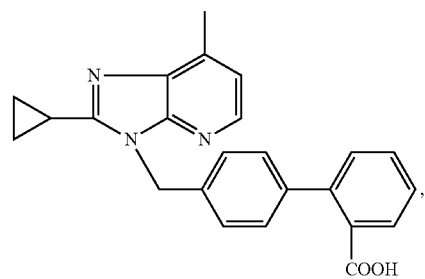 [SMILES: Cc1ccnc2c1nc(C1CC1)n2Cc1ccc(-c2ccccc2C(=O)O)cc1]

the compound with the designation SC-52458 of the following formula

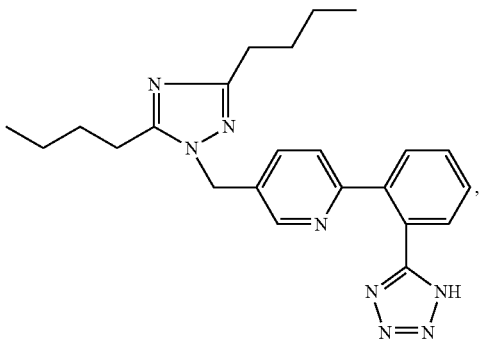 [SMILES: CCCCc1nc(CCCC)n(Cc2ccc(-c3ccccc3-c3nnn[nH]3)nc2)n1]

and the compound with the designation ZD-8731 of the following formula

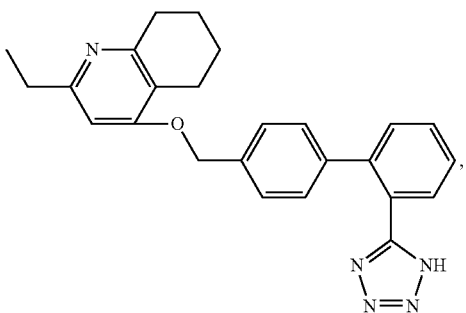 [SMILES: CCc1cc(OCc2ccc(-c3ccccc3-c3nnn[nH]3)cc2)c2c(n1)CCCC2]

or, in each case, a pharmaceutically acceptable salt thereof.

Preferred $AT_1$-receptor antagonist are those agents which have been marketed, most preferred is valsartan or a pharmaceutically acceptable salt thereof.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enalprilat, fosinopril, imidapril, lisinopril, moveltopril, perindopril, quinapril, ramipril, spirapril, temocapril, and trandolapril, or, pharmaceuticals salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "dual angiotensin converting enzyme/neutral endopetidase (ACE/NEP) inhibitor" includes omapatrilate (cf. EP 629627), fasidotril or fasidotrilate, or pharmaceutically acceptable salts thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-proly I-L-phenylalanyl-N-[2-hydroxy-5-methyl-1-(2-methylpropyl)-4-[[[2-methyl-1-[[(2-pyridinylmethyl)amino]carbonyl]butyl]amino]carbonyl]hexyl]-N-alfa-methyl-L-histidinamide); terlakiren (chemical name: [R-(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteinamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)],2S*,3R*]]-N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

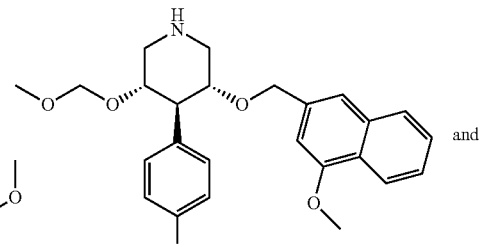

(A)

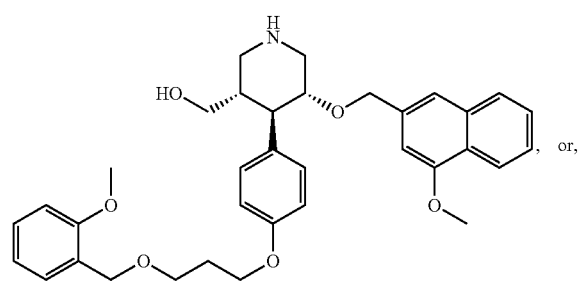

(B)

pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F)

The term "anti-diabetic agent" includes insulin secretion enhancers that promote the secretion of insulin from pancreatic β-cells. Examples include biguanide derivatives (e.g., metformin), sulfonylureas (SU) (e.g., tolbutamide, chlorpropamide, tolazamide, acetohexamide, 4-chloro-N-[(1-pyrrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazoie, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

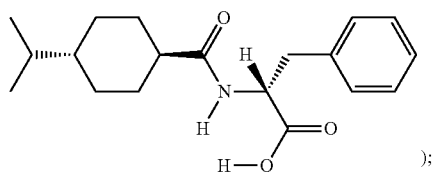 [SMILES: CC(C)[C@H]1CC[C@H](C(=O)N[C@H](Cc2ccccc2)C(=O)O)CC1]

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinylcarbonyl)-propionate dihydrate mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al. in *Diabetologia*, 28, 1985, 704-707 and in U.S. Pat. No. 5,705,483.

The term "GLP-1 agonists" includes variants and analogs of GLP-1(7-36)NH$_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. Further examples include GLP-1 (7-37), in which compound the carboxy-terminal amide functionality of Arg$^{36}$ is displaced with Gly at the 37$^{th}$ position of the GLP-1(7-36)NH$_2$ molecule and variants and analogs thereof. Including GLN$^g$-GLP-1(7-37), D-GLN$^g$-GLP-1(7-37), acetyl LYS$^g$-GLP-1(7-37), LYS$^{18}$-GLP-1(7-37) and, in particular, GLP-1(7-37)OH, VAL$^8$-GLP-1(7-37), GLY$^B$-GLP-1(7-37), THR$^B$-GLP-1(7-37), MET$^E$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluorobenzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDFIK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α$_2$-adrenergic antagonists; and pharmaceutically acceptable salts thereof.

The term "obesity-reducing agent" includes lipase inhibitors (e.g., orlistat) and appetite suppressants (e.g., sibutramine and phentermine).

The term "aldosterone receptor blocker" includes spironolactone and eplerenone.

The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenono-lactone derivatives and phosphate-containing analogs of cholesteryl ester disclosed in *J. Antibiot.*, 49(8): 815-816 (1996), and *Bioorg. Med. Chem. Lett.*; 6:1951-1954 (1996), respectively. Furthermore, the CETP inhibitors also include those disclosed in WO2000/017165, WO2005/095409 and WO2005/097806.

In one embodiment, the invention provides a pharmaceutical composition comprising a therapeutically effective amount of a compound according to anyone of formulae I to V or a pharmaceutically acceptable salt thereof, and one or more pharmaceutically acceptable carriers.

In one embodiment, the invention provides a combination, in particular a pharmaceutical combination, comprising a therapeutically effective amount of the compound according to anyone of formulae I to V or a pharmaceutically acceptable salt thereof and one or more therapeutically active agents selected from HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker, or a CETP inhibitor.

In one embodiment, the invention provides a method of modulating aldosterone synthase and/or CYP11B1 activity in a subject, wherein the method comprises administering to the subject a therapeutically effective amount of the compound according to anyone of formulae I to V, or a pharmaceutically acceptable salt thereof.

In one embodiment, the invention provides a method of treating a disorder or a disease in a subject mediated by aldosterone synthase and/or CYP11B1 wherein the method comprises administering to the subject a therapeutically effective amount of the compound according to anyone of formulae I to V, or a pharmaceutically acceptable salt thereof.

In one embodiment, the invention provides a method of treating a disorder or a disease in a subject mediated by aldosterone synthase and/or CYP11B1, wherein the disorder or the disease is selected from hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive Cortisol level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess.

Thus, as a further embodiment, the present invention provides the use of a compound according to anyone of formulae I to V, or a pharmaceutically acceptable salt thereof, in therapy. In a further embodiment, the therapy is selected from a disease which is ameliorated by inhibition of aldosterone synthase and/or CYP11B1. In another embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

In one embodiment, the invention provides a compound according to anyone of formulae I to V, or a pharmaceutically acceptable salt thereof, for use as a medicament.

In one embodiment, the invention provides the use of a compound according to the anyone of formulae I to V, or a pharmaceutically acceptable salt thereof, for the treatment of a disorder or disease in a subject mediated by aldosterone synthase and/or CYP11B1.

In one embodiment, the invention provides the use of a compound according to anyone of formulae I to V, or a pharmaceutically acceptable salt thereof, in the manufacture of a medicament for the treatment of a disorder or disease in a subject characterized by an activity of aldosterone synthase and/or CYP11B1, wherein said disorder or disease is in particular selected from hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive Cortisol level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess.

Thus, as a further embodiment, the present invention provides the use of a compound according to anyone of formulae I to V, or a pharmaceutically acceptable salt thereof, in therapy. In a further embodiment, the therapy is selected from a disease which is ameliorated by inhibition of aldosterone synthase and/or CYP11B1. In another embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

| Exemplification of the Invention: Common abbreviations: | |
|---|---|
| ACN | acetonitrile |
| AIBN | 2,2-azobisisobutyronitrile |
| br | broad |
| BSA | bovine serum albumin |
| Bu | butyl |
| cPr | cyclopropyl |
| d | doublet |
| dd | doublet of doublets |
| DCM | dichloromethane |
| DIEA | diethylisopropylamine |
| DME | 1,4-dimethoxyethane |
| DMF | N,N-dimethylformamide |
| DMSO | dimethylsulfoxide |
| EtOAc | ethyl acetate |
| ESI | electrospray ionization |
| EtOAc | ethyl acetate |
| h | hour(s) |
| HPLC | high pressure liquid chromatography |
| HRMS: | high resolution mass spectrometry |
| LCMS | liquid chromatography and mass spectrometry |
| MeOH | methanol |
| MeOD | deuteriated methanol |
| MS | mass spectrometry |
| MW | microwave |
| m | multiplet |
| min | minutes |
| mL | milliliter(s) |
| m/z | mass to charge ratio |
| NMR | nuclear magnetic resonance |
| ppm | parts per million |
| rac | racemic |
| rt or RT | room temperature |
| s | singlet |
| $PdCl_2(dppf) \cdot CH_2Cl_2$ | Dichloro[1,1'-ferrocenylbis(diphenyl-phosphine)] palladium(II) dichloromethane |
| $PdCl_2(PPh_3)_2$ | bis(triphenylphosphine)palladium(II) chloride |
| t | triplet |
| TFA | trifluoroacetic acid |
| THF | tetrahydrofuran |
| TLC | thin layer chromatography |

The following examples are intended to illustrate the invention and are not to be construed as being limitations thereon. Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Example 1

Synthesis of 4-(4-(1-hydroxyethyl)pyridin-3-yl)-2-methylbenzonitrile

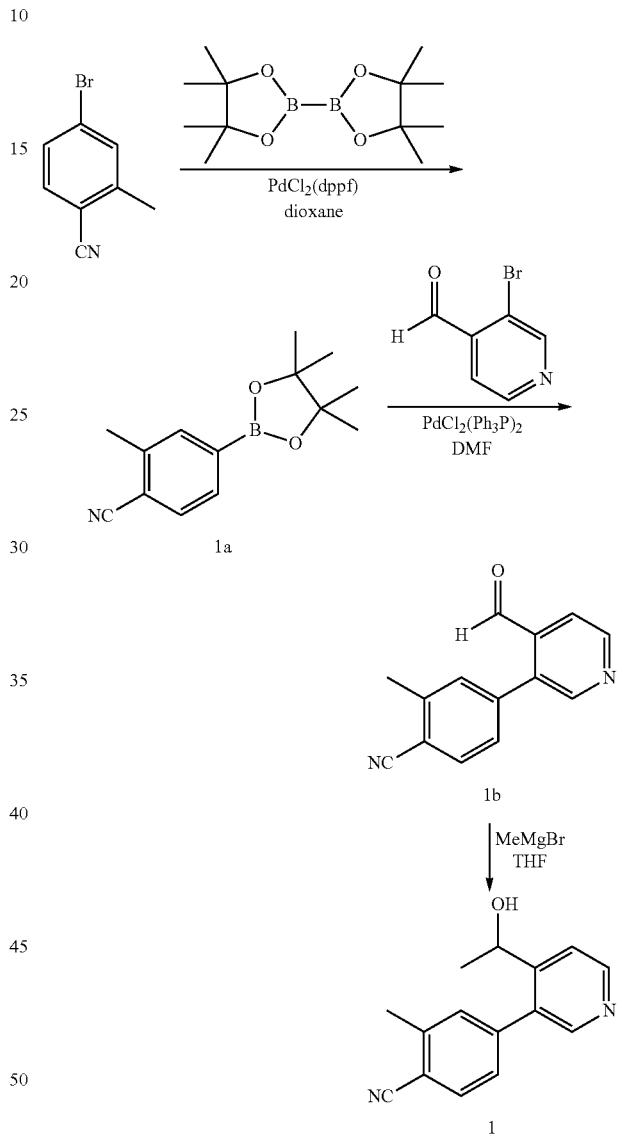

Step 1: 2-methyl-4-(4,4,5,5-tetramethyl-1,3,2-dioxaborolan-2-yl)benzonitrile (1a)

A mixture of 4-bromo-2-methylbenzonitrile (1 g, 5.10 mmol), bis(pinacolato)diboron (1.554 g, 6.12 mmol), potassium acetate (1.001 g, 10.20 mmol) and $PdCl_2(dppf) \cdot CH_2Cl_2$ adduct (0.208 g, 0.255 mmol) in 1,4-Dioxane (12.75 ml) was heated to 80° C. for 5 hr. The mixture was concentrated, and the residue was purified via Biotage (0-10% EtOAc/heptane; SNAP50 column) giving compound 1 as white solid (860 mg, 69%). $^1$H NMR (400 MHz, CDCl$_3$) δ ppm 1.28 (s, 12H) 2.38-2.52 (m, 3H) 7.51 (d, J=7.64 Hz, 1H) 7.55-7.64 (m, 1H) 7.67 (s, 1H).

Step 2: 4-(4-formylpyridin-3-yl)-2-methylbenzonitrile (1b)

A mixture of 1a (430 mg, 1.769 mmol), 3-bromo-4-pyridinecarboxaldehyde (299 mg, 1.608 mmol), sodium carbonate (2N in water, 1.608 mL, 3.22 mmol), bis(triphenylphosphine)palladium(II) chloride (28.2 mg, 0.040 mmol) in DMF (6.432 mL) was heated to 100° C. for 2 hrs. The mixture was quenched with saturated NaHCO₃ and extracted with EtOAc two times, dried over magnesium sulfate, filtered and concentrated. The residue was purified via Biotage (0-50% EtOAc/heptane; 25M column) giving compound 1b as white solid (280 mg, 78%). LC-MS (M+1) 223.1, t=1.28 min.

Step 3: 4-(4-(1-hydroxyethyl)pyridin-3-yl)-2-methylbenzonitrile (1)

A solution of methylmagnesium bromide (3M in Et₂O, 1260 µl, 3.78 mmol) was added dropwise to a solution of 1b (280 mg, 1.260 mmol) in dry THF (1.3 mL) at −78° C. The resulting mixture was slowly warmed up to 0° C. during 2 hrs. The mixture was quenched with saturated NH₄Cl and extracted with EtOAc two times, dried over magnesium sulfate, filtered and concentrated. The residue was purified via Biotage (20-80% EtOAc/heptane; 25S column) giving compound 3 as white solid (129 mg, 43%). ¹H NMR (400 MHz, chloroform-d) δ ppm 1.35 (d, J=6.44 Hz, 3H) 2.62 (s, 3H) 4.96 (q, J=6.44 Hz, 1H) 7.19-7.34 (m, 2H) 7.70 (d, J=7.89 Hz, 1H) 7.75 (d, J=5.31 Hz, 1H) 8.38 (s, 1H) 8.64 (d, J=5.31 Hz, 1H). LC-MS (M+1) 239.1, t=0.88 min.

The racemic mixture 3 (114 mg, 0.478 mmol) was separated by chiral HPLC (ChiralPak OD-H, 20×250 mm, 18 mL/min, 90% heptane 10% ethanol) giving 1-(enantiomer-1) as white solid (43 mg) (retention time: 10.15 min) and 1-(enantiomer-2) as white solid (42 mg) (retention time: 12.74 min).

Example 2

Synthesis of 6-(4-(1-hydroxyethyl)pyridin-3-yl)-2-naphthonitrile

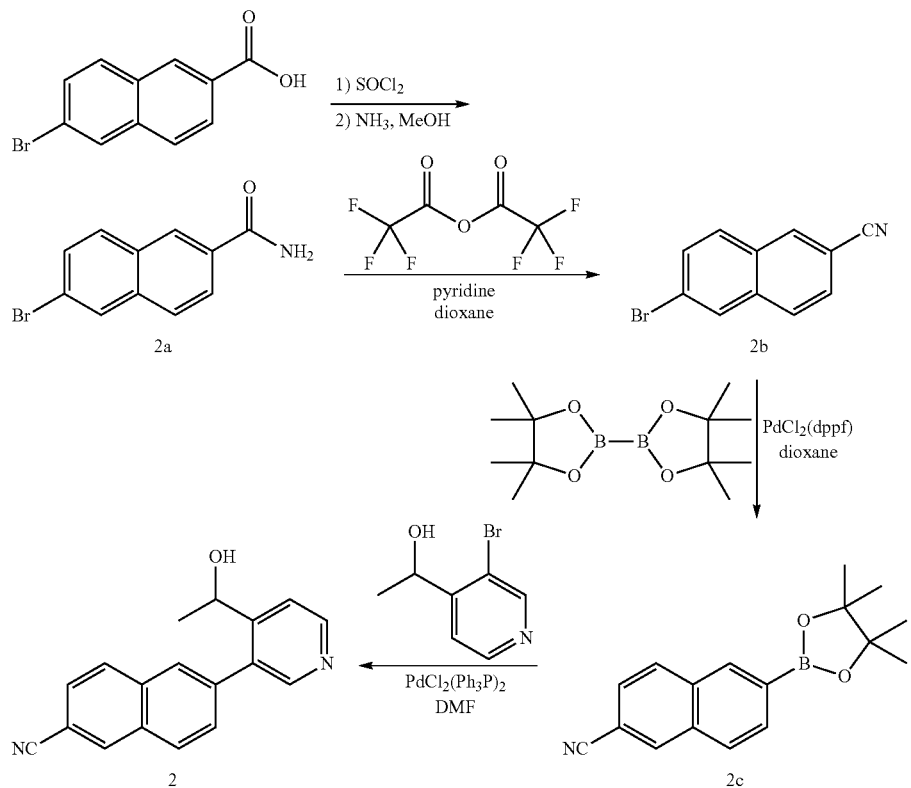

Step 1: 6-bromo-2-naphthamide (2a)

6-bromo-2-naphthoic acid (2 g, 7.97 mmol) was stirred in thionyl chloride (13.28 ml) at 70° C. for 16 h. Solvent was evaporated, and the residue was dissolved in CH₂Cl₂ and concentrated again. To the acid chloride intermediate was added ammonia (7N in MeOH, 13.66 ml, 96 mmol) and the mixture was stirred at room temperature for 3 h. The reaction mixture was concentrated, diluted in ethyl acetate and filtered. The solid was rinsed with ethyl acetate and then dried. The title compound 2a (1.802 g, 90%) was isolated as beige solid. LC-MS (M+1) 251.9, t=1.34 min.

Step 2: 6-bromo-2-naphthonitrile (2b)

To 6-bromo-2-naphthamide (1 g, 4.00 mmol) in 1,4-dioxane (8.00 ml) at 0° C. was added pyridine (0.647 ml, 8.00 mmol) and then trifluoroacetic anhydride (0.621 ml, 4.40 mmol) dropwise. The reaction was stirred at room temperature for 3 h. The mixture was quenched with H₂O and extracted with EtOAc two times, dried over magnesium sulfate, filtered, concentrated. The title compound 2b (653 mg, 70%) was isolated as beige solid, and used as is for the next step.

Step 3: 6-(4,4,5,5-tetramethyl-1,3,2-dioxaborolan-2-yl)-2-naphthonitrile (2c)

A mixture of 6-bromo-2-naphthonitrile 2b (653 mg, 2.81 mmol), bis(pinacolato)diboron (857 mg, 3.38 mmol), potassium acetate (552 mg, 5.63 mmol) and PdCl$_2$(dppf).CH$_2$Cl$_2$ adduct (115 mg, 0.141 mmol) in 1,4-Dioxane (9.379 mL) was heated to 100° C. for 1 hr. The mixture was concentrated, and the residue was purified via Biotage (0-10% EtOAc/heptane; SNAP50 column) giving the title compound 2c (466 mg, 59%) as beige solid. $^1$H NMR (400 MHz, CDCl$_3$) δ ppm 1.33 (s, 12H) 7.53 (dd, J=8.53, 1.58 Hz, 1H) 7.80 (d, J=8.27 Hz, 1H) 7.83-7.92 (m, 2H) 8.15 (s, 1H) 8.32 (s, 1H).

Step 4: 6-(4-(1-hydroxyethyl)pyridin-3-yl)-2-naphthonitrile (2)

A mixture of 6-(4,4,5,5-tetramethyl-1,3,2-dioxaborolan-2-yl)-2-naphthonitrile 2c (233 mg, 0.835 mmol), 1-(3-bromopyridin-4-yl)ethanol (153 mg, 0.759 mmol, prepared according to the procedure described in *Heterocyles* 1993, 35, 151-169), sodium carbonate (2M in water, 0.759 mL, 1.518 mmol), bis(triphenylphosphine)palladium(II) chloride (26.6 mg, 0.038 mmol) in DMF (3.035 mL) was heated to 100° C. for 1 hr. The mixture was quenched with saturated NaHCO$_3$ solution and extracted with EtOAc twice. The combined extracts were dried over anhydrous magnesium sulfate, filtered, and concentrated. The residue was purified twice via Biotage (20-100% EtOAc/heptane; 25M column). 47 mg of racemic title compound was isolated as white solid, and was subsequently separated by chiral HPLC (ChiralPak AS-H column, 2.1×250 mm, 16 mL/min, 70% heptane 30% ethanol) to 2-(enantiomer-1) (13 mg, 6%) (retention time: 11.74 min) and 2-(enantiomer-2) (12 mg, 6%) (retention time: 19.90 min). $^1$H NMR (400 MHz, CDCl$_3$) δ ppm 1.34 (d, J=6.3 Hz, 3H), 5.28 (q, J=6.5 Hz, 1H), 7.59 (d, J=8.3 Hz, 1H), 7.75 (d, J=7.9 Hz, 1H), 7.91 (s, 1H), 8.39 (d, J=5.0 Hz, 1H), 8.55 (s, 1H), 8.70 (d, J=6.2 Hz, 1H). LC-MS (M+1) 275.1, t=1.06 min.

Example 3

Synthesis of 1-(3-(benzofuran-2-yl)pyridin-4-yl)ethanol

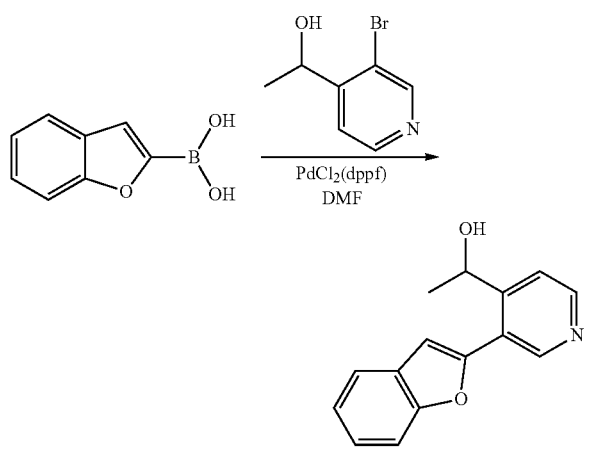

A mixture of benzofuran-2-boronic acid (178 mg, 1.100 mmol), 1-(3-bromopyridin-4-yl)ethanol (202 mg, 1 mmol), sodium carbonate 2N in water (1 mL, 2.000 mmol), PdCl$_2$(dppf).CH$_2$Cl$_2$ adduct (40.8 mg, 0.050 mmol) in DMF (5 mL) was heated to 100° C. for 3 hrs. The mixture was quenched with saturated NaHCO$_3$ solution and extracted with EtOAc two times, dried over magnesium sulfate, filtered, concentrated. The residue was purified via Biotage (25M column, 20-60% EtOAc/heptane, v/v) giving the title compound (56 mg, 23%) as yellow oil. $^1$H NMR (400 MHz, CDCl$_3$) δ ppm 1.56 (d, J=6.4 Hz, 3H), 5.53 (q, J=6.4 Hz, 1H), 7.03 (d, J=0.7 Hz, 1H), 7.31 (td, J=7.3, 0.9 Hz, 1H), 7.38 (td, J=8.0, 1.2 Hz, 1H), 7.54 (dd, J=8.2, 0.7 Hz, 1H), 7.66 (dd, J=7.6, 0.6 Hz, 1H), 7.85 (d, J=5.4 Hz, 1H), 8.63 (bs, 1H), 8.91 (bs, 1H). LC-MS (M+1) 240.2, t=1.25 min.

Example 4

Synthesis of 1-(3-fluoro-5-(6-methoxynaphthalen-2-yl)pyridin-4-yl)ethanol

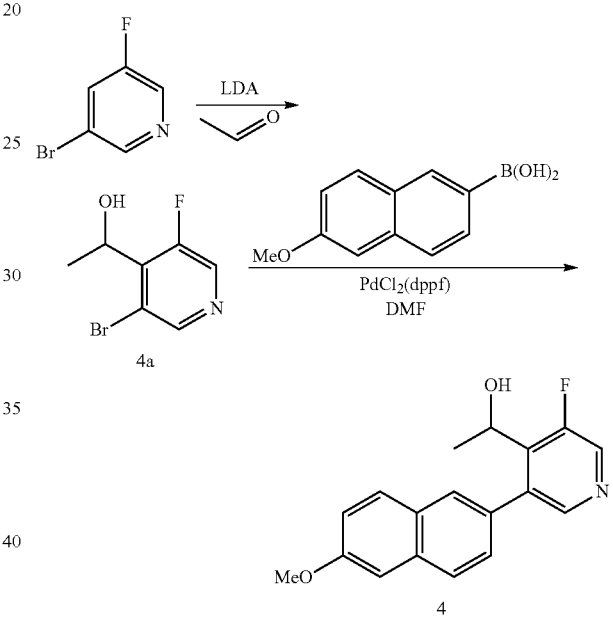

Step 1: 1-(3-bromo-5-fluoropyridin-4-yl)ethanol (4a)

n-BuLi (1.6M in hexanes) (19.60 ml, 31.4 mmol) was added dropwise to a solution of diisopropylamine (4.84 ml, 34.0 mmol) in THF (87 ml) at −78° C. under N$_2$. The resulting mixture was warmed up to −40° C. and stirred for 10 min and recoiled to −78° C. 3-bromo-5-fluoropyridine (4.6 g, 26.1 mmol) in 5 mL THF was added dropwise at this temperature. After 30 min, acetaldehyde (2.95 ml, 52.3 mmol) was added dropwise and the resulting mixture was stirred for 30 min at −78° C., and then for another 30 min at 0° C. The mixture was quenched with saturated NH$_4$Cl solution and extracted with EtOAc two times, dried over magnesium sulfate, filtered, concentrated. The residue was purified via Biotage (SNAP50, 0-30% AcOEt/heptane, v/v) giving the title compound 4a (2.869 g, 50%) as yellow oil. LC-MS (M+1) 221.9, t=1.01 min.

Step 2: 1-(3-fluoro-5-(6-methoxynaphthalen-2-yl)pyridin-4-yl)ethanol

A mixture of 6-methoxynaphthalen-2-ylboronic acid (333 mg, 1.650 mmol), 1-(3-bromo-5-fluoropyridin-4-yl)ethanol 4a (330 mg, 1.5 mmol), sodium carbonate (2M in water, 1.5 mL, 3.00 mmol), PdCl$_2$(dppf).CH$_2$Cl$_2$ adduct (61.2 mg, 0.075 mmol) in DMF (6 mL) was heated to 100° C. for 2 hrs. The mixture was quenched with sat NaHCO$_3$ and extracted with EtOAc two times, dried over magnesium sulfate, filtered, concentrated. The residue was purified via Biotage (20-60% EtOAc/heptane; SNAP25 column) giving the title compound (227 mg, 51%) as a white solid. $^1$H NMR (400 MHz, CDCl$_3$) δ ppm 1.62 (dd, J=6.7, 1.0 Hz, 3H), 3.96 (s, 3H), 4.99 (q, J=6.7 Hz, 1H), 7.19-7.26 (m, 2H), 7.36 (dd, J=8.4, 1.7 Hz, 1H), 7.70 (s, 1H), 7.78 (d, J=8.9 Hz, 1H), 7.83 (d, J=8.5 Hz, 1H), 8.40 (s, 1H), 8.48 (d, J=2.7 Hz, 1H). LC-MS (M+1) 298.0, t=1.49 min.

The racemic mixture 4 (220 mg, 0.740 mmol) was separated by chiral HPLC (ChiralPak IA-H, 4 mL/min, 90% heptane 10% ethanol, v/v) giving 4-(enantiomer-1) as white solid (99 mg) (retention time: 3.35 min) and compound 4-(enantiomer-2) as white solid (95 mg) (retention time: 4.78 min).

Example 5

Synthesis of 6-(5-fluoro-4-(1-hydroxyethyl)pyridin-3-yl)-2-naphthonitrile

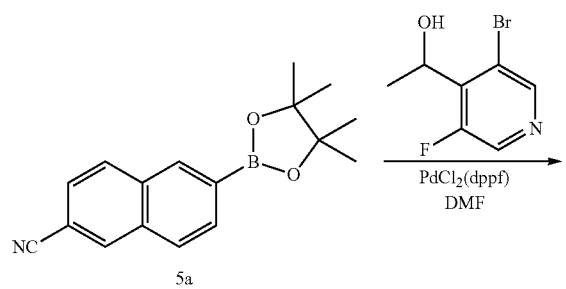

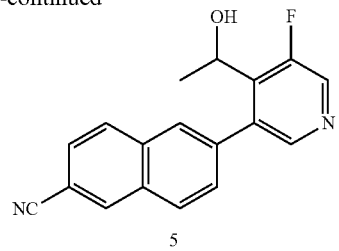

A mixture of 5a (230 mg, 0.824 mmol), 1-(3-bromo-5-fluoropyridin-4-yl)ethanol (199 mg, 0.906 mmol), sodium carbonate (2M in water, 0.824 mL, 1.648 mmol), PdCl$_2$(dppf).CH$_2$Cl$_2$ adduct (33.6 mg, 0.041 mmol) in DMF (3.296 mL) was heated to 100° C. for 3 hrs. The mixture was quenched with sat NaHCO$_3$ and extracted with EtOAc two times, dried over magnesium sulfate, filtered, concentrated. The residue was purified via Biotage (20-60% EtOAc/heptane; 12M column) giving 5 (75 mg, 31%) as white solid. $^1$H NMR (400 MHz, chloroform-d) δ ppm 1.62 (d, J=6.6 Hz, 3H), 4.91 (q, J=6.5 Hz, 1H), 7.56 (d, J=8.1 Hz, 1H), 7.70 (dd, J=8.5, 1.3 Hz, 1H), 7.85 (s, 1H), 7.97-8.02 (m, 2H), 8.31 (s, 1H), 8.39 (s, 1H), 8.53 (s, 1H). LC-MS (M+1) 293.0, t=1.39 min.

The racemic mixture 5 was separated by chiral HPLC (ChiralPak AS-H, 21×250 mm, 14 mL/min, 60% heptane 40% ethanol, v/v) giving 5-(enantriomer-1) as white solid (22 mg) (retention time: 8.44 min) and 5-(enantriomer-2) as white solid (16 mg) (retention time: 14.49 min).

Example 6

Synthesis of 1-(3-fluoro-5-(6-fluoronaphthalen-2-yl)pyridin-4-yl)ethanol

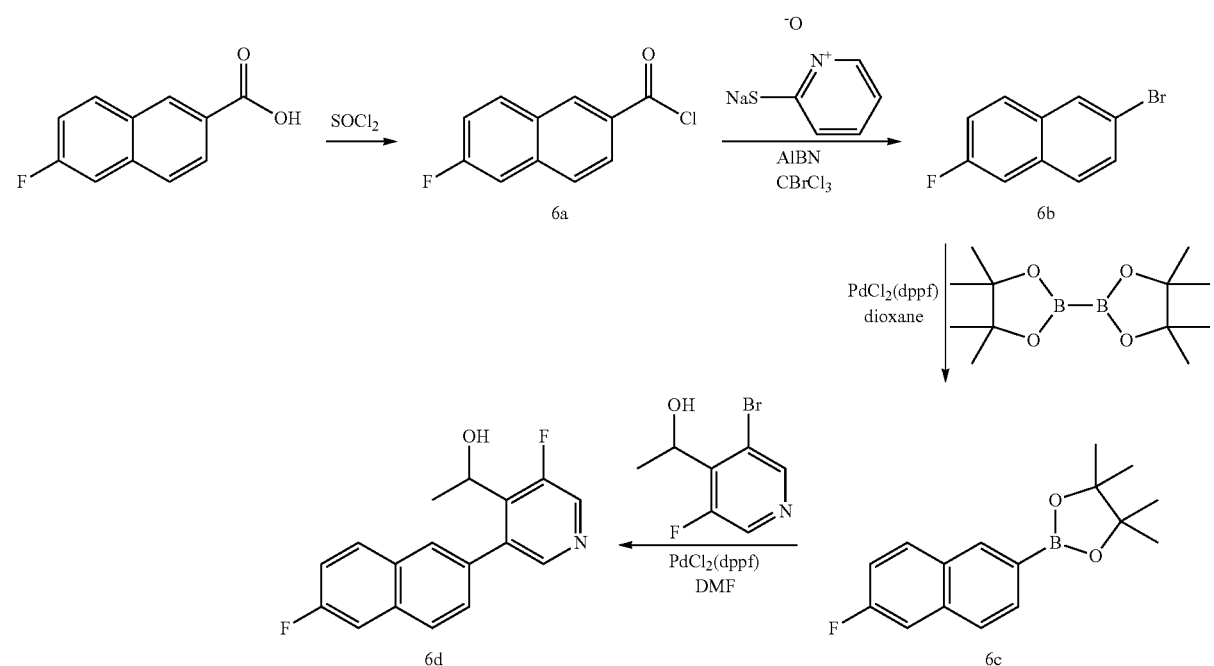

Step 1: 6-fluoro-2-naphthoyl chloride (6a)

6-fluoro-2-naphthoic acid (2 g, 10.52 mmol) was stirred in thionyl chloride (21.03 ml) at 80° C. for 4 h in pressure vessel. The mixture was cooled and concentrated. The acid chloride was dried and used as is for next step.

Step 2: 2-bromo-6-fluoronaphthalene (6b)

6-fluoro-2-naphthoyl chloride (472 mg, 2.097 mmol, 39.9% yield) was combined with AIBN (173 mg, 1.052 mmol) in $CBrCl_3$ (10 mL). That mixture was added slowly to a mixture of 2-Mercaptopyridine N-oxide sodium salt (981 mg, 6.58 mmol) and $CBrCl_3$ (10 mL) at 100° C. over 30 min. After the completion of addition, the mixture was stirred for another 15 min, then cooled. The mixture was quenched with $H_2O$ and extracted with EtOAc two times, dried over magnesium sulfate, filtered, concentrated. The residue was purified via Biotage (0-5% EtOAc/heptane; SNAP25 column) giving 6b (472 mg, 40%) as white solid. $^1$H NMR (400 MHz, MeOD) δ ppm 7.34 (td, J=8.84, 2.59 Hz, 1H) 7.49-7.57 (m, 1H) 7.60 (ddd, J=8.78, 1.96, 0.69 Hz, 1H) 7.77 (d, J=8.84 Hz, 1H) 7.87 (dd, J=9.09, 5.56 Hz, 1H) 8.09 (d, J=1.58 Hz, 1H).

Step 3: 2-(6-fluoronaphthalen-2-yl)-4,4,5,5-tetramethyl-1,3,2-dioxaborolane (6c)

The compound 6c (430 mg, 75%) was obtained as a white solid following the procedure described above for the synthesis of example 1 (step 1).

Step 4: 1-(3-fluoro-5-(6-fluoronaphthalen-2-yl)pyridin-4-yl)ethanol (6d)

The compound 6d (272 mg, 60%) was obtained as a white solid following the procedure described in Example 5. $^1$H NMR (400 MHz, $CD_3OD$) δ ppm 1.56 (dd, J=6.8, 1.2 Hz, 3H), 4.91 (q, J=6.7 Hz, 1H), 7.40 (td, J=8.8, 2.6 Hz, 1H), 7.52 (d, J=8.4 Hz, 1H), 7.62 (dd, J=8.4, 2.6 Hz, 1H), 7.90 (s, 1H), 8.02-7.96 (m, 2H), 8.33 (s, 1H), 8.47 (d, J=3.0 Hz, 1H). LC-MS (M+1) 286.1, t=1.50 min.

The racemic mixture 6 (262 mg, 0.918 mmol) was separated by HPLC (ChiralPak AS-H, 21×250 mm, 90% heptane 10% ethanol, v/v) giving 6-(enantiomer-1) as white solid (93 mg) (retention time: 5.36 min) and 6-(enantiomer-2) as white solid (78 mg) (retention time: 6.63 min).

Example 7

Synthesis of 2-(5-fluoro-4-(1-hydroxyethyl)pyridin-3-yl)benzofuran-6-carbonitrile (17)

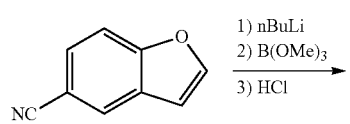

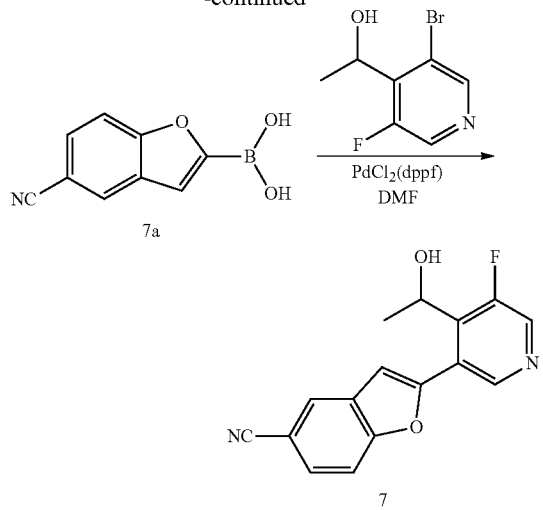

Step 1: 5-cyanobenzofuran-2-ylboronic acid (7a)

To benzofuran-5-carbonitrile (500 mg, 3.49 mmol) in THF (9.98 mL) at −78° C. was added n-BuLi 1.6M in hexanes (2.401 mL, 3.84 mmol) dropwise. The mixture was stirred for 30 min at this temperature, and then trimethyl borate (0.858 mL, 7.68 mmol) was added dropwise. The mixture was stirred for 20 min, and then HCl (2M, 11.52 mL, 23.05 mmol) was added. The bath was removed, and then stirred for 30 min. To the mixture was added more water and extracted with EtOAc three times, dried over magnesium sulfate, filtered, concentrated. crude 7a (623 mg, 87%) was then dried and used as is for next step.

Step 2: 2-(5-fluoro-4-(1-hydroxyethyl)pyridin-3-yl)benzofuran-5-carbonitrile (7)

The compound 7 (243 mg, 43% was obtained as a white solid following the procedure described in Example 5). $^1$H NMR (400 MHz, $CD_3OD$) δ ppm 1.70 (d, J=6.6 Hz, 3H), 5.28 (q, J=6.7 Hz, 1H), 7.29 (s, 1H), 7.70-7.78 (m, 2H), 8.15 (s, 1H), 8.53 (s, 1H), 8.65 (s, 1H). LC-MS (M+1) 283.0, t=1.38 min.

The racemic mixture 7 (220 mg, 0.779 mmol) was separated by HPLC (ChiralPak AS-H, 21×250 mm, 90% heptane 10% ethanol, v/v) giving (S)-2-(5-fluoro-4-(1-hydroxyethyl)pyridin-3-yl)benzofuran-5-carbonitrile 7-(enantiomer-1) as white solid (72 mg) (retention time: 10.93 min) and (R)-2-(5-fluoro-4-(1-hydroxyethyl)pyridin-3-yl)benzofuran-5-carbonitrile 7-(enantiomer-2) as white solid (66 mg) (retention time: 12.57 min).

Example 8

Synthesis of 1-(3-(6-chlorobenzofuran-2-yl)-5-fluoropyridin-4-yl)ethanol

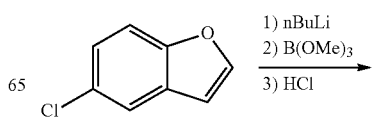

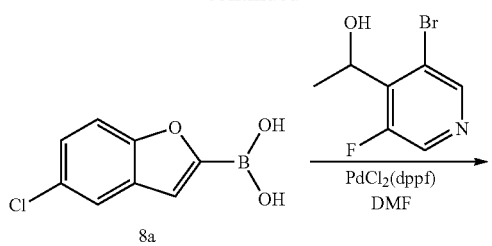

Step 1: 5-chlorobenzofuran-2-ylboronic acid (8a)

The compound 8a (1.427 g, 86%) was obtained as a beige solid following the procedure described in Example 7, step 1.

Step 2: 1-(3-(5-chlorobenzofuran-2-yl)-5-fluoropyridin-4-yl)ethanol (8)

The compound 8a (234 mg, 47%) was obtained as a white solid following the procedure described in example 5. $^1$H NMR (400 MHz, CD$_3$OD) δ ppm 1.70 (dd, J=6.7, 1.1 Hz, 3H), 5.30 (q, J=6.7 Hz, 1H), 7.17 (d, J=0.9 Hz, 1H), 7.36 (dd, J=8.7, 2.2 Hz, 1H), 7.57 (d, J=8.8 Hz, 1H), 7.71 (d, J=2.3 Hz, 1H), 8.52 (d, J=2.8 Hz, 1H), 8.65 (s, 1H). LC-MS (M+1) 292.0, t=1.63 min. The racemic mixture 8 (225 mg, 0.771 mmol) was separated by chiral HPLC (ChiralPak AS-H, 21×250 mm, 90% heptane 10% ethanol, v/v) giving 8-(enantiomer-1) as white solid (71 mg) (retention time: 11.64 min) and 8-(enantiomer-2) as white solid (56 mg) (retention time: 17.65 min).

Example 9

Synthesis of 4-(5-fluoro-4-(1-hydroxyethyl)pyridin-3-yl)-2-methylbenzonitrile

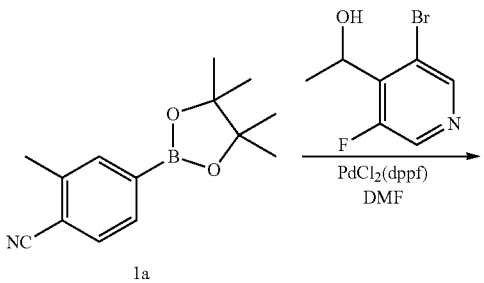

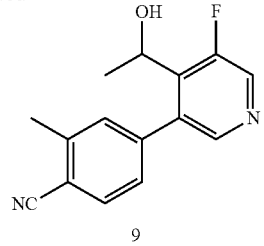

The racemic 9 (220 mg, 51%) was obtained as a white solid following the procedure described in example 5. $^1$H NMR (400 MHz, CD$_3$OD) δppm: 1.52 (dd, J=6.6, 0.7 Hz, 3H), 2.60 (s, 3H), 4.80-4.83 (m, 1H), 7.34-7.37 (m, 1H), 7.44-7.45 (m, 1H), 7.78 (d, J=7.9 Hz, 1H), 8.22 (s, 1H), 8.47 (d, J=2.9 Hz, 1H). LC-MS (M+1) 257.1, t=1.33 min.

The racemic mixture (220 mg, 0.858 mmol) was separated by chiral HPLC (ChiralPak IA-H, 4 ml/min, 60% heptane 40% ethanol, v/v) giving 9-(enantiomer-1) as white solid (39 mg) (retention time: 6.05 min) and 9-(enantiomer-2) as white solid (52 mg) (retention time: 10.23 min).

Example 10

Synthesis of 4-(5-fluoro-4-(2-hydroxypropan-2-yl)pyridin-3-yl)-2-methylbenzonitrile Step 1: 2-(3-bromo-5-fluoropyridin-4-yl)propan-2-ol (10a)

n-BuLi 1.6M in hexanes (11.25 ml, 18.00 mmol) was added dropwise to a solution of diisopropylamine (2.78 ml, 19.50 mmol) in THF (50.0 ml) at −78° C. under N$_2$. The resulting mixture was warmed up to −40° C. and stirred for 10 min and recooled to −78° C. 3-bromo-5-fluoropyridine (2.64 g, 15 mmol) in 5 mL THF was added dropwise at this temperature. After 30 min, acetone (3.30 ml, 45.0 mmol) was added dropwise and the resulting mixture was stirred for 30 min at −78° C., and then for another 30 min at 0° C. The mixture was quenched with saturated NH₄Cl and extracted with EtOAc two times, dried over magnesium sulfate, filtered, concentrated. The residue was purified via Biotage (0-30% AcOEt/heptane, SNAP50) giving 10a (1.691 g, 48%) as a yellow oil. LC-MS (M+1) 235.9, t=1.18 min.

Step 2: 4-(5-fluoro-4-(2-hydroxypropan-2-yl)pyridin-3-yl)-2-methylbenzonitrile (10)

The title compound (80 mg, 25%) was obtained as a white solid following the procedure described in example 5. ¹H NMR (400 MHz, CD₃OD) δ ppm: 1.61 (d, J=2.0 Hz, 6H), 2.55 (s, 3H), 7.22 (d, J=7.9 Hz, 1H), 7.30 (s, 1H), 7.62 (d, J=7.8 Hz, 1H), 8.02 (s, 1H), 8.40 (d, J=3.8 Hz, 1H). LC-MS (M+1) 271.1, t=1.45 min.

Example 11

Synthesis of 2-(4-acetyl-5-fluoropyridin-3-yl)benzofuran-5-carbonitrile

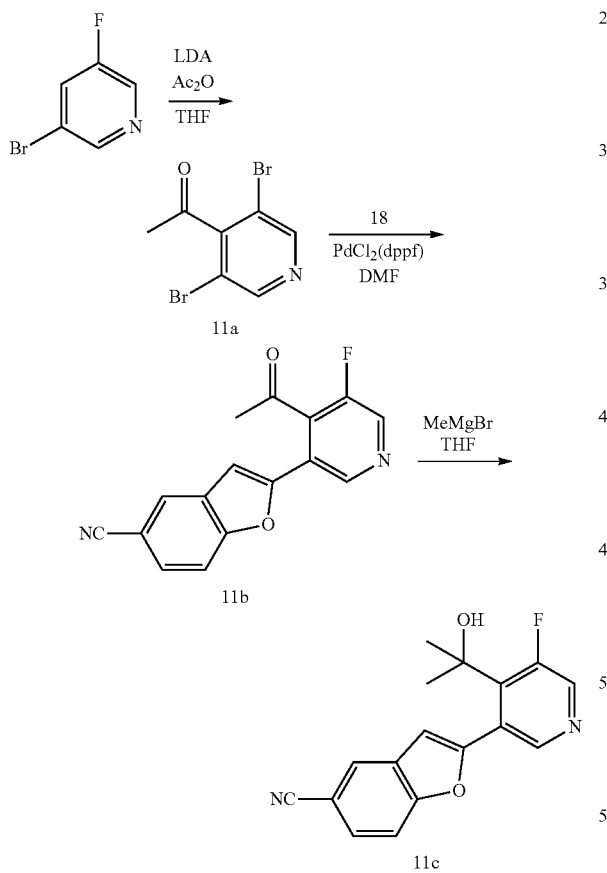

Step 1: 1-(3-bromo-5-fluoropyridin-4-yl)ethanone (11a)

The compound 11a (1.356 g, 42%) was obtained as a yellow oil following the procedure described in Example 10, step 1, but using acetic anhydride instead of acetone. LC-MS (M+1) 219.9, t=1.22 min.

Step 2: 2-(4-acetyl-5-fluoropyridin-3-yl)benzofuran-5-carbonitrile (11b)

The compound 11b (75 mg, 27%) was obtained as a white solid following the procedure described in example 5. ¹H NMR (400 MHz, CD₃OD) δ ppm 2.65 (d, J=0.9 Hz, 3H), 7.45 (s, 1H), 7.72 (s, 1H), 7.73 (s, 1H), 8.15 (d, J=1.3 Hz, 1H), 8.63 (s, 1H), 8.99 (s, 1H). LC-MS (M+1) 281.1, t=1.49 min.

Step 3: 2-(5-fluoro-4-(2-hydroxypropan-2-yl)pyridin-3-yl)benzofuran-5-carbonitrile (11)

To 2-(4-acetyl-5-fluoropyridin-3-yl)benzofuran-5-carbonitrile 11b (200 mg, 0.714 mmol) in THF (3.57 mL) at −78° C. was added methylmagnesium bromide (3M in Et₂O, 0.714 mL, 2.142 mmol). The mixture was stirred for 1 hr at −78° C., and then for 1 hr at 0° C. The mixture was quenched with saturated NH₄Cl and extracted with EtOAc two times, dried over magnesium sulfate, filtered and concentrated. The residue was purified via Biotage (10-40% EtOAc/heptane; SNAP25 column), and then purified on Waters mass directed preparative-HPLC (ACN—H₂O—NR₄OH, Xbridge Preparation C18 column, 30×100 mm) giving the title compound 11 (60 mg, 28%). ¹H NMR (400 MHz, MeOD) δ ppm 1.70 (d, J=1.96 Hz, 6H) 6.94 (s, 1H) 7.55-7.71 (m, 2H) 8.00-8.11 (m, 1H) 8.39 (s, 1H) 8.53 (d, J=3.73 Hz, 1H). LC-MS (M+1) 297.1, t=1.50 min.

Example 12

Synthesis of 6-(6-fluoro-4-(2-hydroxypropan-2-yl)pyridin-3-yl)-2-naphthonitrile (26)

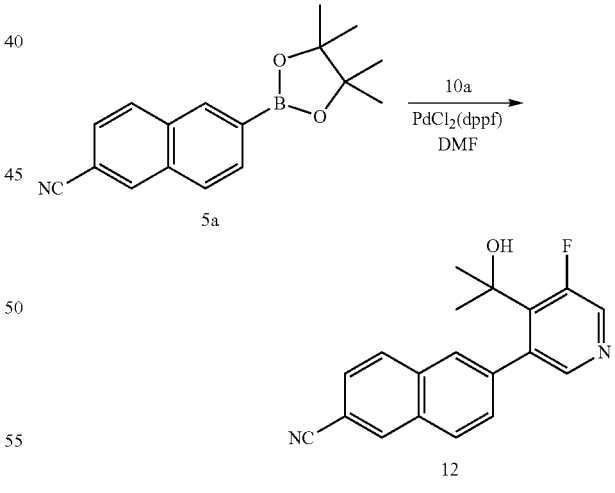

The compound 12 (113 mg, 30%) was prepared from the coupling of 2-(3-bromo-5-fluoropyridin-4-yl)propan-2-ol (described in example 10) and 5a as described in Example 5. Compound 12 was obtained as a white solid. ¹H NMR (400 MHz, MeOD) δ ppm 1.63 (br. s., 6H) 7.58 (dd, J=8.49, 1.74 Hz, 1H) 7.69 (dd, J=8.53, 1.64 Hz, 1H) 7.82 (s, 1H) 7.95 (d, J=8.65 Hz, 1H) 8.04 (d, J=8.72 Hz, 1H) 8.12 (s, 1H) 8.40 (d, J=0.76 Hz, 1H) 8.42 (d, J=3.92 Hz, 1H). LC-MS (M+1) 307.2, t=1.53 min.

Example 13

Synthesis of 1-(3-(5-chloro-6-fluorobenzofuran-2-yl)-5-fluoropyridin-4-yl)ethanol (30) and 1-(3-(5-chloro-4-fluorobenzofuran-2-yl)-5-fluoropyridin-4-yl)ethanol

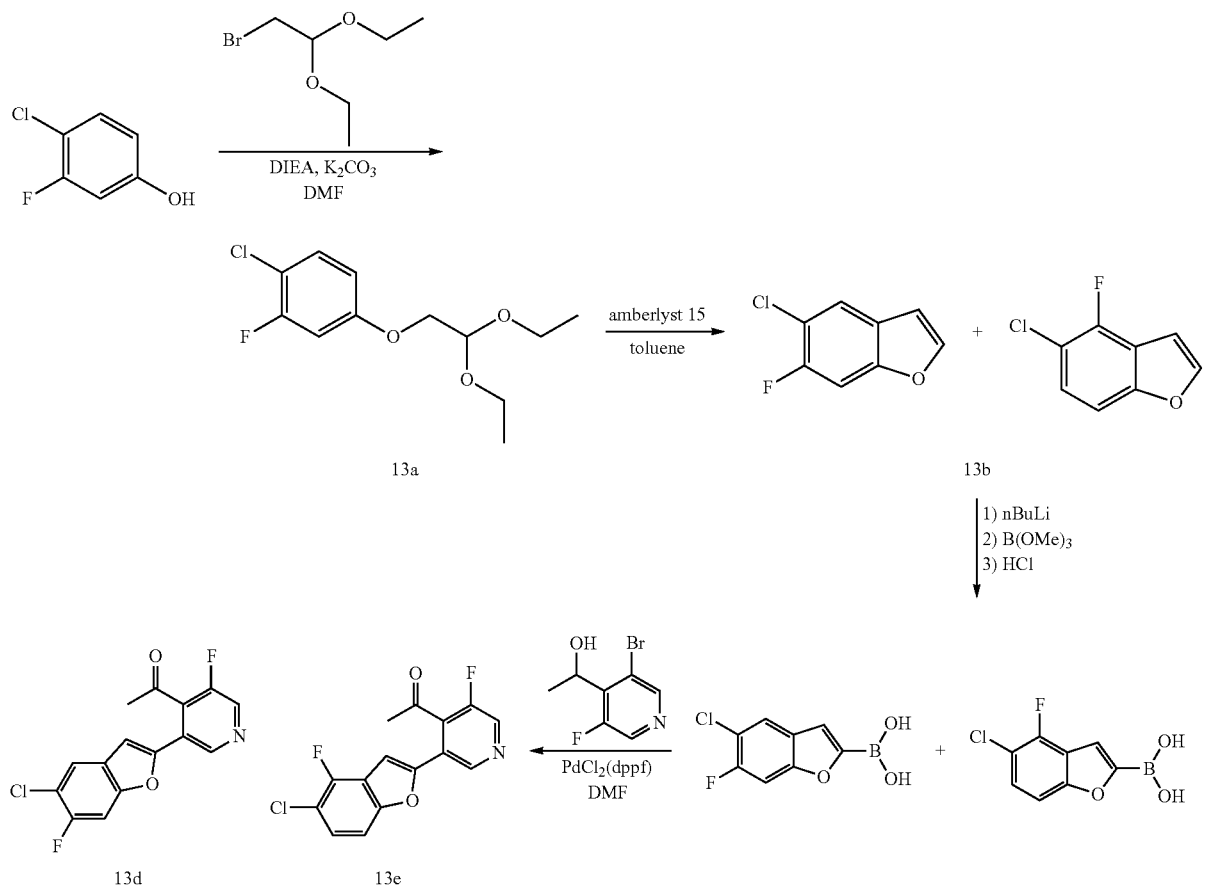

13a

13b 13d  13e

Step 1: 1-chloro-4-(2,2-diethoxyethoxy)-2-fluorobenzene (13a)

To 4-chloro-3-fluorophenol (3.66 g, 25 mmol) in DMF (30 ml) at room temperature was added potassium carbonate (6.91 g, 50.0 mmol), DIEA (8.73 ml, 50.0 mmol) and then bromoacetaldehyde diethylacetal (7.52 ml, 50.0 mmol). The mixture was stirred at 100° C. for 16 hr. The mixture was cooled to room temperature and then quenched with water and extracted with EtOAc two times, dried over magnesium sulfate, filtered, concentrated. The residue was purified via Biotage (0-20% AcOEt/heptane; SNAP25 column) giving 13a (6.87 g, quant) as a colorless oil.

Step 2: 5-chloro-6-fluorobenzofuran+5-chloro-4-fluorobenzofuran (13b)

To 13a (3.44 g, 13.09 mmol) in toluene (13.09 ml) at room temperature was added amberlyst 15 (700 mg, 13.09 mmol). The mixture was stirred at 200° C. for 10 min in microwave. The mixture was cooled to room temperature and then the solvent was concentrated. The residue was purified via Biotage (heptane; SNAP25 column) giving 13b (505 mg, 23%) as a colorless oil. $^1$H NMR of major isomer in mixture (400 MHz, MeOD) δ ppm 6.84 (dd, J=2.27, 0.95 Hz, 1H) 7.46 (dd, J=9.16, 0.95 Hz, 1H) 7.71 (d, J=7.39 Hz, 1H) 7.81 (d, J=2.27 Hz, 1H).

Step 3: 5-chloro-6-fluorobenzofuran-2-ylboronic acid and 5-chloro-4-fluorobenzofuran-2-ylboronic acid (13c)

The mixture 13c was obtained as crude and used as is following the procedure described in example 8, step 1.

Step 4: 1-(3-(5-chloro-6-fluorobenzofuran-2-yl)-5-fluoropyridin-4-yl)ethanol (13d) and 1-(3-(5-chloro-4-fluorobenzofuran-2-yl)-5-fluoropyridin-4-yl)ethanol (13e)

The compound 13d (63 mg, 12%) and compound 13e (26 mg, 5%) were obtained as white solid following the procedure described in example 5. Compound 13d: LC-MS (M+1) 310.0, t=1.65 min. $^1$H NMR (400 MHz, MeOD) δ ppm 1.69 (dd, J=6.76, 0.95 Hz, 3H) 5.27 (q, J=6.63 Hz, 1H) 7.30 (s, 1H) 7.35-7.52 (m, 2H) 8.53 (d, J=2.78 Hz, 1H) 8.65 (s, 1H). Compound 13e: LC-MS (M+1) 310.0, t=1.63 min. $^1$H NMR (400 MHz, MeOD) δ ppm 1.69 (dd, J=6.76, 0.82 Hz, 3H) 5.27 (q, J=7.01 Hz, 1H) 7.17 (d, J=0.69 Hz, 1H) 7.58 (d, J=8.53 Hz, 1H) 7.81 (d, J=7.33 Hz, 1H) 8.50 (d, J=2.84 Hz, 1H) 8.62 (s, 1H).

The racemic mixture 13d (59 mg, 0.191 mmol) was separated (ChiralPak AD-H, 21×250 mm, 18 mL/min, 70% heptane 30% ethanol, v/v) giving 13d-(enantiomer-1) as white solid (7 mg) (retention time: 6.85 min) and 13d-(enantiomer-2) as white solid (12 mg) (retention time: 10.11 min).

The racemic mixture 13e (21 mg, 0.068 mmol) was separated by HPLC (ChiralPak AD-H, 21×250 mm, 18 mL/min, 60% heptane 40% ethanol, v/v) giving 13e-(enantiomer-1) as white solid (6.9 mg) (retention time: 8.43 min) and 13e-(enantiomer-2) as white solid (5.8 mg) (retention time: 12.45 min).

Example 14

Synthesis of 4-[4-(1-Hydroxy-ethyl)-pyridin-3-yl]-2-methoxy-benzonitrile

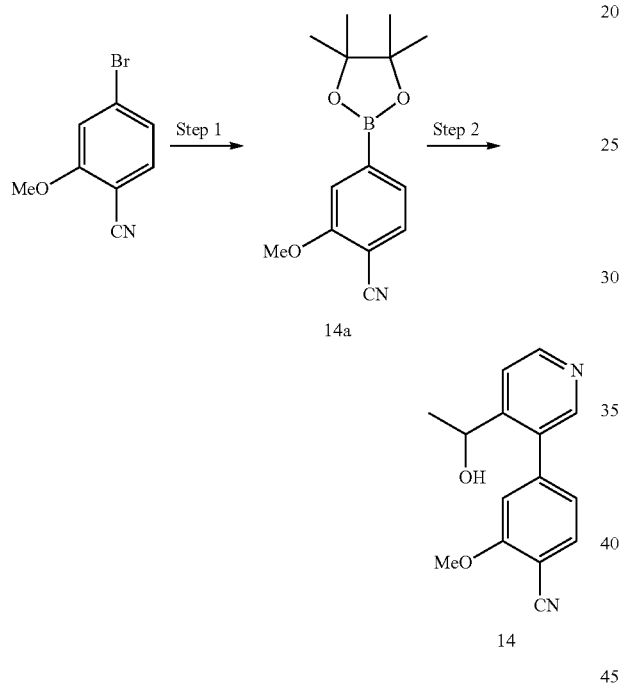

Step 1: 2-Methoxy-4-(4,4,5,5-tetramethyl-[1,3,2]dioxaborolan-2-yl)-benzonitrile (14a)

A mixture of 4-Bromo-2-methoxy-benzonitrile (1 g, 4.72 mmol), 4,4,4',4',5,5,5',5'-octamethyl-2,2'-bi(1,3,2-dioxaborolane) (1.198 g, 4.72 mmol), potassium acetate (0.926 g, 9.43 mmol) and PdCl$_2$(dppf).CH$_2$Cl$_2$ adduct (0.193 g, 0.236 mmol) in 1,4-Dioxane (10 mL, dry) was heated to 80° C. for 5 hrs. The mixture was concentrated, and the residue was purified by ISCO column (Ethyl Acetate-Heptane, v/v, 10%-20%) and yielded the title compound as colorless solid (850 mg). $^1$H NMR (400.3 MHz, CDCl$_3$): δ 1.35 (s, 12H), 3.97 (s, 3H), 7.35 (s, 1H), 7.54 (d, J=7.5 Hz, 1H), 7.42 (d, J=7.5 Hz, 1H).

Step 2: 4-[4-(1-Hydroxy-ethyl)-pyridin-3-yl]-2-methoxy-benzonitrile (14)

To the solution of 2-methoxy-4-(4,4,5,5-tetramethyl-1,3,2-dioxaborolan-2-yl)benzonitrile (3.53 g, 13.61 mmol), 1-(3-bromopyridin-4-yl)ethanol (2.50 g, 12.37 mmol) and PdCl$_2$(dppf).CH$_2$Cl$_2$ adduct (505 mg, 0.62 mmol) in DMF (60 mL) was added 2M Na$_2$CO$_3$ solution (12.3 ml, 24.6 mmol) under Nitrogen atmosphere. The mixture was stirred and heated at 100° C. for 4 hrs. After letting cool to room temperature, solvent was removed in vacuo. The resulting residue was dissolved in DCM and saturated NH$_4$Cl solution. After extraction and separation, the extracts were concentrated and purified by ISCO 40 g (10% MeOH/DCM=0-25%) to give 4-(4-(1-hydroxyethyl)pyridin-3-yl)-2-methoxybenzonitrile (2.1 g, 67%) as a white solid; ESI-MS m/z: 255 [M+1]$^+$, Retention time 1.24 min. $^1$H-NMR (MeOD, 400 MHz) δ 1.36 (d, J=6.4 Hz, 3H), 3.98 (s, 3H), 4.88 (q, J=6.4 Hz, 1H), 7.06 (dd, J=8.0, 1.2 Hz, 1H), 7.18 (s, 1H), 7.71 (d, J=5.2 Hz, 1H), 7.73 (d, J=1.2 Hz, 1H), 8.36 (s, 1H), 8.58 (d, J=5.2 Hz, 1H). The racemate was separated by HPLC (ChiralPak IA-H, 5% MeOH/5% EtOH/Heptane) to give 4-[4-((R)-1-Hydroxy-ethyl)-pyridin-3-yl]-2-methoxy-benzonitrile 14-(enantiomer-1) retention time: 16.18 min) and 4-[4-((S)-1-Hydroxy-ethyl)-pyridin-3-yl]-2-methoxy-benzonitrile 14-(enantiomer-2), retention time: 19.07 min).

Example 15

Synthesis of 2-Chloro-4-(5-fluoro-4-hydroxymethyl-pyridin-3-yl)-benzonitrile

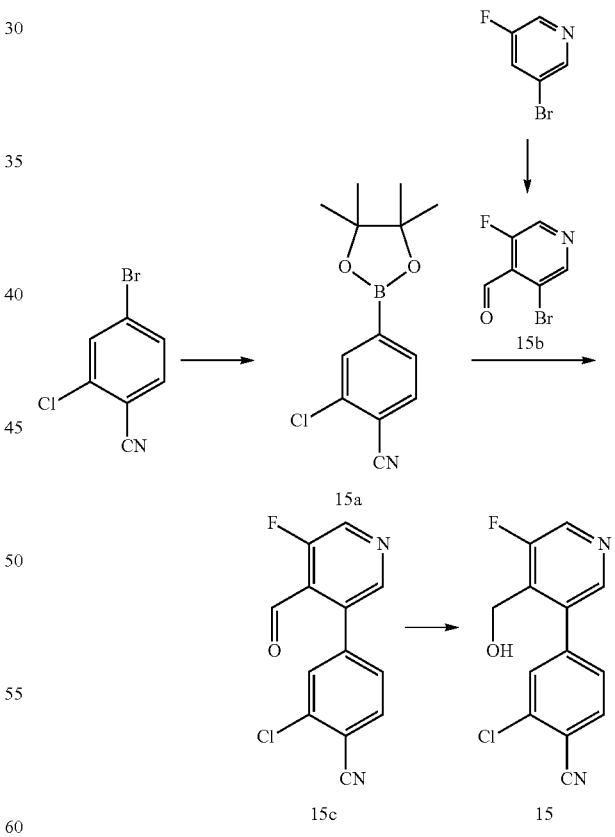

Step 1: 2-chloro-4-(4,4,5,5-tetramethyl-1,3,2-dioxaborolan-2-yl)benzonitrile (15a)

A mixture of 4-bromo-2-chlorobenzonitrile (15 g, 69.3 mmol), 4,4,4',4',5,5,5',5'-octamethyl-2,2'-bi(1,3,2-dioxaborolane) (17.60 g, 69.3 mmol), potassium acetate (13.60 g, 139 mmol) and PdCl₂(dppf).CH₂Cl₂ adduct (2.83 g, 3.46 mmol) in 1,4-dioxane (100 mL) was heated to 80° C. for 4.5 hr. After filtration and concentration, the residue was dissolved into CH₂Cl₂ and mixed with celite. After concentration, the residue was loaded to column (120 g ISCO) and flushed with ethyl acetate/heptane (v/v, 0%-5%) and resulted colorless solid 16.4 g. ¹H NMR (400.3 MHz, CDCl₃): δ 1.35 (s, 12H), 7.61 (d, J=7.6 Hz, 1H), 7.70 (d, J=7.6 Hz, 1H), 7.87 (s, 1H).

Step 2: 3-Bromo-5-fluoro-pyridine-4-carbaldehyde (15b)

n-BuLi (13.85 mL, 22.16 mmol) was added to a solution of diisopropylamine (3.16 mL, 22.16 mmol) in THF (50 mL) at −78° C. After 30 min, 3-bromo-5-fluoropyridine (3.0 g, 17.05 mmol) in THF (25 mL) was added dropwise. The mixture was stirred for 1 hr, and then DMF (3.96 mL, 51.1 mmol) was added dropwise. Saturated aqueous NaHCO₃ was added and the cooling bath was removed. The mixture was shaken with ethyl acetate and the organic phase was washed with brine, dried over MgSO₄, and concentrated in vacuo. The residue was purified by silica gel flash chromatography employing dichloromethane-methanol, 9:1 to give 3-fluoro-5-(1-oxo-1, 3-dihydro-isobenzofuran-5-yl)-pyridine-4-carbaldehyde. ¹H NMR (400 MHz, DMSO-d₆) δ ppm 8.81 (d, J=1.4 Hz, 1H), 8.83 (s, 1H), 10.17 (s, 1H)

Step 3: 2-Chloro-4-(5-fluoro-4-formyl-pyridin-3-yl)-benzonitrile (15c)

To the solution of 2-chloro-4-(4,4,5,5-tetramethyl-1,3,2-dioxaborolan-2-yl)benzonitrile (264 mg, 1.00 mmol), 3-bromo-5-fluoroisonicotinaldehyde (204 mg, 1.00 mmol) and PdCl₂(PPh₃)₂ (56 mg, 0.08 mmol) in DMF (3 mL) was added 2M Na₂CO₃ solution (1.50 ml, 3.00 mmol) under nitrogen atmosphere. The mixture was stirred and heated at 100° C. for 4 hrs. After letting cool to room temperature, solvent was removed in vacuo. The resulting residue was dissolved in DCM and saturated NH₄Cl solution. After extraction and separation, the combined extracts were concentrated and purified by SNAP10 g (10% MeOH/DCM 0-15% gradient) to give 2-chloro-4-(5-fluoro-4-formylpyridin-3-yl)benzonitrile (47 mg, 18%) as a white solid; ESI-MS m/z: 293 [M+MeOH+1]⁺, Retention time 1.15 min. ¹H-NMR (CDCl₃, 400 MHz) δ 7.33 (dd, J=8.0, 1.6 Hz, 1H), 7.50 (d, J=1.6 Hz, 1H), 7.78 (d, J=8.0 Hz, 1H), 8.49 (s, 1H), 8.78 (d, J=1.2 Hz, 1H), 10.27 (s, 1H).

Step 4: 2-Chloro-4-(5-fluoro-4-hydroxymethyl-pyridin-3-yl)-benzonitrile (15)

To the solution of 2-chloro-4-(5-fluoro-4-formylpyridin-3-yl)benzonitrile (45 mg, 0.17 mmol) in THF (3 mL) and water (1 mL) was added sodium borohydride (6.5 mg, 0.17 mmol) at 0° C. This reaction mixture was stirred for 0.5 h at room temperature. After addition of CH₂Cl₂, the organic layer was washed with saturated NaCl solution and extracted with DCM for five times. The combined extracts were dried over Na₂SO₄, filtered, and evaporated. The resulting mixture was passed through a pad of silica gel, rinsed with 0-50% EtOAc/heptane, and evaporated to give 2-Chloro-4-(5-fluoro-4-hydroxymethyl-pyridin-3-yl)-benzonitrile (21 mg, 46%) as a white solid. ESI-MS m/z: 263 [M+1]⁺, Retention time 1.11 min. 1H-NMR (CDCl₃, 400 MHz) δ 4.56 (s, 2H), 7.66 (dd, J=8.4, 1.6 Hz, 1H), 7.88 (d, J=1.6 Hz, 1H), 7.93 (d, J=8.4 Hz, 1H), 8.39 (s, 1H), 8.55 (s, 1H).

Example 16

2-Chloro-4-[5-fluoro-4-(1-hydroxy-ethyl)-pyridin-3-yl]-benzonitrile

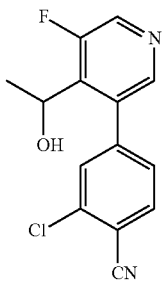 [SMILES: CC(O)c1c(F)cncc1-c1ccc(C#N)c(Cl)c1]

To the solution of 2-Chloro-4-(4,4,5,5-tetramethyl-[1,3,2] dioxaborolan-2-yl)-benzonitrile (263 mg, 1.00 mmol), 1-(3-Bromo-5-Fluoro-pyridin-4-yl)-ethanol (220 mg, 1.00 mmol) and PdCl₂(dppf). CH₂Cl₂ adduct (65 mg, 0.08 mmol) in DMF (4 mL) was added 2M Na₂CO₃ solution (1.50 ml, 3.00 mmol) under nitrogen atmosphere. The mixture was stirred and heated at 100° C. for 4 hrs. After letting cool to room temperature, solvent was removed in vacuo. The resulting residue was dissolved in DCM and sat. NH₄Cl solution. After extraction with DCM, the combined extracts were concentrated and purified by ISCO 12 g (0-30% EtOAc/Hep) to give 2-Chloro-4-[5-fluoro-4-(1-hydroxy-ethyl)-pyridin-3-yl]-benzonitrile (138 mg, 49%) as a white solid; ESI-MS m/z: 276 [M+1]⁺, Retention time 1.15 min. ¹H-NMR (CDCl₃, 400 MHz) δ 1.53 (d, J=6.8 Hz, 3H), 4.76 (q, J=6.8 Hz, 1H), 7.28 (dd, J=8.0, 2.0 Hz, 1H), 7.45 (d, J=2.0 Hz, 1H), 7.71 (d, J=8.0 Hz, 1H), 8.20 (s, 1H), 8.46 (d, J=2.0 Hz, 1H). The racemate was separated by chiral HPLC (ChiralPak IA-H, 40% EtOH/Heptane, v/v) and yielded 2-Chloro-4-[5-fluoro-4-((R)-1-hydroxy-ethyl)-pyridin-3-yl]-benzonitrile 16-(enantiomer-1) (retention time: 5.24 min) and 2-Chloro-4-[5-fluoro-4-((S)-1-hydroxy-ethyl)-pyridin-3-yl]-benzonitrile 16-(enantiomer-2) (retention time: 13.69 min).

Example 17

Synthesis of 2-Methoxy-4-[5-fluoro-4-(1-hydroxy-ethyl)-pyridin-3-yl]-benzonitrile

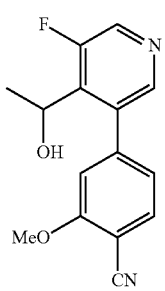

To the solution of 2-Methoxy-4-(4,4,5,5-tetramethyl-[1,3,2]dioxaborolan-2-yl)-benzonitrile (259 mg, 1.00 mmol), 1-(3-Bromo-5-Fluoro-pyridin-4-yl)-ethanol (220 mg, 1.00 mmol) and PdCl$_2$(dpPf). CH$_2$Cl$_2$ adduct (65 mg, 0.08 mmol) in DMF (4 mL) was added 2M Na$_2$CO$_3$ solution (1.50 ml, 3.00 mmol) under Nitrogen atmosphere. The mixture was stirred and heated at 100° C. for 4 hrs. After letting cool to room temperature, solvent was removed in vacuo. The resulting residue was dissolved in DCM and sat. NH$_4$Cl solution. After extraction with DCM and separation, the combined extracts were concentrated and purified by ISCO 12 g (0-30% EtOAc/Heptane, v/v) to give 2-Methoxy-4-[5-fluoro-4-(1-hydroxy-ethyl)-pyridin-3-yl]-benzonitrile (142 mg, 52%) as a white solid; ESI-MS m/z: 273 [M+1]$^+$, Retention time 1.09 min. $^1$H-NMR (CDCl$_3$, 400 MHz) δ 1.61 (d, J=6.8 Hz, 3H), 3.96 (s, 3H), 4.83 (q, J=6.8 Hz, 1H), 6.93 (d, J=1.2 Hz, 1H), 6.95 (dd, J=8.0, 1.2 Hz, 1H), 7.65 (d, J=8.0 Hz, 1H), 8.29 (s, 1H), 8.51 (d, J=2.8 Hz, 1H)

The racemate was separated by HPLC (ChiralPak IA-H, 40% EtOH/Heptane, v/v), and gave 17-(enantiomer-1) (retention time: 4.56 min, 17-(enantiomer-2) (retention time: 7.16 min).

Example 18

Synthesis of 4-[4-(1-Hydroxy-ethyl)-pyridin-3-yl]-benzonitrile

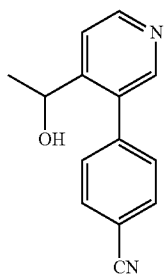 [SMILES: CC(O)c1ccncc1-c1ccc(C#N)cc1]

To the solution of 4-cyano phenylboronic acid (220 mg, 1.50 mmol), 1-(3-Bromo-pyridin-4-yl)-ethanol (303 mg, 1.50 mmol) and PdCl$_2$(dppf). CH$_2$Cl$_2$ adduct (98 mg, 0.12 mmol) in DMF (6 mL) was added 2M Na$_2$CO$_3$ solution (1.50 ml, 3.00 mmol) under Nitrogen atmosphere. The mixture was stirred and heated at 100° C. for 4 hrs. After letting cool to room temperature, solvent was removed in vacuo. The resulting residue was dissolved in DCM and sat. NH$_4$Cl solution. After extraction with DCM and separation, the combined extracts were concentrated and purified by ISCO 12 g (10% MeOH/DCM=0-25%) to give 4-[4-(1-Hydroxy-ethyl)-pyridin-3-yl]-benzonitrile (18, 170 mg, 51%) as a white solid; ESI-MS m/z 225 [M+H]$^+$, Retention time 0.97 min. $^1$H-NMR (MeOD, 400 MHz) δ 1.28 (d, J=6.4 Hz, 3H), 4.85 (q, J=6.4 Hz, 1H), 7.56 (d, J=8.4 Hz, 2H), 7.73 (d, J=5.2 Hz, 1H), 7.86 (d, J=8.4 Hz, 2H), 8.33 (s, 1H), 8.59 (d, J=5.2 Hz, 1H)

The racemate was separated by chiral HPLC (ChiralPak IA-H, 40% EtOH/Heptane, v/v) and gave 18-(enantiomer-1) (retention time: 9.84 min) and 18-(enantiomer-2) (retention time: 11.33 min).

Example 19

Synthesis of 2-Fluoro-4-[4-(1-hydroxy-ethyl)-pyridin-3-yl]-benzonitrile

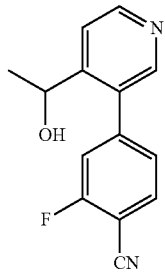 [SMILES: CC(O)c1ccncc1-c1ccc(C#N)c(F)c1]

To the solution of 4-cyano-3-fluoro phenylboronic acid (247 mg, 1.50 mmol), 1-(3-Bromo-pyridin-4-yl)-ethanol (303 mg, 1.50 mmol) and PdCl$_2$(dppf). CH$_2$Cl$_2$ adduct (98 mg, 0.12 mmol) in DMF (6 mL) was added 2M Na$_2$CO$_3$aq (1.50 ml, 3.00 mmol) under Nitrogen atmosphere. The mixture was stirred and heated at 100° C. for 4 hrs. After letting cool to room temperature, solvent was removed in vacuo. The resulting residue was dissolved in DCM and saturated NH$_4$Cl solution. After extraction with DCM and separation, the combined extracts were concentrated and purified by ISCO 12 g (10% MeOH/DCM=0-25%) to give 2-Fluoro-4-[4-(1-hydroxy-ethyl)-pyridin-3-yl]-benzonitrile (190 mg, 52%) as colorless solid; ESI-MS m/z: 243 [M+1]$^+$, Retention time 1.05 min $^1$H-NMR (MeOD, 400 MHz) δ 1.29 (d, J=6.4 Hz, 3H), 4.85 (q, J=6.4 Hz, 1H), 7.38 (dd, J=8.0, 1.6 Hz, 1H), 7.45 (dd, J=10.0, 1.6 Hz, 1H), 7.73 (d, J=5.6 Hz, 1H), 7.88 (t, J=8.0 Hz, 1H), 8.35 (s, 1H), 8.61 (d, J=5.6 Hz, 1H).

The racemate was separated by chiral HPLC (ChiralPak IA-H, 40% EtOH/Heptane, v/v) and gave 19-(enantiomer-1) (retention time: 9.69 min) and 19-(enantiomer-2) (retention time: 11.51 min).

Example 20

Synthesis of 2-chloro-4-(4-(1-hydroxyethyl)pyridin-3-yl)benzonitrile

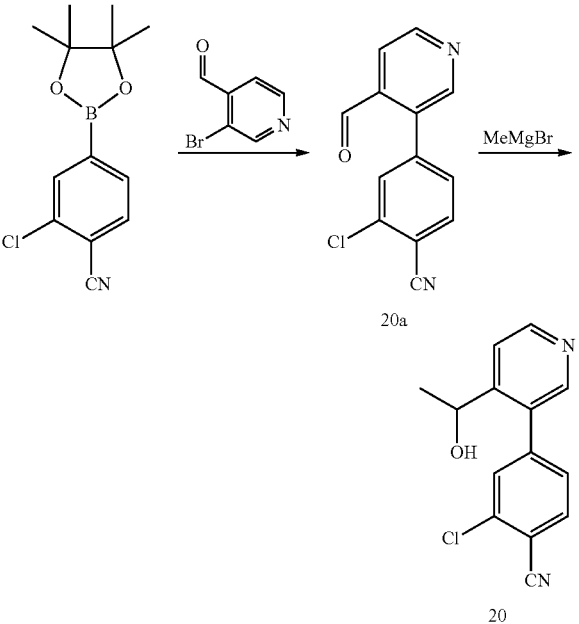

Step 1: 2-chloro-4-(4-formylpyridin-3-yl)benzonitrile (20a)

A mixture of 2-Chloro-4-(4,4,5,5-tetramethyl-[1,3,2]dioxaborolan-2-yl)-benzonitrile (0.264 g, 1 mmol), 3-bromoisonicotinaldehyde (0.186 g, 1.000 mmol), sodium carbonate (1.000 ml, 2.000 mmol), bis(triphenylphosphine)palladium (II) chloride (0.018 g, 0.025 mmol) in DMF (6 mL, dry) was heated to 120° C. for 3 hrs. After concentration, the residue was dissolved into $CH_2Cl_2$-MeOH and mixed with silica gel and concentrated. After flash column (MeOH—$CH_2Cl_2$, v/v, 0.5%-1%) yielded 2-chloro-4-(4-formylpyridin-3-yl)benzonitrile (20a) as colorless solid (170 mg) $^1$H NMR (400.3 MHz, $CDCl_3$): δ 7.63 (d, J=8.0 Hz, 1H), 7.79 (s, 1H), 7.83 (d, J=8.0 Hz, 1H), 8.35 (s, 1H), 9.07 (s, 1H), 9.15 (s, 1H), 10.22 (s, 1H).

Step 2: 2-chloro-4-(4-(1-hydroxyethyl)pyridin-3-yl)benzonitrile (20)

A solution of methylmagnesium bromide (519 μl, 1.558 mmol) was added dropwise to a solution of 2-chloro-4-(4-formylpyridin-3-yl)benzonitrile (126 mg, 0.519 mmol) in dry THF (15 mL) at −50° C. The resulting mixture was slowly warmed up to 0° C. during 2 hr. The reaction was quenched by $NH_4Cl$ (solution). After extraction with $CH_2Cl_2$, dry over $Na_2SO_4$, filtration, concentration again, the residue was purified by column ($CH_2Cl_2$-MeOH, v/v, 1-3.5%) and yielded 120 mg of 2-chloro-4-(4-(1-hydroxyethyl)pyridin-3-yl)benzonitrile. ESI-MS m/z: 259 [M+1]$^+$, Retention time 1.11 min; $^1$H-NMR (MeOD, 400 MHz) δ 1.29 (d, J=6.4 Hz, 3H), 4.83 (q, J=6.4 Hz, 1H), 7.50 (dd, J=8.0, 1.6 Hz, 1H), 7.71 (d, J=1.6 Hz, 1H), 7.73 (d, J=5.6 Hz, 1H), 7.92 (d, J=8.0 Hz, 1H), 8.35 (s, 1H), 8.61 (d, J=5.6 Hz, 1H).

The racemate was separated by HPLC (ChiralPak IA-H, 30% EtOH/Heptane v/v) and gave 20-(enantiomer-1) (retention time: 6.47 min) and 20-(enantiomer-2) (retention time: 12.24 min).

Example 21

Synthesis of 3-Fluoro-4-[4-(1-hydroxy-ethyl)-pyridin-3-yl]-benzonitrile

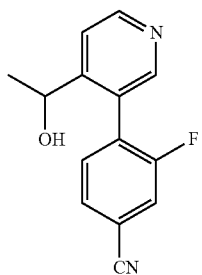 [SMILES: CC(O)c1ccncc1-c1ccc(C#N)cc1F]

To the solution of 3-Fluoro-4-(4,4,5,5-tetramethyl-[1,3,2]dioxaborolan-2-yl)-benzonitrile (306 mg, 1.24 mmol), 1-(3-Bromo-pyridin-4-yl)-ethanol (250 mg, 1.24 mmol) and $PdCl_2$(dppf).$CH_2Cl_2$ adduct (81 mg, 0.10 mmol) in DMF (6 mL) was added 2M $Na_2CO_3$ solution (1.55 ml, 3.09 mmol) under Nitrogen atmosphere. The mixture was stirred and heated at 100° C. for 4 hrs. After letting cool to room temperature, solvent was removed in vacuo. The resulting residue was dissolved in DCM and saturated $NH_4Cl$ solution. After extraction with DCM and separation, the combined extracts were concentrated and purified by ISCO 12 g (10% MeOH/DCM=0-25%) to give 3-Fluoro-4-[4-(1-hydroxy-ethyl)-pyridin-3-yl]-benzonitrile (35 mg, 11%) as colorless solid; ESI-MS m/z: 243 [M+1]$^+$, Retention time 1.19 min. $^1$H-NMR (MeOD, 400 MHz) δ 1.26 (d, J=6.8 Hz, 3H), 4.71 (q, J=6.8 Hz, 1H), 7.55 (t, J=8.0 Hz, 1H), 7.71 (dd, J=8.0, 1.6 Hz, 1H), 7.74 (d, J=9.6 Hz, 1H), 7.75 (d, J=5.2 Hz, 1H), 8.33 (s, 1H), 8.62 (d, J=5.2 Hz, 1H).

Example 22

Synthesis of 2-Chloro-4-(5-chloro-4-hydroxymethyl-pyridin-3-yl)-benzonitrile

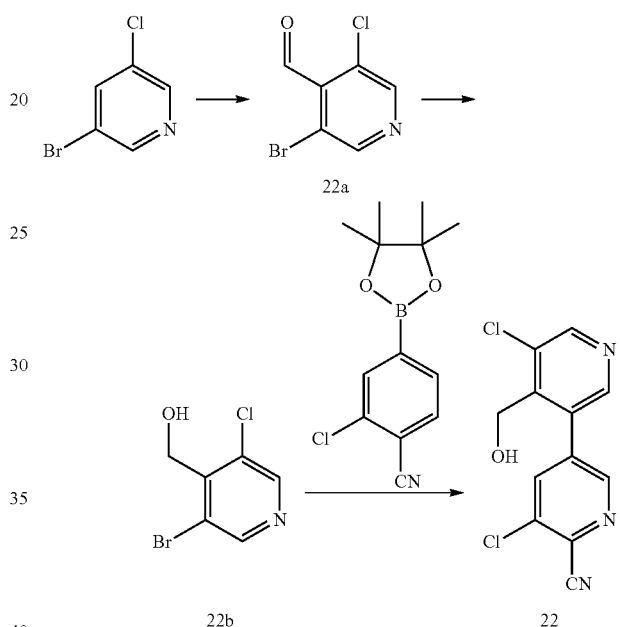

Step 1: 3-Bromo-5-chloro-pyridine-4-carbaldehyde (22a)

n-BuLi (11.25 mL, 1.6 M, 18 mmol) was added dropwise to a solution of diisopropylamine (2.78 mL, 19.5 mmol) in THF (60 mL) at −78° C. under $N_2$. The resulting mixture was warmed up to −40° C. and stirred for 10 min and recooled to −78° C. A solution of 3-bromo-5-chloropyridine (2.89 g, 15 mmol) in THF was added dropwise at this temperature. After 30 min, DMF was added dropwise and the resulting mixture was stirred for another 30 min. the reaction was quenched with saturated $NH_4Cl$ solution, and warmed up to room temperature. After concentration, the residue was dissolved in EtOAc and washed with saturated $NaHCO_3$ solution. After drying over $Na_2SO_4$, filtration and concentration, the residue was purified by ISCO (40 g) column (0-30% EtOAc/Heptane) to give slightly yellow crystal (1.91 g). ESI-MS m/z: 253.8 [M+1+MeOH]$^+$, Retention time 1.07 min. $^1$H-NMR ($CDCl_3$, 400 MHz) δ 8.65 (s, 1H), 8.76 (s, 1H), 10.32 (s, 1H).

Step 2: (3-Bromo-5-chloro-pyridin-4-yl)methanol (22b)

To the solution of 3-Bromo-5-chloro-pyridine-4-carbaldehyde (270 mg, 1.23 mmol) in THF (5 mL) and water (1 mL)

was added NaBH₄ (139 mg, 3.67 mmol). The resulting mixture was stirred for another 1 h, and was diluted with DCM. The organic layer was washed with water and brine. The aqueous layer was extracted with DCM. The combined extracts were separated and concentrated in vacuo to give 270 mg of title compound without further purification. ESI-MS m/z: 223.9 [M+1]⁺, Retention time 1.01 min. ¹H-NMR (CDCl₃, 400 MHz) δ 4.88 (s, 2H), 8.46 (s, 1H), 8.56 (s, 1H).

Step 3: 2-Chloro-4-(5-chloro-4-hydroxymethyl-pyridin-3-yl)-benzonitrile (22)

To the solution of 2-Chloro-4-(4,4,5,5-tetramethyl-[1,3,2]dioxaborolan-2-yl)-benzonitrile (320 mg, 1.21 mmol), (3-Bromo-5-chloro-pyridin-4-yl)-methanol (220 mg, 1.21 mmol) and PdCl₂(dppf).CH₂Cl₂ adduct (79 mg, 0.09 mmol) in DMF (4 mL) was added 2M Na₂CO₃ solution (1.82 ml, 3.64 mmol) under Nitrogen atmosphere. The mixture was stirred and heated at 100° C. for 4 hrs. After letting cool to room temperature, solvent was removed in vacuo. The resulting residue was dissolved in DCM and saturated NH₄Cl solution. After extraction with DCM and separation, the combined extracts were concentrated and purified by ISCO 12 g (0-30% EtOAc/Hep) to give 2-Chloro-4-(5-chloro-4-hydroxymethyl-pyridin-3-yl)-benzonitrile (142 mg, 52%) as colorless solid; ESI-MS m/z: 279 [M+1]⁺, Retention time 1.41 min. ¹H-NMR (CDCl₃, 400 MHz) δ 4.66 (s, 2H), 7.53 (d, J=8.0 Hz, 1H), 7.69 (s, 1H), 7.81 (d, J=8.0 Hz, 1H), 8.47 (s, 1H), 8.72 (s, 1H).

Example 23

Synthesis of 2-Chloro-4-[5-chloro-4-(1-hydroxy-ethyl)-pyridin-3-yl]-benzonitrile

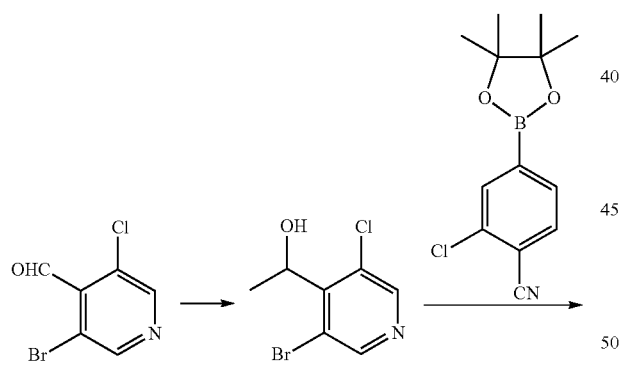

Step 1: 1-(3-Bromo-5-chloro-pyridin-4-yl)-ethanol (23a)

To a solution of 3-Bromo-5-chloro-pyridine-4-carbaldehyde (440 mg, 2 mmol) in THF (8 mL) was added methylmagnesium bromide (3M solution in THF, 2 mL, 6 mmol) at −36° C. After 1 h, the resulting mixture was warmed to 0° C., and saturated NH₄Cl solution was added. The mixture was extracted with ethyl acetate, and washed with brine. The combined extracts were separated, dried over MgSO₄ and concentrated. The residue was passed though a pad of silica gel and eluted with EtOAc/Heptane (v/v, 1:1). After concentration, 370 mg of title compound was obtained without further purification. ESI-MS m/z: 237.8 [M+1]⁺, Retention time 1.20 min. ¹H-NMR (CDCl₃, 400 MHz) δ 1.56 (d, J=6.8 Hz, 3H), 5.43 (q, J=6.8 Hz, 1H), 8.40 (1H), 8.52 (s, 1H).

Step 2: 2-Chloro-4-[5-chloro-4-(1-hydroxy-ethyl)-pyridin-3-yl]-benzonitrile (23)

To the solution of 2-Chloro-4-(4,4,5,5-tetramethyl-[1,3,2]dioxaborolan-2-yl)-benzonitrile (412 mg, 1.56 mmol), 1-(3-Bromo-5-chloro-pyridin-4-yl)-ethanol (370 mg, 1.56 mmol) and PdCl₂(dppf).CH₂Cl₂ adduct (64 mg, 0.08 mmol) in DMF (10 mL) was added 2M Na₂CO₃ solution (2.35 ml, 4.70 mmol) under Nitrogen atmosphere. The mixture was stirred and heated at 100° C. for 4 hrs. After letting cool to room temperature, solvent was removed in vacuo. The resulting residue was dissolved in DCM and saturated NH₄Cl solution. After extraction with DCM and separation, the combined extracts were concentrated and purified by ISCO 12 g (0-30%, EtOAc/Heptane, v/v) to give 2-Chloro-4-[5-chloro-4-(1-hydroxy-ethyl)-pyridin-3-yl]-benzonitrile (150 mg, 33%) as colorless solid; ESI-MS m/z: 293 [M+H]⁺, Retention time 1.46 min ¹H-NMR (CDCl₃, 400 MHz) δ 1.58 (d, J=6.8 Hz, 3H), 5.07 (q, J=6.8 Hz, 1H), 7.34 (dd, J=8.0, 1.6 Hz, 1H), 7.50 (d, J=1.6 Hz, 1H), 7.77 (d, J=8.0 Hz, 1H), 8.29 (s, 1H), 8.64 (s, 1H).

The racemate was separated by chiral HPLC (ChiralPak AS-H, 5% MeOH/5% EtOH/Heptane, v/v/v) to give 23-(enantiomer-1) (retention time: 10.22 min) and 23-(enantiomer-2) (retention time: 13.73 min).

Example 24

Synthesis of 2-chloro-4-(1-methyl-3-oxo-1,3-dihydrofuro[3,4-c]pyridin-7-yl)benzonitrile

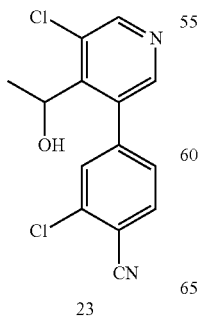

23

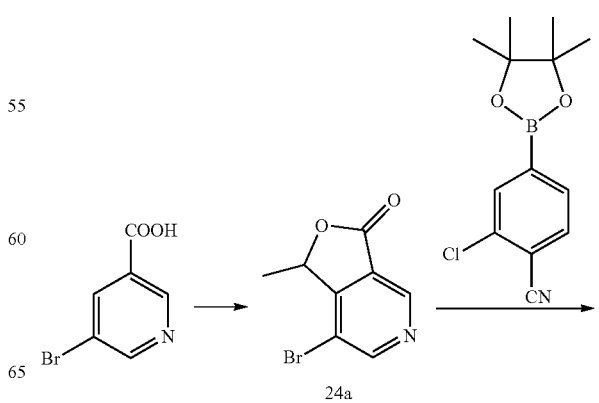

24a

Example 25

Synthesis of 4-[5-Chloro-4-(1-hydroxy-ethyl)-pyridin-3-yl]-2-methoxy-benzonitrile

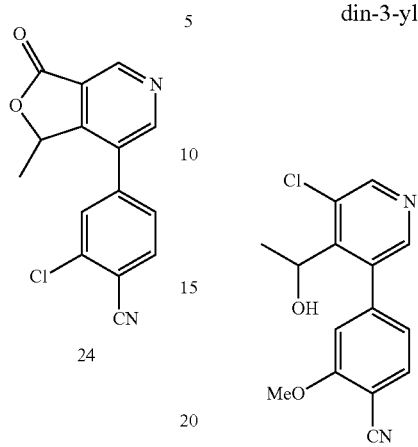

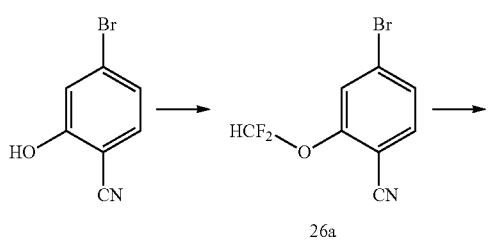

Step 1: 7-bromo-1-methylfuro[3,4-c]pyridin-3(1H)-one (24a)

n-BuLi (1375 µl, 2.200 mmol) was added dropwise to a solution of 2,2,6,6-tetramethylpiperidine (407 µl, 2.400 mmol) in THF (5 mL) at −78° C. under inert gas (N$_2$). The resulting mixture was stirred at ∼−50° C. for 1 hr. 5-bromonicotinic acid (202 mg, 1 mmol) in THF (5 mL) was added at this temperature. The resulting mixture was stirred for 45 min at −50° C. acetaldehyde (56.5 µl, 1.000 mmol) was added and the resulting mixture was stirred for 60 min. The reaction was quenched by NH$_4$Cl (saturated solution) and warmed up to room temperature. After acidified to pH 2 with HCl, the resulting mixture was heated to reflux for 8 hrs. After concentration, acid-base extraction and concentration again, the residue was purified by column (Heptane/ethyl acetate v/v, 10-20%) yielded colorless solid. $^1$H NMR (400.3 MHz, CDCl$_3$): δ 1.77 (d, J=6.7 Hz, 3H), 5.56 (q, J=6.7 Hz, 1H), 8.91 (s, 1H), 9.08 (s, 1H).

Step 2: 2-chloro-4-(1-methyl-3-oxo-1,3-dihydrofuro[3,4-c]pyridin-7-yl)benzonitrile (24)

To the solution of 2-chloro-4-(4,4,5,5-tetramethyl-1,3,2-dioxaborolan-2-yl)benzonitrile (116 mg, 0.44 mmol), 7-bromo-1-methylfuro[3,4-c]pyridin-3(1H)-one (100 mg, 0.44 mmol) and PdCl$_2$(dppf).CH$_2$Cl$_2$ (28.6 mg, 0.035 mmol) in DMF (5 mL) was added a solution of Na$_2$CO$_3$ (0.44 mL, 2M) under Nitrogen atmosphere. The mixture was stirred and heated at 100° C. for 4 hrs. The mixture was warmed up room temperature, and solvent was removed in vacuo. The residue was dissolved in DCM and saturated NH$_4$Cl solution. After extraction with DCM and separation, the combined extracts were dried over Na$_2$SO$_4$, filtered and concentrated. The residue was purified by ISCO 40 g (10% MeOH/DCM, v/v, 0-25%) to give 19 mg of the titled compound. ESI-MS m/z: 284.9 [M+1]$^+$, Retention time 1.32 min; $^1$H-NMR (MeOD, 400 MHz) δ 1.31 (d, J=6.8 Hz, 3H), 6.23 (q, J=6.8 Hz, 1H), 7.79 (dd, J=8.0, 1.6 Hz, 1H), 8.01 (d, J=1.6 Hz, 1H), 8.04 (d, J=8.0 Hz, 1H), 8.94 (s, 1H), 9.17 (s, 1H).

To the solution of 2-Methoxy-4-(4,4,5,5-tetramethyl-[1,3,2]dioxaborolan-2-yl)-benzonitrile (570 mg, 2.20 mmol), 1-(3-Bromo-5-chloro-pyridin-4-yl)-ethanol (520 mg, 2.20 mmol) and PdCl$_2$(dppf).CH$_2$Cl$_2$ adduct (65 mg, 0.08 mmol) in DMF (10 mL) was added Na$_2$CO$_3$ solution (2M in eater, 2.75 ml, 5.50 mmol) under Nitrogen atmosphere. The mixture was stirred and heated at 100° C. for 6 hrs. After letting cool to room temperature, solvent was removed in vacuo. The residue was dissolved in DCM and saturated NH$_4$Cl solution. After extraction with DCM and separation, the combined extracts were concentrated and purified by ISCO 40 g (10% MeOH/DCM, v/v, 0-25%) to give 4-[5-Chloro-4-(1-hydroxy-ethyl)-pyridin-3-yl]-2-methoxy-benzonitrile (320 mg, 50%) as colorless solid; ESI-MS m/z: 289 [M+1]$^+$, Retention time: 1.30 min; $^1$H-NMR (MeOD, 400 MHz) δ 1.55 (d, J=6.8 Hz, 3H), 4.01 (s, 3H), 5.13 (q, J=6.8 Hz, 1H), 7.07 (dd, J=8.0, 2.0 Hz, 1H), 7.19 (d, J=2.0 Hz, 1H), 7.73 (d, J=8.0 Hz, 1H), 8.31 (s, 1H), 8.61 (s, 1H).

The racemate was separated by HPLC (ChiralPak AD-H, 15% EtOH/Heptane, v/v) to give 25-(enantiomer-1) (retention time: 1.16 min) and 25-(enantiomer-2) (retention time: 1.76 min).

Example 26

Synthesis of 4-[5-Chloro-4-(1-hydroxy-ethyl)-pyridin-3-yl]-2-difluoromethoxy-benzonitrile

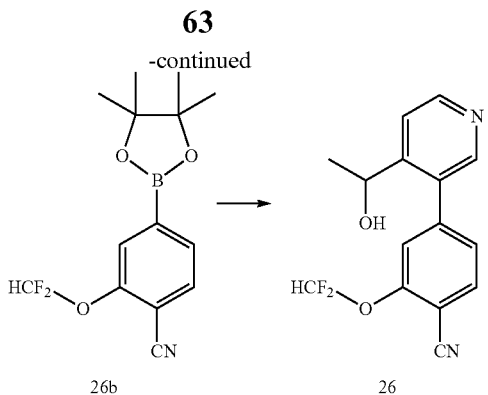

Step 1: 4-Bromo-2-difluoromethoxy-benzonitrile (26a)

To a solution of 4-bromo-2-hydroxybenzonitrile (1.0 g, 5.05 mmol) in DMF (25 mL) was added potassium carbonate (977 mg, 7.07 mmol) at room temperature and the resulting mixture was stirred for 10 min. This solution was bubbling with difluorochloromethane gas at room temperature for 30 min. This mixture was subsequently heated to 80° C. and turned brown after additional 2 h. After letting cool to room temperature, reaction mixture was filtered through a pad of Celite and rinsed with EtOAc and concentrated in vacuo. The residue was purified by ISCO 40 g column (0-10% EtOAc/Hep) to give 4-bromo-2-(difluoromethoxy)benzonitrile (780 mg, 63%) as a pale yellow crystal; ESI-MS m/z: 247 [M+1]$^+$, Retention time 1.49 min

Step 2: 2-Difluoromethoxy-4-(4,4,5,5-tetramethyl-[1,3,2]dioxaborolan-2-yl)-benzonitrile (26b)

The solution of 4-bromo-2-(difluoromethoxy)benzonitrile (780 mg, 3.14 mmol), bis(pinacolato)diboron (1198 mg, 4.72 mmol), potassium acetate (617 mg, 6.29 mmol) and PdCl$_2$(dppf).CH$_2$Cl$_2$ adduct (257 mg, 0.31 mmol) in 1,4-dioxane (9 mL) was stirred for 5 hrs at 80° C. under Nitrogen atmosphere. After letting cool to room temperature, the resulting solution was extracted with ethyl acetate The combined extracts were washed with water, dried over Na$_2$SO$_4$ and filtered. The filtrate was concentrated in vacuo. The crude material was purified by ISCO 12 g silica column eluting with 0-20% ethyl acetate in heptane to give 1.13 g of the title compound mixed with pinacolato borane (~6:1, $^1$H-NMR). $^1$H-NMR (CDCl$_3$, 400 MHz) δ 1.27 (s, 12H), 6.68 (t, J=72.4 Hz, 1H), 7.66 (d, J=7.6 Hz, 1H), 7.67 (s, 1H), 7.72 (d, J=7.6 Hz, 1H).

Step 3: 4-[5-Chloro-4-(1-hydroxy-ethyl)-pyridin-3-yl]-2-difluoromethoxy-benzonitrile (26)

To the solution of 2-difluoromethoxy-4-(4,4,5,5-tetramethyl-[1,3,2]dioxaborolan-2-yl)-benzonitrile (927 mg, 3.14 mmol), 1-(3-Bromo-pyridin-4-yl)-ethanol (634 mg, 3.14 mmol) and PdCl$_2$(dppf).CH$_2$Cl$_2$ adduct (256 mg, 0.31 mmol) in DMF (12 mL) was added a solution of Na$_2$CO$_3$ (2M, 3.14 ml, 6.28 mmol) under Nitrogen atmosphere. The mixture was stirred and heated at 100° C. for 6 hrs. After letting cool to room temperature, solvent was removed in vacuo. The resulting residue was dissolved in DCM and saturated NH$_4$Cl solution. After extraction with DCM and separation, the combined extracts were concentrated and the residue was purified by ISCO 40 g (EtOAc/Heptane, v/v, 0-90%) to give 4-[5-Chloro-4-(1-hydroxy-ethyl)-pyridin-3-yl]-2-difluoromethoxy-benzonitrile (290 mg, 32%) as a white solid; ESI-MS m/z: 291 [M+1]$^+$, Retention time 1.28 min; $^1$H-NMR (CDCl$_3$, 400 MHz) δ 1.41 (d, J=6.8 Hz, 3H), 4.92 (q, J=6.8 Hz, 1H), 6.72 (t, J=71.2 Hz, 1H), 7.31 (dd, J=8.0, 1.2 Hz, 1H), 7.36 (d, J=1.2 Hz, 1H), 7.70 (d, J=5.2 Hz, 1H), 7.79 (d, J=8.0 Hz, 1H), 8.44 (s, 1H), 8.71 (d, J=5.2 Hz, 1H).

The racemate was separated by chiral HPLC (ChiralPak OD-H, 10% EtOH/Heptane) to give 26-(enantiomer-1) (retention time: 1.65 min) and 26-(enantiomer-2) (retention time: 2.14 min).

Example 27

Synthesis of 2-Chloro-4-[5-fluoro-4-(3-hydroxy-oxetan-3-yl)-pyridin-3-yl]-benzonitrile

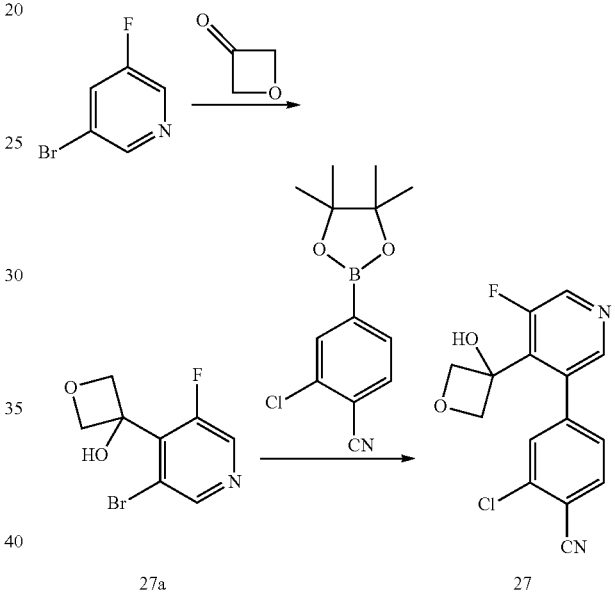

Step 1: 3-(3-Bromo-5-fluoro-pyridin-4-yl)-oxetan-3-ol (27a)

n-BuLi (1.6 M in hexane, 4.26 mL, 6.82 mmol) was added dropwise to a solution of diisopropylamine (1.05 mL, 7.39 mmol) in THF (14 mL) at −78° C. under Nitrogen atmosphere. The resulting mixture was warmed up to −40° C. and stirred for 10 min and recooled to −78° C. A solution of 3-bromo-5-fluoropyridine (1000 mg, 5.68 mmol) in THF (5 mL) was added dropwise at this temperature. After completion of addition, the reaction mixture turned brown. After 30 min, Oxetan-3-one (491 mg, 6.82 mmol) was added dropwise and the resulting mixture was stirred for 30 min at this temperature. The reaction was quenched with saturated NH$_4$Cl solution. The mixture was extracted with ethyl acetate, and the combined extracts were washed with saturated NaHCO$_3$ solution, dried over Na$_2$SO$_4$ and filtered. After concentration, 3-(3-Bromo-5-fluoro-pyridin-4-yl)-oxetan-3-ol (1190 mg, 84%) was obtained as a dark red solid; ESI-MS m/z: 249 [M+1]$^+$, Retention time 0.83 min; $^1$H-NMR (MeOD, 400 MHz) δ 4.77 (d, J=8.8 Hz, 2H), 5.25 (d, J=8.8 Hz, 1H), 5.26 (d, J=8.8 Hz, 1H), 8.45 (d, J=1.6 Hz, 1H), 8.56 (s, 1H).

Step 2: 2-Chloro-4-[5-fluoro-4-(3-hydroxy-oxetan-3-yl)-pyridin-3-yl]-benzonitrile (27)

To the solution of 2-chloro-4-(4,4,5,5-tetramethyl-1,3,2-dioxaborolan-2-yl)benzonitrile (409 mg, 1.55 mmol), 3-(3-Bromo-5-fluoro-pyridin-4-yl)-oxetan-3-ol (350 mg, 1.41 mmol) and PdCl$_2$(dppf).CH$_2$Cl$_2$ adduct (115 mg, 0.141 mmol) in DMF (7 mL) was added a solution of Na$_2$CO$_3$ (2M in water, 1.76 ml, 3.53 mmol) under Nitrogen atmosphere. The mixture was stirred and heated at 100° C. for 4 hrs. After letting cool to room temperature, solvent was removed in vacuo. The resulting residue was dissolved in DCM and saturated NH$_4$Cl solution. After extraction with DCM and separation, the combined extracts were concentrated and purified by ISCO 12 g (0-40%, v/v, EtOAc/Heptane) to give 2-Chloro-4-[5-fluoro-4-(3-hydroxy-oxetan-3-yl)-pyridin-3-yl]-benzonitrile (26 mg, 6%) as colorless solid; ESI-MS m/z: 305 [M++1]$^+$, Retention time 1.27 min; $^1$H-NMR (CDCl$_3$, 400 MHz) δ 4.42 (d, J=8.4 Hz, 2H), 4.66 (d, J=8.4 Hz, 2H), 7.57 (d, J=6.8 Hz, 1H), 7.76 (s, 1H), 7.80 (d, J=6.8 Hz, 1H), 8.41 (s, 1H), 8.59 (s, 1H).

Example 28

Synthesis of 2-chloro-4-(4-(oxetan-2-yl)pyridin-3-yl) benzonitrile

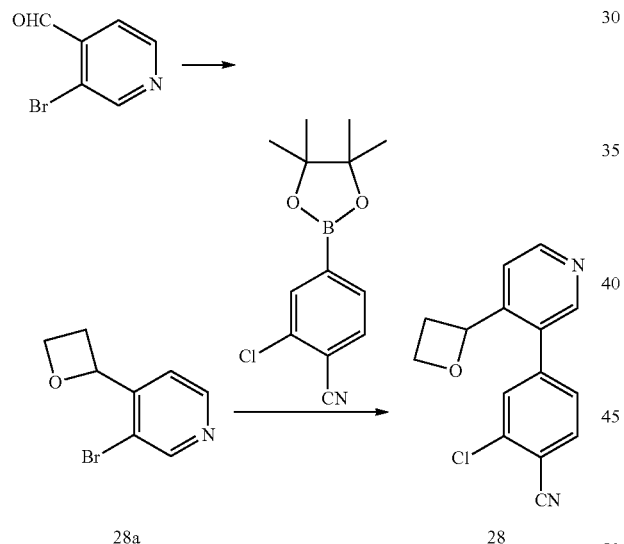

Step 1: 3-bromo-4-(oxetan-2-yl)pyridine (28a)

A 500 mL round-bottomed flask was charged with trimethylsulfoxonium iodide (11.83 g, 53.8 mmol) in DMSO (80 ml). sodium hydride (1.989 g, 49.7 mmol) was added. After stirring for 15 min, a solution of 3-bromoisonicotinaldehyde (5 g, 26.9 mmol) in DMSO (20 ml) was added slowly to the reaction. After 10 min. The reaction mixture was diluted with water and EtOAc. The mixture was washed with H$_2$O and brine. The organic was dried over Na$_2$SO$_4$, filtered and concentrated to give crude intermediate 2.69 g without further purification.

A 100 mL round-bottomed flask was charged with trimethylsulfoxonium iodide (5.92 g, 26.9 mmol) in t-BuOH (20 ml). Potassium tert-butoxide (3.02 g, 26.9 mmol) was added. After stirring for 15 min at 50° C., a solution of the above intermediate (2.69 g) in DMSO (20 ml) was added slowly to the reaction. After 16 h, the reaction mixture was diluted with water and EtOAc. The mixture was extracted with ethyl acetate and washed with H$_2$O and brine to give 462 mg of crude title compound. ESI-MS m/z: 216.1 [M+1]+, Retention time 1.01 min; $^1$H NMR (CDCl$_3$, 400.342 MHz) 45 ppm 2.50-2.59 (m, 1H), 3.31-3.39 (m, 1H), 4.65-4.70 (m, 1H), 4.87-4.92 (m, 1H), 5.91 (t, J=8 Hz, 1H), 7.95 (d, J=8 Hz, 1H), 8.68 (d, J=8 Hz, 1H), 8.73 (s, 1H).

Step 2: 2-chloro-4-(4-(oxetan-2-yl)pyridin-3-yl)benzonitrile (28)

To the solution of 2-chloro-4-(4,4,5,5-tetramethyl-1,3,2-dioxaborolan-2-yl)benzonitrile (569 mg, 2.16 mmol), 3-bromo-4-(oxetan-2-yl)pyridine (462 mg, 2.16 mmol) and PdCl$_2$(dppf).CH$_2$Cl$_2$ adduct (176 mg, 0.216 mmol) in DMF (10 mL) was added a solution of Na$_2$CO$_3$. (2 M, 2.70 ml, 5.40 mmol) under Nitrogen atmosphere. The mixture was stirred and heated at 100° C. for 4 hrs. Reaction mixture was cooled to room temperature and diluted with EtOAc. The organic layer was washed with water and brine. The aqueous layer was extracted with EtOAc. The combined organic phases were dried with Na$_2$SO$_4$, filtered and concentrated in vacuo. Purification by ISCO 12 g (0-40% EtOAc/Heptane) to give 2-chloro-4-(4-(oxetan-2-yl)pyridin-3-yl)benzonitrile (54 mg, 9%) as colorless solid; ESI-MS m/z: 271 [M+H]$^+$, Retention time 1.42 min. $^1$H-NMR (MeOD, 400 MHz) δ 2.58-2.67 (m, 1H), 2.82-2.90 (m, 1H), 4.61-4.67 (m, 1H), 4.77-4.83 (m, 1H), 5.88 (t, J=7.6 Hz, 1H), 7.46 (dd, J=8.0, 1.2 Hz, 1H), 7.67 (d, J=1.2 Hz, 1H), 7.94 (d, J=8.0 Hz, 1H), 7.96 (d, J=4.8 Hz, 1H), 8.47 (s, 1H), 8.74 (d, J=4.8 Hz, 1H);

The racemate was separated by chiral HPLC (ChiralPak AS-H, 40% EtOH/Heptane, v/v) to give 28-(enantiomer-1) (retention time: 8.58 min) and 28-(enantiomer-2) (retention time: 12.52 min).

Example 29

Synthesis of 2-chloro-4-[4-(2-ethoxy-1-hydroxy-ethyl)-5-fluoro-Pyridin-3-yl]-benzonitrile

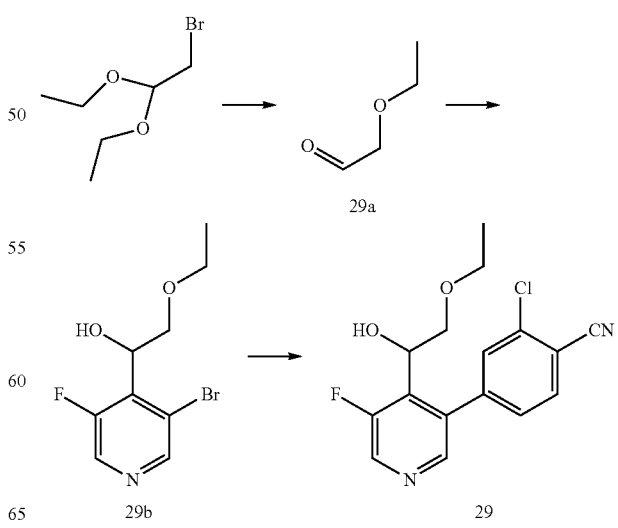

Step 1: Ethoxy-acetaldehyde (29a)

A sealed tube was charged with 2-bromo-1,1-diethoxy-ethane (3.82 mL, 25.4 mmol) and sodium ethoxide (16.44 g, 50.7 mmol). The tube was sealed, heated to 120° C. and stirred overnight. The sealed tube was cooled to room temperature and the contents are dissolved in DCM and washed with water twice. The organic layer was separated, dried over sodium sulfate and concentrated in vacuo to give 1,1,2-triethoxy-ethane, which was taken into the next step without further purification. A portion (1.00 g, 6.16 mmol) was dissolved in THF (4 mL) at 0° C. and 5M aqueous HCl (2.5 mL, 12.3 mmol) was added. The reaction mixture was left to stir at room temperature for 1.5 hrs. The mixture was taken up in DCM and washed with water once. The aqueous layer was extracted twice with DCM. The organic layer was dried over sodium sulfate and concentrated in vacuo to afford ethoxy-acetaldehyde, which was taken into the next step with no further purification.

Step 2: 1-(3-Bromo-5-fluoro-pyridin-4-yl)-2-ethoxy-ethanol (29b)

n-BuLi (2.66 mL, 4.26 mmol) was added to a solution of diisopropylamine (0.607 mL, 4.26 mmol) in THF (10 mL) at −78° C. After 30 min, 3-bromo-5-fluoropyridine (0.500 g, 2.84 mmol) in THF (10 mL) is added dropwise. The mixture was stirred at −78° C. for 1 hr, and 2-ethoxyacetaldehyde (0.464 g, 4.26 mmol) was added dropwise. The reaction mixture was stirred at −78° C. for 2 hrs. The reaction is quenched with a saturated aqueous NaHCO$_3$ solution and the cooling bath was removed. The mixture was shaken with ethyl acetate and the organic phase is washed with brine, dried over MgSO$_4$, and concentrated in vacuo. The residue was purified by silica gel flash chromatography employing heptane-ethyl acetate (4:1) to give 1-(3-bromo-5-fluoro-pyridin-4-yl)-2-ethoxy-ethanol. MS (ESI) m/z 266.0 (M+H)$^+$.

Step 3: 2-Chloro-4-[4-(2-ethoxy-1-hydroxy-ethyl)-5-fluoro-pyridin-3-yl]-benzonitrile hydrochloride (29)

A 25 mL round bottom flask was charged with 2-chloro-4-(4,4,5,5-tetramethyl-[1,3,2]dioxaborolan-2-yl)-benzonitrile (74 mg, 0.282 mmol), 1-(3-bromo-5-fluoro-pyridin-4-yl)-2-ethoxy-ethanol (62 mg, 0.235 mmol), 2M aqueous sodium carbonate (0.235 mL, 0.470 mmol) and DMF (5 mL). The reaction mixture was evacuated and flushed with N$_2$ twice, followed by addition of PdCl$_2$(dppf). CH$_2$Cl$_2$ adduct (9.6 mg, 0.012 mmol). The reaction was stirred under N$_2$ at 100° C. for 30 min. The reaction mixture was cooled to room temperature diluted with ethyl acetate and washed with water twice. The organic layer was dried over sodium sulfate and concentrated in vacuo. The crude was dissolved in DMF (5 mL) and purified by HPLC using an Xbridge Shield RP18 column and gradient 0.1% aqueous NH$_4$OH in acetonitrile to afford a solid, which was dissolved in DCM (2 mL) and 4N HCl in dioxane (0.5 mL). The solvents were evaporated and the product was lyophilized to afford the product 2-chloro-4-[4-(2-ethoxy-1-hydroxy-ethyl)-5-fluoro-pyridin-3-yl]-benzonitrile as an HCl salt. $^1$H NMR (400 MHz, MeOD, HCl salt) δ ppm 1.17 (t, J=6.9 Hz, 3H), 3.46-3.57 (m, 2H), 3.81 (dd, J=6.7, 1.4 Hz, 2H), 4.90 (t, J=6.8 Hz, 1H), 7.61 (dd, J=8.0, 1.6 Hz, 1H), 7.86 (d, J=1.5 Hz, 1H), 7.96 (d, J=8.1 Hz, 1H), 8.36 (s, 1H), 8.60 (d, J=2.8 Hz, 1H); HRMS: (ESI) m/z 321.0801 [(M+H)$^+$ Calcd for C$_{16}$H$_{14}$ClFN$_2$O$_2$ 321.0806].

Example 30

Synthesis of 2-Chloro-4-[5-fluoro-4-(1-hydroxy-2-isopropoxy-ethyl)-pyridin-3-yl]-benzonitrile hydrochloride

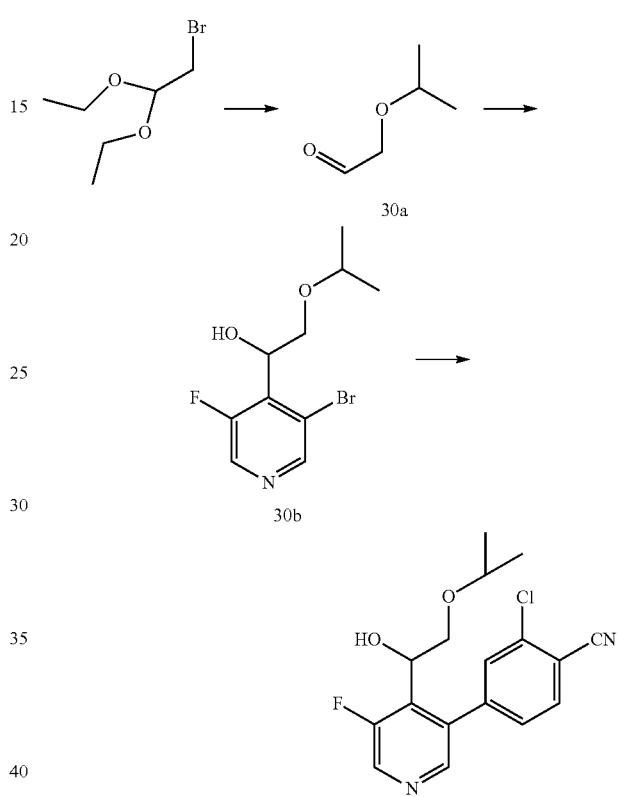

Step 1: Isopropoxy-acetaldehyde (30a)

NaH (3.35 g, 84 mmol) was added to isopropanol (5.38 mL, 69.9 mmol) at 0° C. The reaction mixture was stirred at room temperature for 30 min followed by the addition of 2-bromo-1,1-diethoxyethane (7.89 mL, 52.4 mmol). The tube was sealed, heated to 120° C. and stirred overnight. The sealed tube was cooled to room temperature and the contents were dissolved in DCM and washed with water twice. The organic layer was separated, dried over sodium sulfate and concentrated in vacuo to give 2-(2,2-diethoxy-ethoxy)-propane, which was hydrolyzed according to the method described in example 29 to give crude isopropoxy-acetaldehyde.

Step 2: 1-(3-Bromo-5-fluoro-pyridin-4-yl)-2-isopropoxy-ethanol (30b)

1-(3-Bromo-5-fluoro-pyridin-4-yl)-2-isopropoxy-ethanol was prepared using isopropoxy-acetaldehyde according to the procedure described in Example 29.
MS (ESI) m/z 280.0 (M+H)$^+$ Step 3: 2-Chloro-4-[5-fluoro-4-(1-hydroxy-2-isopropoxy-ethyl)-pyridin-3-yl]-benzonitrile hydrochloride (30)

2-Chloro-4-[5-fluoro-4-(1-hydroxy-2-isopropoxy-ethyl)-pyridin-3-yl]-benzonitrile was prepared according to the procedure described in Example 29. $^1$H NMR (400 MHz, MeOD, HCl salt) δ ppm 1.09 (d, J=6.1 Hz, 3H), 1.15 (d, J=6.1 Hz, 3H), 3.55-3.65 (m, 1H), 3.76-3.90 (m, 2H), 4.83-4.91 (m, 1H), 7.63 (dd, J=8.0, 1.6 Hz, 1H), 7.89 (d, J=1.5 Hz, 1H), 7.96 (d, J=7.8 Hz, 1H), 8.36 (s, 1H), 8.60 (d, J=3.0 Hz, 1H); HRMS: (ESI) m/z 335.0964 [(M+H)$^+$ Calcd for $C_{17}H_{16}ClFN_2O_2$ 335.0962].

Example 31

Synthesis of 2-Chloro-4-[4-(3-ethoxy-1-hydroxy-propyl)-5-fluoro-pyridin-3-yl]-benzonitrile

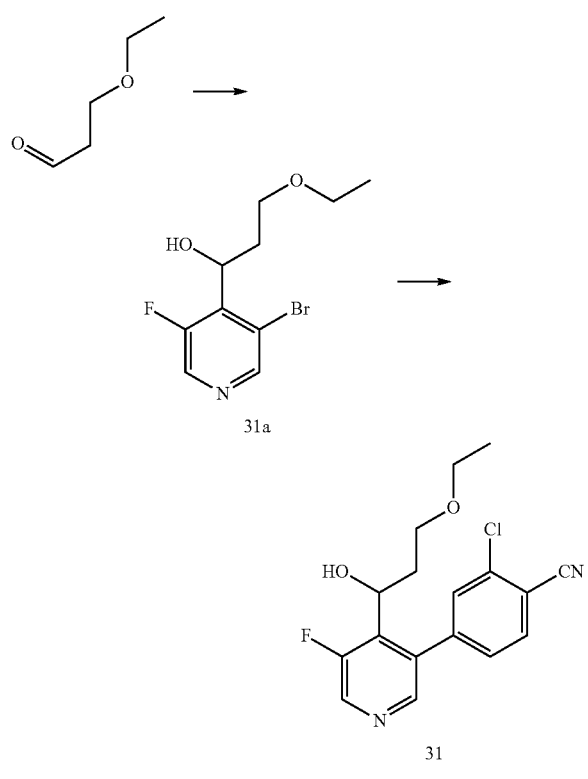

Step 1: 1-(3-Bromo-5-fluoro-pyridin-4-yl)-3-ethoxy-propan-1-ol (31a)

1-(3-Bromo-5-fluoro-pyridin-4-yl)-3-ethoxy-propan-1-ol was prepared according to the procedure described in Example 29. MS (ESI) m/z 280.0 (M+H)$^+$ Step 2: 2-Chloro-4-[4-(3-ethoxy-1-hydroxy-propyl)-5-fluoro-pyridin-3-yl]-benzonitrile (31)

2-Chloro-4-[4-(3-ethoxy-1-hydroxy-propyl)-5-fluoro-pyridin-3-yl]-benzonitrile was prepared according to the procedure described in Example 29. $^1$H NMR (400 MHz, MeOD) δ ppm 1.05 (t, J=6.9 Hz, 3H), 1.99-2.27 (m, 2H), 3.37-3.43 (m, 3H), 3.50-3.59 (m, 1H), 4.96 (dd, J=8.2, 5.4 Hz, 1H), 7.59 (dd, J=8.0, 1.6 Hz, 1H), 7.80 (d, J=1.5 Hz, 1H), 7.99 (d, J=7.8 Hz, 1H), 8.48 (s, 1H), 8.75 (d, J=3.3 Hz, 1H); HRMS: (ESI) m/z 335.0960 [(M+H)$^+$ Calcd for $C_{17}H_{16}ClFN_2O_2$ 335.0962].

Example 32

Synthesis of 2-Chloro-4-[5-fluoro-4-(1-hydroxy-1-methyl-ethyl)-pyridin-3-yl]-benzonitrile

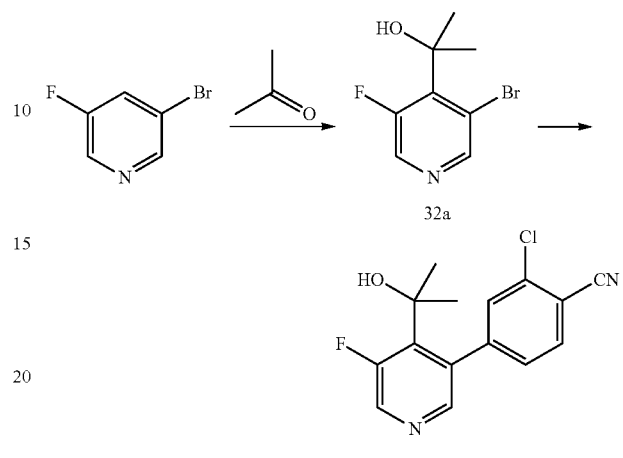

Step 1: 2-(3-Bromo-5-fluoro-pyridin-4-yl)-propan-2-ol (32a)

2-(3-Bromo-5-fluoro-pyridin-4-yl)-propan-2-ol was prepared according to the procedure described in Example 29. MS (ESI) m/z 235.9 (M+H)$^+$ Step 2: 2-Chloro-4-[5-fluoro-4-(1-hydroxy-1-methyl-ethyl)-pyridin-3-yl]-benzonitrile (32)

2-Chloro-4-[5-fluoro-4-(1-hydroxy-1-methyl-ethyl)-pyridin-3-yl]-benzonitrile was prepared according to the procedure described in Example 29. $^1$H NMR (400 MHz, MeOD) δ ppm 1.66 (s, 6H), 7.39 (dd, J=7.8, 1.5 Hz, 1H), 7.58 (d, J=1.5 Hz, 1H), 7.79 (d, J=7.8 Hz, 1H), 8.10 (s, 1H), 8.47 (d, J=3.8 Hz, 1H); HRMS: (ESI) m/z 291.0700 [(M+H)$^+$ Calcd for $C_{15}H_{12}ClFN_2O$ 291.0700].

Example 33

Synthesis of 2-Fluoro-4-[5-fluoro-4-(1-hydroxy-1-methyl-ethyl)-pyridin-3-yl]-benzonitrile

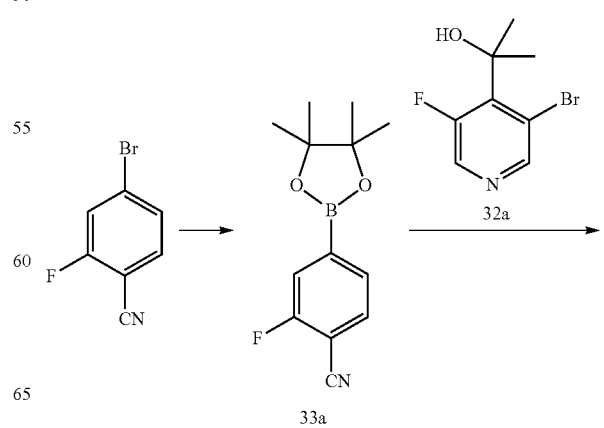

-continued

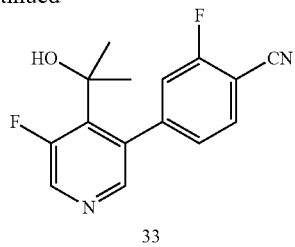

Step 1: 2-Fluoro-4-(4,4,5,5-tetramethyl-[1,3,2]dioxaborolan-2-yl)-benzonitrile (33a)

2-Fluoro-4-(4,4,5,5-tetramethyl-[1,3,2]dioxaborolan-2-yl)-benzonitrile was prepared according to the procedure described in Example 15. $^1$H NMR (400 MHz, DMSO-$d_6$) δ ppm 1.31 (s, 12H), 7.61 (d, J=9.6 Hz, 1H), 7.64 (dd, J=7.6, 0.8 Hz, 1H), 7.94 (dd, J=7.6, 6.6 Hz, 1H)

Step 2: 2-Fluoro-4-[5-fluoro-4-(1-hydroxy-1-methyl-ethyl)-pyridin-3-yl]-benzonitrile (33)

2-Fluoro-4-[5-fluoro-4-(1-hydroxy-1-methyl-ethyl)-pyridin-3-yl]-benzonitrile was prepared according to the procedure described in Example 29. $^1$H NMR (400 MHz, MeOD) δ ppm 1.66 (d, J=1.5 Hz, 6H), 7.28 (dd, J=8.1, 1.5 Hz, 1H), 7.32 (dd, J=10.0, 1.4 Hz, 1H), 7.70-7.77 (m, 1H), 8.10 (s, 1H), 8.47 (d, J=3.5 Hz, 1H); HRMS: (ESI) m/z 275.0995 [(M+H)$^+$ Calcd for C$_{15}$H$_{12}$F$_2$N$_2$O 275.0996].

Example 34

Synthesis of 2-Chloro-4-[4-(1,2-dihydroxy-ethyl)-5-fluoro-pyridin-3-yl]-benzonitrile

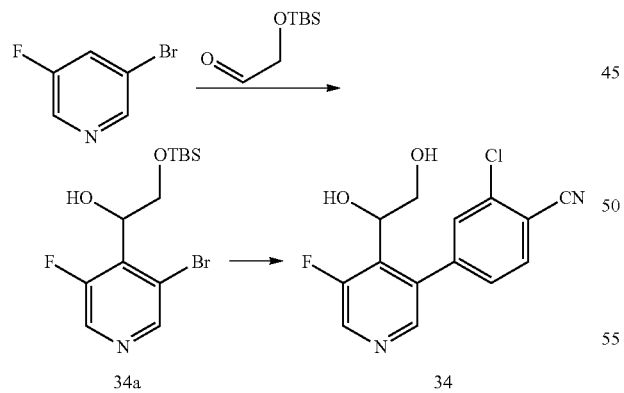

Step 1: 1-(3-Bromo-5-fluoro-pyridin-4-yl)-2-(tert-butyl-dimethyl-silanyloxy)-ethanol (34a)

1-(3-Bromo-5-fluoro-pyridin-4-yl)-2-(tert-butyl-dimethyl-silanyloxy)-ethanol was prepared according to the procedure described in Example 29. MS (ESI) m/z 351.9 (M+H)$^+$

Step 2: 2-Chloro-4-[4-(1,2-dihydroxy-ethyl)-5-fluoro-pyridin-3-yl]-benzonitrile (34)

A 25 mL round bottom flask was charged with 2-chloro-4-(4,4,5,5-tetramethyl-[1,3,2]dioxaborolan-2-yl)benzonitrile (250 mg, 0.949 mmol), 1-(3-bromo-5-fluoro-pyridin-4-yl)-2-(tert-butyl-dimethyl-silanyloxy)-ethanol (332 mg, 0.949 mmol), 2M aqueous sodium carbonate (0.95 mL, 1.90 mmol) and DMF (5 mL). The reaction mixture was evacuated and flushed with N$_2$ twice followed by addition of PdCl$_2$(dppf).CH$_2$Cl$_2$ adduct (38.7 mg, 0.047 mmol). The reaction was stirred under N$_2$ at 100° C. for 3 days. The reaction mixture was cooled to room temperature, diluted with ethyl acetate and washed with water twice. The organic layer was dried over sodium sulfate and concentrated in vacuo. The crude was dissolved in DMF (5 mL) and 4M HCl solution in dioxane (2.372 mL, 9.49 mmol). The reaction mixture was stirred at room temperature for 1 hr. The reaction mixture was quenched with saturated NaHCO$_3$ solution and extracted with DCM twice. The organic layer was dried over sodium sulfate and concentrated in vacuo. The crude was purified by silica gel flash chromatography employing DCM-MeOH (9:1) to afford 2-chloro-4-[4-(1,2-dihydroxy-ethyl)-5-fluoro-pyridin-3-yl]-benzonitrile. $^1$H NMR (400 MHz, MeOD) δ ppm 3.72-4.03 (m, 1H), 4.80 (t, J=6.8 Hz, 1H), 7.61 (dd, J=8.0, 1.6 Hz, 1H), 7.82 (d, J=1.3 Hz, 1H), 7.95 (d, J=8.1 Hz, 1H), 8.31 (s, 1H), 8.55 (d, J=2.5 Hz, 1H); HRMS: (ESI) ink 293.0488 [(M+H)$^+$ Calcd for C$_{14}$H$_{10}$ClFN$_2$O$_2$ 293.0493].

Example 35

Synthesis of 5-(5-Fluoro-4-hydroxymethyl-pyridin-3-yl)-3H-isobenzofuran-1-one

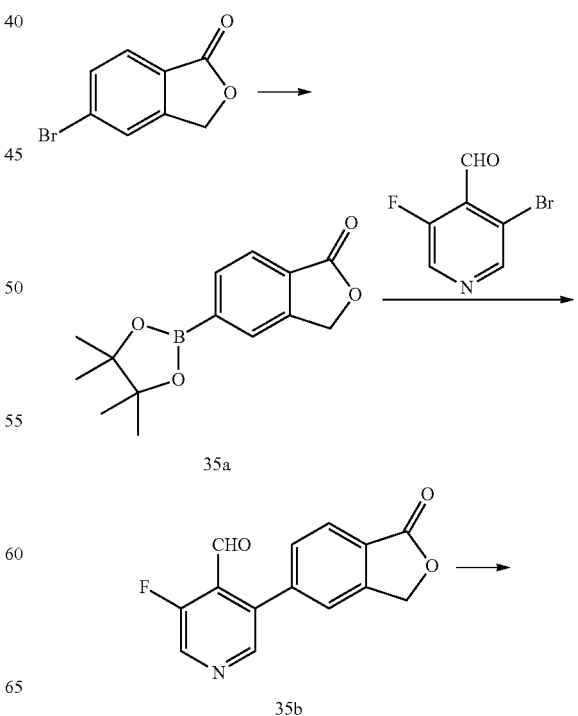

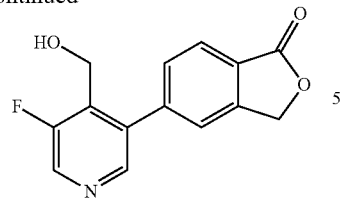

35

Step 1: 5-(4,4,5,5-Tetramethyl-[1,3,2]dioxaborolan-2-yl)-3H-isobenzofuran-1-one (35a)

A 100 round bottom flask was charged with 5-bromo-3H-isobenzofuran-1-one (750 mg, 3.52 mmol), bis(pinacolato)diboron (894 mg, 3.52 mmol), potassium acetate (691 mg, 7.04 mmol) and 1,4-dioxane (25 mL). The reaction mixture was evacuated and flushed with $N_2$ twice followed by addition of $PdCl_2$(dppf).$CH_2Cl_2$ adduct (144 mg, 0.176 mmol). The reaction was stirred under $N_2$ at 100° C. overnight. The reaction mixture was cooled to room temperature, diluted with ethyl acetate and washed with water twice. The organic layer was dried over sodium sulfate and concentrated in vacuo. The crude was purified using silica gel flash chromatography employing heptane-ethyl acetate (7:3) to afford 5-(4,4,5,5-tetramethyl-[1,3,2]dioxaborolan-2-yl)-3H-isobenzofuran-1-one.

Step 2: 3-fluoro-5-(1-oxo-1,3-dihydro-isobenzofuran-5-yl)-pyridine-4-carbaldehyde (35b)

To 5-(4,4,5,5-tetramethyl-[1,3,2]dioxaborolan-2-yl)-3H-isobenzofuran-1-one (210 mg, 0.809 mmol) in DMF (4 mL) was added 3-bromo-5-fluoro-pyridine-4-carbaldehyde (150 mg, 0.735 mmol) and 2M aqueous sodium carbonate (0.735 mL, 1.471 mmol). The reaction mixture was flushed and evacuated with $N_2$ twice followed by the addition of $PdCl_2$(dppf).$CH_2Cl_2$ adduct (30.0 mg, 0.037 mmol). The reaction mixture was stirred at 100° C. for 1 hour. The reaction was cooled to room temperature, diluted with ethyl acetate and washed with water twice. The organic layer was separated, dried over sodium sulfate and concentrated in vacuo to afford 3-fluoro-5-(1-oxo-1,3-dihydro-isobenzofuran-5-yl)-pyridine-4-carbaldehyde, which was taken into the next step without further purification.

Step 3: 5-(5-Fluoro-4-hydroxymethyl-pyridin-3-yl)-3H-isobenzofuran-1-one (35)

To 3-fluoro-5-(1-oxo-1,3-dihydro-isobenzofuran-5-yl)-pyridine-4-carbaldehyde (180 mg, 0.700 mmol) in MeOH (7 mL) at 0° C. was added sodium borohydride (39.7 mg, 1.050 mmol). The reaction mixture was stirred at room temperature for 30 min. The reaction was quenched with water and extracted with DCM twice. The organic layer was dried over sodium sulfate and concentrated in vacuo. The crude was dissolved in MeOH (10 mL) and purified on HPLC using RP18 column and gradient 0.1% aqueous $NH_4OH$ in acetonitrile to afford 5-(5-fluoro-4-hydroxymethyl-pyridin-3-yl)-3H-isobenzofuran-1-one. $^1$H NMR (400 MHz, MeOD) δ ppm 4.62 (d, J=1.5 Hz, 2H), 5.51 (s, 2H), 7.78 (d, J=7.8 Hz, 1H), 7.82 (s, 1H), 8.04 (d, J=7.8 Hz, 1H), 8.46 (s, 1H), 8.59 (d, J=1.5 Hz, 1H); HRMS: (ESI) m/z 260.0735 [(M+H)$^+$ Calcd for $C_{14}H_{10}FNO_3$ 260.0723].

Example 36

Synthesis of 5-[5-Fluoro-4-(1-hydroxy-ethyl)-pyridin-3-yl]-3H-Isobenzofuran-1-one

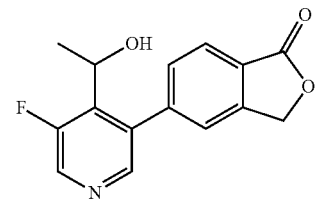 [SMILES: CC(O)c1c(F)cncc1-c1ccc2c(c1)COC2=O]

5-(4,4,5,5-Tetramethyl-[1,3,2]dioxaborolan-2-yl)-3H-isobenzofuran-1-one and 1-(3-bromo-5-fluoro-pyridin-4-yl)-ethanol were reacted according to the procedure described in Example 35.

$^1$H NMR (400 MHz, MeOD) δ ppm 1.58 (dd, J=6.6, 1.0 Hz, 3H), 4.88-4.93 (m, 1H), 5.51 (s, 2H), 7.63 (d, J=7.8 Hz, 1H), 7.68 (s, 1H), 8.03 (d, J=7.8 Hz, 1H), 8.32 (s, 1H), 8.54 (d, J=2.8 Hz, 1H). HRMS: (ESI) m/z 274.0873 [(M+H)$^+$ Calcd for $C_{15}H_{12}FNO_3$ 274.0879].

Example 37

Synthesis of [3-(6-Chloro-1-methyl-1H-benzoimidazol-2-yl)-pyridin-4-yl]-methanol

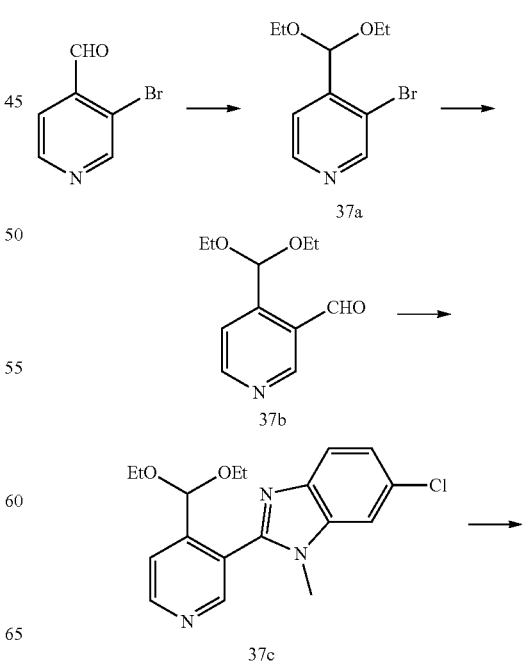

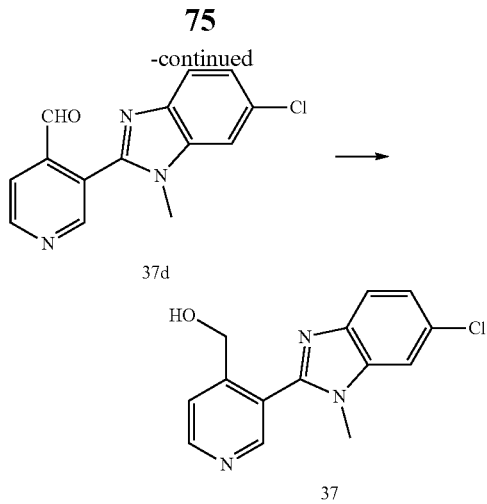

Step 1: 3-Bromo-4-diethoxymethyl-pyridine (37a)

To 3-bromoisonicotinaldehyde (2.0 g, 10.75 mmol) in EtOH (25 mL) was added triethyl formate (1.753 g, 11.83 mmol) and ammonium chloride (0.115 g, 2.150 mmol). The reaction mixture was refluxed overnight, then cooled to room temperature and concentrated in vacuo. The crude was dissolved in DCM and washed with water twice. The organic layer was dried over sodium sulfate and concentrated in vacuo to give 3-bromo-4-diethoxymethyl-pyridine. This was taken on to next step with out further purification. MS (ESI) m/z 262.0 (M+H)$^+$ Step 2: 4-Diethoxymethyl-pyridine-3-carbaldehyde (37b)

BuLi (5.84 mL, 9.35 mmol) was added to a solution of 3-bromo-4-diethoxymethyl-pyridine (2.21 g, 8.50 mmol) in THF (50 mL) at −78° C. After 1 h, DMF (6.58 mL, 85 mmol) was added. The reaction was stirred at −78° C. for 1 hr. It was then warmed to room temperature, quenched with water and extracted with ethyl acetate. The organic layer was dried over sodium sulfate and concentrated in vacuo to afford 1.4 g of 4-diethoxymethyl-pyridine-3-carbaldehyde, which was taken in the next step without further purification. MS (ESI) m/z 210.1 (M+H)$^+$ Step 3: 6-Chloro-2-(4-diethoxymethyl-pyridin-3-yl)-1-methyl-1H-benzoimidazole (37c)

A solution of 5-chloro-N$^1$-methylbenzene-1,2-diamine (383 mg, 2.446 mmol) and 4-diethoxymethyl-pyridine-3-carbaldehyde (512 mg, 2.446 mmol) in 1,4-dioxane (20 mL) was heated to 75° C. overnight. The mixture was cooled to room temperature and concentrated in vacuo. The residue was purified by silica gel flash chromatography employing heptane-ethyl acetate (1:1) to give of 6-chloro-2-(4-diethoxymethyl-pyridin-3-yl)-1-methyl-1H-benzoimidazole. MS (ESI) m/z 346.0 (M+H)$^+$ Step 4: 3-(6-Chloro-1-methyl-1H-benzoimidazol-2-yl)-pyridine-4-carbaldehyde (37d)

HBr (3.84 mL, 34.0 mmol) was added to 6-chloro-2-(4-diethoxymethyl-pyridin-3-yl)-1-methyl-1H-benzoimidazole (0.470 g, 1.359 mmol), and the reaction mixture was stirred for 10 min. The reaction was cooled to 0° C. and quenched with saturated aqueous sodium bicarbonate solution. It was extracted with DCM twice. The organic layer was dried over sodium sulfate and concentrated in vacuo to afford 3-(6-chloro-1-methyl-1H-benzoimidazol-2-yl)-pyridine-4-carbaldehyde. MS (ESI) m/z 272.0 (M+H).

Step 5: [3-(6-Chloro-1-methyl-1H-benzoimidazol-2-yl)-pyridin-4-yl]-methanol (37)

To a solution of 3-(6-chloro-1-methyl-1H-benzoimidazol-2-yl)-pyridine-4-carbaldehyde (50 mg, 0.184 mmol) in MeOH (4 mL) at 0° C. was added sodium borohydride (10.44 mg, 0.276 mmol). The mixture was stirred at room temperature for 30 min. The reaction was quenched with water (0.5 mL) and the mixture was concentrated in vacuo. The crude was taken up in MeOH (5 mL) and purified on HPLC using RP18 column and gradient 0.1% aqueous NH$_4$OH in acetonitrile to afford pure product [3-(6-chloro-1-methyl-1H-benzoimidazol-2-yl)-pyridin-4-yl]-methanol as a white color solid. $^1$H NMR (400 MHz, MeOD) δ ppm 3.76 (s, 3H), 4.64 (s, 2H), 7.38 (dd, J=8.7, 1.9 Hz, 1H), 7.71 (d, J=8.6 Hz, 1H), 7.73 (d, J=2.0 Hz, 1H), 7.84 (d, J=5.1 Hz, 1H), 8.69 (s, 1H), 8.79 (d, J=5.3 Hz, 1H); HRMS: (ESI) m/z 274.0739 [(M+H)$^+$ Calcd for C$_{14}$H$_{12}$ClN$_3$O 274.0747].

Example 38

[3-(6-Chloro-1-methyl-1H-benzoimidazol-2-yl)-5-fluoro-pyridin-4-yl]-methanol

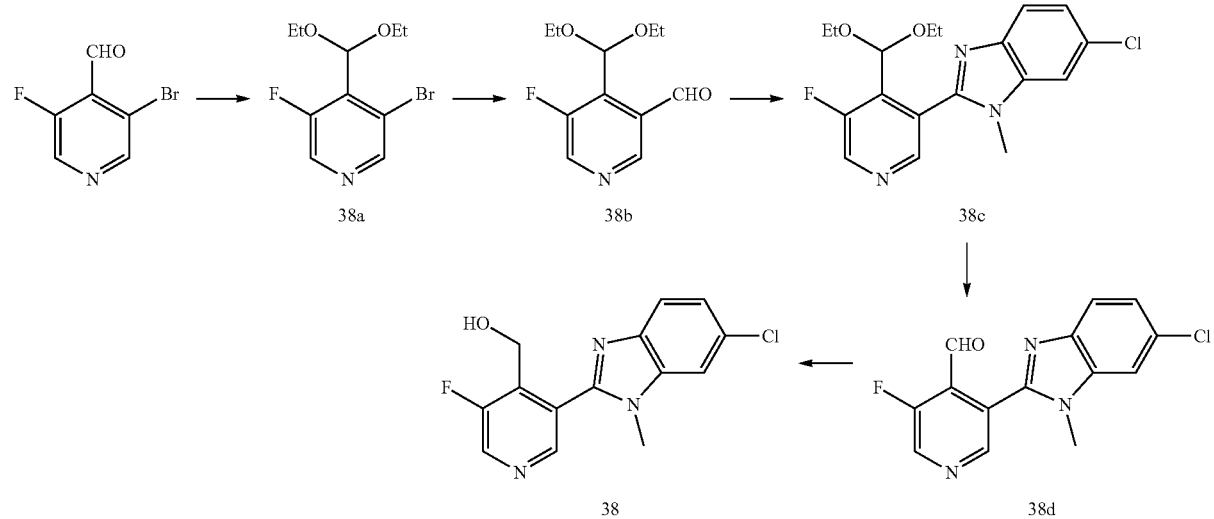

Step 1: 3-Bromo-4-diethoxymethyl-5-fluoro-pyridine (38a)

3-Bromo-4-diethoxymethyl-5-fluoro-pyridine was prepared according to the procedure described in Example 37. MS (ESI) m/z 280.0 (M+H)+

Step 2: 4-Diethoxymethyl-5-fluoro-pyridine-3-carbaldehyde (38b)

4-Diethoxymethyl-5-fluoro-pyridine-3-carbaldehyde was prepared according to the procedure described in Example 37. MS (ESI) m/z 228.0 (M+H)+

Step 3: [3-(6-Chloro-1-methyl-1H-benzoimidazol-2-yl)-5-fluoro-pyridin-4-yl]-methanol (38)

[3-(6-Chloro-1-methyl-1H-benzoimidazol-2-yl)-5-fluoro-pyridin-4-yl]-methanol was prepared according to the procedures described in Example 37. $^1$H NMR (400 MHz, MeOD) δ ppm 3.79 (s, 3H), 4.71 (s, 2H), 7.38 (dd, J=8.6, 2.0 Hz, 1H), 7.68-7.75 (m, 2H), 8.62 (s, 1H), 8.72 (d, J=1.5 Hz, 1H); HRMS: (ESI) m/z 292.0649 [(M+H)+ Calcd for $C_{14}H_{11}ClFN_3O$ 292.0653].

Example 39

Synthesis of 1-[3-(6-Chloro-1-methyl-1H-benzoimidazol-2-yl)-pyridin-4-yl]-ethanol

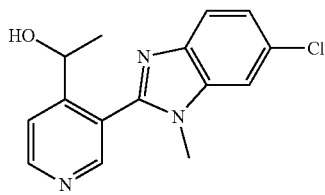 [SMILES: CC(O)c1ccncc1-c1nc2ccc(Cl)cc2n1C]

To a solution of 3-(6-chloro-1-methyl-1H-benzoimidazol-2-yl)-pyridine-4-carbaldehyde (75 mg, 0.276 mmol) in THF (4 mL) at −78° C. was added 3 M MeMgBr in diethyl ether (0.138 mL, 0.414 mmol) and the mixture was stirred at −78° C. for 0.5 hr. The reaction was quenched with water (0.5 mL) and the mixture was warmed to room temperature. It was concentrated in vacuo. The crude was taken up in MeOH (5 mL) and purified on RP-HPLC using RP18 column and gradient 0.1% aqueous NH4OH in acetonitrile, followed with a second purification by silica gel flash chromatography DCM-MeOH (9:1) to afford 1-[3-(6-chloro-1-methyl-1H-benzoimidazol-2-yl)-pyridin-4-yl]-ethanol. $^1$H NMR (400 MHz, MeOD) δ ppm 1.34 (d, J=6.6 Hz, 3H), 3.73 (s, 3H), 4.81-4.86 (m, 1H), 7.38 (dd, J=8.6, 2.0 Hz, 1H), 7.72 (d, J=9.1 Hz, 1H), 7.73 (d, J=2.0 Hz, 1H), 7.86 (d, J=5.3 Hz, 1H), 8.63 (s, 1H), 8.79 (d, J=5.3 Hz, 1H); HRMS: (ESI) ink 288.0894 [(M+H)+ Calcd for $C_{15}H_{14}ClN_3O$ 288.0904].

Example 40

Synthesis of 4-(4-(cyclopropyl(hydroxy)methyl)pyridin-3-yl)-2-methoxybenzonitrile

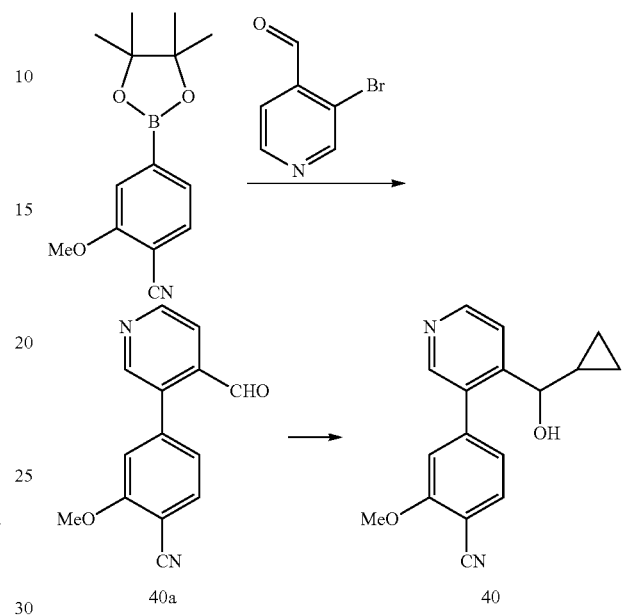

Step 1: 4-(4-formylpyridin-3-yl)-2-methoxybenzonitrile (40a)

A mixture of 2-methoxy-4-(4,4,5,5-tetramethyl-1,3,2-dioxaborolan-2-yl)benzonitrile (259 mg, 1 mmol), 3-bromoisonicotinaldehyde (186 mg, 1.000 mmol), a solution of sodium carbonate (2M in water, 1.000 ml, 2.000 mmol), bis(triphenylphosphine)palladium(II) chloride (17.55 mg, 0.025 mmol) in DMF (6 mL, dry) was heated to 120° C. for 3 hrs. After concentration, the residue was dissolved into $CH_2Cl_2$-MeOH and mixed with silica gel and concentrated. After flash column (MeOH—$CH_2Cl_2$, v/v, 0.5%-1%) yielded colorless solid (170 mg). $^1$H NMR (400.3 MHz, CDCl3): δ 3.99 (s, 3H), 6.98 (d, J=1.32 Hz, 1H), 7.05 (dd, J=1.48, 7.8 Hz, 1H), 7.71 (d, J=7.8 Hz, 1H), 7.81 (d, J=5 Hz, 1H), 8.81 (s, 1H), 8.90 (d, J=5 Hz, 1H), 10.04 (s, 1H).

Step 2: 4-(4-(cyclopropyl(hydroxy)methyl)pyridin-3-yl)-2-methoxybenzonitrile (40)

To a solution of 4-(4-formylpyridin-3-yl)-2-methoxybenzonitrile (100 mg, 0.42 mmol) in THF (4 mL) at −36° C. was added 0.5M c-PrMgCl in THF (2.27 mL, 1.13 mmol) dropwise and the mixture was stirred at −36° C. for 1 hr. The mixture was quenched with water at −36° C., silica gel was added, and the mixture was concentrated in vacuo. The residue was purified by silica chromatography eluting with a 40 to 100% EtOAc-heptane gradient. The product obtained was re-purified by Xbridge C18 eluting with a 10 to 100% acetonitrile-water gradient to give 4-(4-(cyclopropyl(hydroxy)methyl)pyridin-3-yl)-2-methoxybenzonitrile. $^1$H NMR (400 MHz, DMSO-$d_6$) δ ppm −0.13--−0.05 (m, 1H), 0.20-0.29 (m, 1H), 0.29-0.41 (m, 2H), 0.91-1.06 (m, 1H), 3.95 (s, 3H), 4.16 (dd, J=6.6, 4.3 Hz, 1H), 5.39 (d, J=4.5 Hz, 1H), 7.12 (dd, J=7.8, 1.3 Hz, 1H), 7.27 (d, J=1.3 Hz, 1H), 7.66 (d, J=5.3 Hz, 1H), 7.83 (d, J=7.8 Hz, 1H), 8.42 (s, 1H), 8.62 (d, J=5.3 Hz, 1H). HRMS: (ESI) m/z 281.1280 [(M+H)+ Calcd for C17H16N2O2 281.1290].

Example 41

Synthesis of 4-[4-(1-Hydroxy-2-methyl-propyl)-pyridin-3-yl]-2-methoxy-benzonitrile

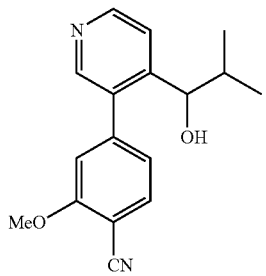 [SMILES: COc1cc(-c2cnccc2C(O)C(C)C)ccc1C#N]

4-[4-(1-Hydroxy-2-methyl-propyl)-pyridin-3-yl]-2-methoxy-benzonitrile was prepared according to the procedure described in Example 40. 1H NMR (400 MHz, DMSO-d6) δ ppm 0.52 (d, J=6.8 Hz, 3H), 0.78 (d, J=6.6 Hz, 3H), 1.66-1.71 (m, 1H), 3.95 (s, 3H), 4.32 (dd, J=6.6, 3.3 Hz, 1H), 5.41 (d, J=3.5 Hz, 1H), 7.11 (dd, J=7.8, 1.3 Hz, 1H), 7.25 (d, J=1.0 Hz, 1H), 7.56 (d, J=5.3 Hz, 1H), 7.84 (d, J=7.8 Hz, 1H), 8.39 (s, 1H), 8.61 (d, J=5.3 Hz, 1H). HRMS: (ESI) m/z 283.1447 [(M+H)+ Calcd for C17H18N2O2 283.1446].

Example 42

Synthesis of 4-[4-(1-Hydroxy-butyl)-pyridin-3-yl]-2-methoxy-benzonitrile

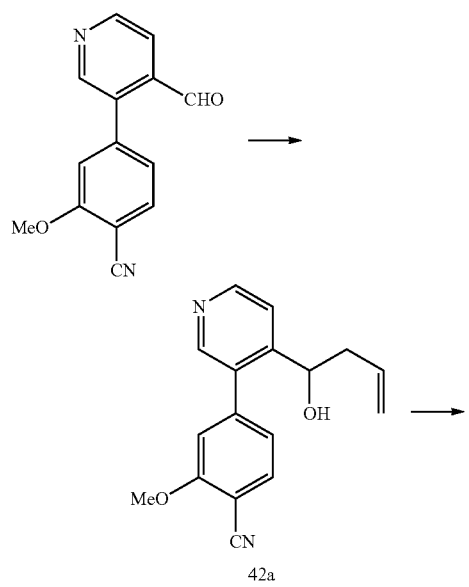

Step 1: 4-[4-(1-Hydroxy-but-3-enyl)-pyridin-3-yl]-2-methoxy-benzonitrile (42a)

4-[4-(1-Hydroxy-but-3-enyl)-pyridin-3-yl]-2-methoxy-benzonitrile was prepared according to the procedure described in Example 40. MS (ESI) m/z 281.1 (M+H)+

Step 2: 4-[4-(1-Hydroxy-butyl)-pyridin-3-yl]-2-methoxy-benzonitrile (42)

To a flask containing 4-(4-(1-hydroxy-but-3-enyl)pyridin-3-yl)-2-methoxybenzonitrile (140 mg, 0.499 mmol) and MeOH (5 mL) was added 10% Pd/C (53.1 mg, 0.050 umol), and the flask was flushed with H2. The mixture was stirred under H2 at room temperature for 10 min. The mixture was then filtered and concentrated. The residue was purified by Xbridge C18 eluting with a 20 to 70% acetonitrile-water gradient to give 4-(4-(1-hydroxybutyl)pyridin-3-yl)-2-methoxybenzonitrile. 1H NMR (400 MHz, DMSO-d6) δ ppm 0.66 (t, J=7.3 Hz, 3H), 1.04-1.28 (m, 2H), 1.35-1.54 (m, 2H), 3.95 (s, 3H), 4.59 (ddd, J=8.2, 4.3, 4.2 Hz, 1H), 5.35 (d, J=4.0 Hz, 1H), 7.10 (dd, J=8.0, 1.4 Hz, 1H), 7.25 (d, J=1.3 Hz, 1H), 7.60 (d, J=5.3 Hz, 1H), 7.84 (d, J=7.8 Hz, 1H), 8.39 (s, 1H), 8.61 (d, J=5.1 Hz, 1H). HRMS: (ESI) ink 283.1446 [(M+H)+ Calcd for C17H18N2O2 283.1446].

General Procedure for Examples 43-53

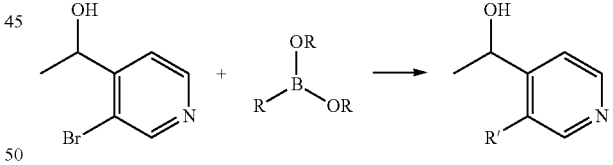

To a solution of 1-(3-bromo-pyridin-4-yl)-ethanol (1 eq) in DMF (600 µl) were added Na2CO3 (2 eq) and boronic acid (1.1 eq). To the stirred mixture, PdCl2(dppf).CH2Cl2 complex (0.02 eq) was added. The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (solvent 1: water with 0.1% TFA, solvent 2: methanol/acetonitrile 4:1 with 0.1% TFA).
Isolated products were identified by LC-MS and NMR.
Purification Procedures
Preparative LC-MS (System A):
Waters 2525 HPLC system with Micromass ZQ MS detection (equilibration: 98% water-2% methanol/acetonitrile 4:1, both containing 0.1% TFA using a flow rate of 15 ml/min). One minute elution with 2% of solvent 2, followed by linear gradient of seven minutes from 2% to 60% of solvent 2, followed by one minute elution with 60% of solvent 2, followed by linear gradient of six seconds from 60% to 100% of solvent 2, followed by two minutes elution with 100% of solvent 2, using a flow rate of 60 ml/min on a Waters Sunfire™ prep C-18 column 30×150 mm, 5 μm. The desired products were collected in multiple fractions, based on mass and UV detection.

Preparative LC-MS (System B):

Waters 2525 HPLC system with Micromass ZQ MS detection (equilibration: 98% water-2% methanol/acetonitrile 4:1, both containing 0.1% TFA using a flow rate of 15 ml/min). One minute elution with linear gradient from 2% to 10% of solvent 2, followed by linear gradient of seven minutes from 10% to 80% of solvent 2, followed by one minute elution with 80% of solvent 2, followed by linear gradient of six seconds from 80% to 100% of solvent 2, followed by two minutes elution with 100% of solvent 2, using a flow rate of 60 ml/min on a Waters Sunfire™ prep C-18 column 30×150 mm, 5 μm. The desired products were collected in multiple fractions, based on mass and UV detection.

Preparative LC-MS (System C):

Waters 2525 HPLC system with Micromass ZQ MS detection (equilibration: 95% water-5% methanol/acetonitrile 4:1, both containing 0.1% TFA using a flow rate of 15 ml/min). One minute elution with 10% of solvent 2, followed by linear gradient of five minutes from 10% to 50% of solvent 2, followed by one minute elution with 50% of solvent 2, followed by linear gradient of six seconds from 50% to 100% of solvent 2, followed by two minutes elution with 100% of solvent 2, using a flow rate of 60 ml/min on a Waters Sunfire™ prep C-18 column 30×150 mm, 5 μm. The desired products were collected in multiple fractions, based on mass and UV detection.

Preparative LC-MS (System D):

Waters 2525 HPLC system with Micromass ZQ MS detection (equilibration: 95% water-5% methanol/acetonitrile 4:1, both containing 0.1% TFA using a flow rate of 15 ml/min). One minute elution with linear gradient from 10% to 20% of solvent 2, followed by linear gradient of five minutes from 20% to 60% of solvent 2, followed by one minute elution with 60% of solvent 2, followed by linear gradient of six seconds from 60% to 100% of solvent 2, followed by two minutes elution with 100% of solvent 2, using a flow rate of 60 ml/min on a Waters Sunfire™ prep C-18 column 30×150 mm, 5 μm. The desired products were collected in multiple fractions, based on mass and UV detection.

Analytical Procedures

Analytical LC-MS (System 1):

Waters Acquity UPLC, run time: 6.00 min, Acquity Column 2.1×50 mm HSS T3 1.8μ. Solvent A: water+3 mM ammonium acetate+0.05% formic acid (from 98% to 2%), Solvent B: acetonitrile+0.04% formic acid (from 2% to 98%).

Analytical LC-MS (System 2):

Waters XBridge C18 column 3×30 mm, 2.5 μm, run time: 3 min, Solvent A: water+5% acetonitrile+0.5%-1% formic acid (from 99% to 5%), Solvent B: acetonitrile+0.5%-1% formic acid (from 1% to 95%).

¹H NMR (System 3):

500 Mhz Brucker Avance DRX, experiments in d-DMSO

¹H NMR (System 4):

400 Mhz Brucker Avance DRX, experiments in d-DMSO

Example 43

1-[3-(6-Methoxy-naphthalen-2-yl)-pyridin-4-yl]-ethanol

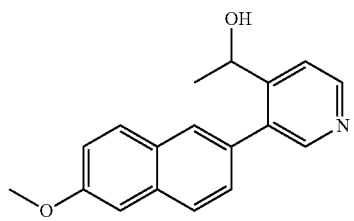

43

According to General Procedure, to a solution of 1-(3-bromo-pyridin-4-yl)-ethanol (50 mg, 247 μmol, 1 eq) in DMF (600 μl) were added Na₂CO₃ (52.5 mg, 495 μmol, 2 eq) and 6-methoxy-2-naphthaleneboronic acid (55 mg, 272 μmol, 1.1 eq). To the stirred mixture, PdCl₂(dppf).CH₂Cl₂ complex (4 mg, 4.9 μmol, 0.02 eq) was added.

The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (system A) and lyophilized to give 1-[3-(6-methoxy-naphthalen-2-yl)-pyridin-4-yl]-ethanol (54.5 mg, >95% purity, yield: 79%).

The isolated product was identified by LC-MS (system 1) and NMR (system 3): [M+H]⁺=280, retention time=1.88 min, ¹H NMR (500 MHz, DMSO-d₆) δ ppm 1.18 (d, J=6.41 Hz, 3H) 3.90 (s, 3H) 4.92 (q, J=6.36 Hz, 1H) 7.25 (dd, J=8.85, 2.14 Hz, 1H) 7.41 (s, 1H) 7.49 (d, J=8.39 Hz, 1H) 7.87-7.97 (m, 3H) 8.65 (s, 1H) 8.76 (d, J=5.65 Hz, 1H).

Example 44

1-[3-(3-Chloro-4-fluoro-phenyl)-pyridin-4-yl]-ethanol

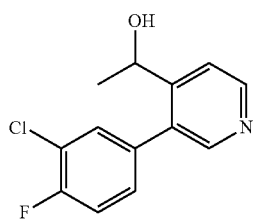

44

According to General Procedure, to a solution of 1-(3-bromo-pyridin-4-yl)-ethanol (20 mg, 99 μmol, 1 eq) in DMF (600 μl) were added Na₂CO₃ (21 mg, 198 μmol, 2 eq) and 3-chloro-4-fluorophenylboronic acid (19 mg, 109 μmol, 1.1 eq). To the stirred mixture, PdCl₂(dppf).CH₂Cl₂ complex (1.6 mg, 2 μmol, 0.02 eq) was added.

The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (system B) and lyophilized to give 1-[3-(3-chloro-4-fluoro-phenyl)-pyridin-4-yl]-ethanol (15.5 mg, >95% purity, yield: 63%).

The isolated product was identified by LC-MS (system 1) and NMR (system 3): [M+H]$^+$=252, retention time=1.52 min, $^1$H NMR (500 MHz, DMSO-d$_6$) δ ppm 1.18 (d, J=6.41 Hz, 3H) 4.75 (q, J=6.41 Hz, 1H) 7.43 (ddd, J=8.47, 4.65, 2.14 Hz, 1H) 7.56 (t, J=8.93 Hz, 1H) 7.68 (dd, J=7.17, 2.14 Hz, 1H) 7.77 (d, J=5.49 Hz, 1H) 8.48 (s, 1H) 8.68 (d, J=5.34 Hz, 1H).

Example 45

1-[3-(4-Trifluoromethoxy-phenyl)-pyridin-4-yl]-ethanol

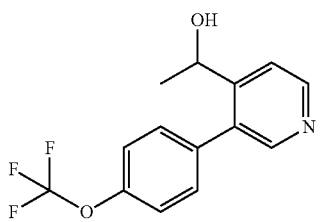

According to General Procedure, to a solution of 1-(3-bromo-pyridin-4-yl)-ethanol (20 mg, 99 μmol, 1 eq) in DMF (600 μl) were added Na$_2$CO$_3$ (21 mg, 198 μmol, 2 eq) and 4-(trifluoromethoxy)phenylboronic acid (22.4 mg, 109 μmol, 1.1 eq). To the stirred mixture, PdCl$_2$(dppf).CH$_2$Cl$_2$ complex (1.6 mg, 2 μmol, 0.02 eq) was added.

The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (system B) and lyophilized to give 1-[3-(4-trifluoromethoxy-phenyl)-pyridin-4-yl]-ethanol (13.3 mg, >95% purity, yield: 48%).

The isolated product was identified by LC-MS (system 1) and NMR (system 3): [M+H]$^+$=284, retention time=1.75 min, $^1$H NMR (500 MHz, DMSO-d$_6$) δ ppm 1.18 (d, J=6.41 Hz, 3H) 4.75 (q, J=6.41 Hz, 1H) 7.47-7.56 (m, 4H) 7.77 (d, J=5.34 Hz, 1H) 8.47 (s, 1H) 8.67 (d, J=5.34 Hz, 1H).

Example 46

1-[3-(3,4-Dichloro-phenyl)-pyridin-4-yl]ethanol

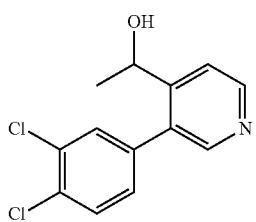

According to General Procedure, to a solution of 1-(3-bromo-pyridin-4-yl)-ethanol (20 mg, 99 μmol, 1 eq) in DMF (600 μl) were added Na$_2$CO$_3$ (21 mg, 198 μmol, 2 eq) and 3,4-dichlorophenylboronic acid (22.4 mg, 109 μmol, 1.1 eq). To the stirred mixture, PdCl$_2$(dppf).CH$_2$Cl$_2$ complex (1.6 mg, 2 μmol, 0.02 eq) was added.

The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (system B) and lyophilized to give 1-[3-(3,4-dichloro-phenyl)-pyridin-4-yl]-ethanol (11.5 mg, >95% purity, yield: 43%).

The isolated product was identified by LC-MS (system 1) and NMR (system 3): [M+H]$^+$=268, retention time=1.80 min, $^1$H NMR (500 MHz, DMSO-d$_6$) δ ppm 1.18 (d, J=6.56 Hz, 3H) 4.75 (q, J=6.51 Hz, 1H) 7.41 (dd, J=8.24, 1.98 Hz, 1H) 7.73 (d, J=1.98 Hz, 1H) 7.75-7.79 (m, 2H) 8.49 (s, 1H) 8.69 (d, J=5.34 Hz, 1H).

Example 47

1-[3-(4-Fluoro-3-methyl-phenyl)-pyridin-4-yl]-ethanol

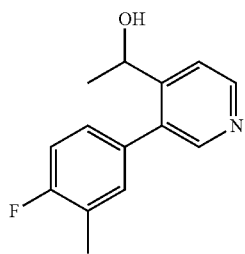 [SMILES: Cc1cc(-c2cnccc2C(C)O)ccc1F]

According to General Procedure, to a solution of 1-(3-bromo-pyridin-4-yl)-ethanol (20 mg, 99 μmol, 1 eq) in DMF (600 μl) were added Na$_2$CO$_3$ (21 mg, 198 μmol, 2 eq) and 4-fluoro-3-methylphenylboronic acid (22.4 mg, 109 μmol, 1.1 eq). To the stirred mixture, PdCl$_2$(dppf).CH$_2$Cl$_2$ complex (1.6 mg, 2 μmol, 0.02 eq) was added.

The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (system B) and lyophilized to give 1-[3-(4-fluoro-3-methyl-phenyl)-pyridin-4-yl]-ethanol (16.9 mg, >95% purity, yield: 74%).

The isolated product was identified by LC-MS (system 1) and NMR (system 3): [M+H]$^+$=232, retention time=1.34 min, $^1$H NMR (500 MHz, DMSO-d$_6$) δ ppm 1.17 (d, J=6.41 Hz, 3H) 2.29 (d, J=1.07 Hz, 3H) 4.79 (q, J=6.46 Hz, 1H) 7.22-7.28 (m, 2H) 7.32 (s, 1H) 7.76 (d, J=5.19 Hz, 1H) 8.43 (s, 1H) 8.64 (d, J=5.34 Hz, 1H).

Example 48

1-(3-Naphthalen-2-yl-pyridin-4-yl)-ethanol

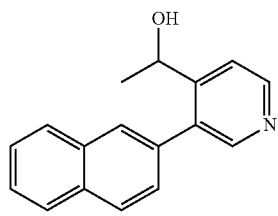

According to General Procedure, to a solution of 1-(3-bromo-pyridin-4-yl)-ethanol (20 mg, 99 μmol, 1 eq) in DMF (600 μl) were added $Na_2CO_3$ (21 mg, 198 μmol, 2 eq) and 2-naphthaleneboronic acid (22.4 mg, 109 μmol, 1.1 eq). To the stirred mixture, $PdCl_2(dppf) \cdot CH_2Cl_2$ complex (1.6 mg, 2 μmol, 0.02 eq) was added.

The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (system C) and lyophilized to give 1-(3-naphthalen-2-yl-pyridin-4-yl)-ethanol (8.5 mg, >95% purity, yield: 34%).

The isolated product was identified by LC-MS (system 1) and NMR (system 3): $[M+H]^+$=250, retention time=1.67 min, $^1$H NMR (500 MHz, DMSO-$d_6$) δ ppm 1.18 (d, J=6.41 Hz, 3H) 4.89 (q, J=6.41 Hz, 1H) 7.54 (dd, J=8.39, 1.68 Hz, 1H) 7.57-7.62 (m, 2H) 7.87 (d, J=5.34 Hz, 1H) 7.95 (s, 1H) 7.97-8.02 (m, 2H) 8.05 (d, J=8.39 Hz, 1H) 8.59 (s, 1H) 8.72 (d, J=5.49 Hz, 1H).

Example 49

1-[3-(4-Methylsulfanyl-phenyl)-pyridin-4-yl]ethanol

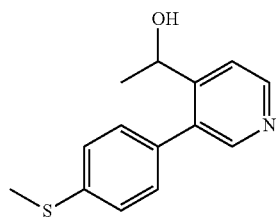

According to General Procedure, to a solution of 1-(3-bromo-pyridin-4-yl)-ethanol (20 mg, 99 μmol, 1 eq) in DMF (600 μl) were added $Na_2CO_3$ (21 mg, 198 μmol, 2 eq) and 4-(methylthio)phenylboronic acid (22.4 mg, 109 μmol, 1.1 eq). To the stirred mixture, $PdCl_2(dppf) \cdot CH_2Cl_2$ complex (1.6 mg, 2 μmol, 0.02 eq) was added.

The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (system C) and lyophilized to give 1-[3-(4-methylsulfanyl-phenyl)-pyridin-4-yl]-ethanol (6.8 mg, >95% purity, yield: 21%).

The isolated product was identified by LC-MS (system 1) and NMR (system 3): $[M+H]^+$=246, retention time=1.43 min, $^1$H NMR (500 MHz, DMSO-$d_6$) δ ppm 1.18 (d, J=6.41 Hz, 3H) 2.53 (s, 3H) 4.84 (q, J=6.41 Hz, 1H) 7.30-7.42 (m, 4H) 7.83 (d, J=5.49 Hz, 1H) 8.49 (s, 1H) 8.68 (d, J=5.49 Hz, 1H).

Example 50

1-[3-(3,4-Dimethyl-phenyl)-pyridin-4-yl]-ethanol

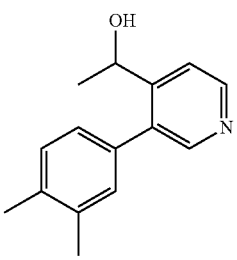

According to General Procedure, to a solution of 1-(3-bromo-pyridin-4-yl)-ethanol (20 mg, 99 μmol, 1 eq) in DMF (600 μl) were added $Na_2CO_3$ (21 mg, 198 μmol, 2 eq) and 3,4-dimethylphenylboronic acid (22.4 mg, 109 μmol, 1.1 eq). To the stirred mixture, $PdCl_2(dppf) \cdot CH_2Cl_2$ complex (1.6 mg, 2 μmol, 0.02 eq) was added.

The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (system C) and lyophilized to give 1-[3-(3,4-dimethyl-phenyl)-pyridin-4-yl]-ethanol (16 mg, >95% purity, yield: 71%).

The isolated product was identified by LC-MS (system 1) and NMR (system 3): $[M+H]^+$=228, retention time=1.52 min, $^1$H NMR (500 MHz, DMSO-$d_6$) δ ppm 1.16 (d, J=6.41 Hz, 3H) 2.28 (s, 6H) 4.85 (q, J=6.41 Hz, 1H) 7.10 (dd, J=7.55, 1.30 Hz, 1H) 7.16 (s, 1H) 7.27 (d, J=7.63 Hz, 1H) 7.82 (d, J=5.49 Hz, 1H) 8.46 (s, 1H) 8.67 (d, J=5.49 Hz, 1H).

Example 51

1-(3-Benzo[b]thiophen-2-yl-pyridin-4-yl)-ethanol

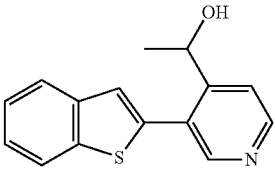

According to General Procedure, to a solution of 1-(3-bromo-pyridin-4-yl)-ethanol (20 mg, 99 μmol, 1 eq) in DMF (600 μl) were added $Na_2CO_3$ (21 mg, 198 μmol, 2 eq) and benzo[b]thiophene-2-boronic acid (22.4 mg, 109 μmol, 1.1 eq). To the stirred mixture, $PdCl_2(dppf) \cdot CH_2Cl_2$ complex (1.6 mg, 2 μmol, 0.02 eq) was added.

The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (system C) and lyophilized to give 1-(3-benzo[b]thiophen-2-yl-pyridin-4-yl)-ethanol (10 mg, >95% purity, yield: 40%).

The isolated product was identified by LC-MS (system 1) and NMR (system 3): [M+H]$^+$=256, retention time=1.86 min, $^1$H NMR (500 MHz, DMSO-d$_6$) δ ppm 1.29 (d, J=6.41 Hz, 3H) 5.10 (q, J=6.41 Hz, 1H) 7.40-7.47 (m, J=7.41, 7.41, 7.31, 7.10, 1.30 Hz, 2H) 7.57 (s, 1H) 7.75 (d, J=5.34 Hz, 1H) 7.91-7.94 (m, 1H) 8.02-8.05 (m, 1H) 8.63 (s, 1H) 8.67 (d, J=5.34 Hz, 1H).

Example 52

1-[3-(5-Chloro-thiophen-2-yl)-pyridin-4-yl]ethanol

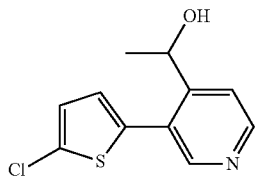

According to General Procedure, to a solution of 1-(3-bromo-pyridin-4-yl)-ethanol (20 mg, 99 µmol, 1 eq) in DMF (600 µl) were added Na$_2$CO$_3$ (21 mg, 198 µmol, 2 eq) and 5-chlorothiophene-2-boronic acid (22.4 mg, 109 µmol, 1.1 eq). To the stirred mixture, PdCl$_2$(dppf).CH$_2$Cl$_2$ complex (1.6 mg, 2 µmol, 0.02 eq) was added.

The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (system C) and lyophilized to give 1-[3-(5-chloro-thiophen-2-yl)-pyridin-4-yl]-ethanol (3.3 mg, >95% purity, yield: 14%). The isolated product was identified by LC-MS (system 2): [M+H]$^+$=240, retention time=1.38 min.

Example 53

1-[3-(5-Methyl-benzo[b]thiophen-2-yl)-pyridin-4-yl]-ethanol

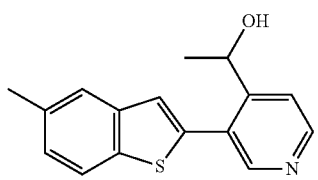

According to General Procedure, to a solution of 1-(3-bromo-pyridin-4-yl)ethanol (20 mg, 99 µmol, 1 eq) in DMF (600 µl) were added Na$_2$CO$_3$ (21 mg, 198 µmol, 2 eq) and 5-methyl-benzo[b]thiophene-2-boronic acid (22.4 mg, 109 µmol, 1.1 eq). To the stirred mixture, PdCl$_2$(dppf).CH$_2$Cl$_2$ complex (1.6 mg, 2 µmol, 0.02 eq) was added.

The reaction was carried out under sealed-vessel microwave heating at 150° C. for 20 minutes using a Biotage Initiator™ (pre-stirring: 10 s, absorption level: high). Upon completion of the reaction, the mixture was allowed to cool to room temperature, the Pd catalyst was filtered off and the solvent was removed. The crude product obtained was purified by preparative LC-MS (system D) and lyophilized to give 1-[3-(5-methyl-benzo[b]thiophen-2-yl)-pyridin-4-yl]-ethanol (3.5 mg, >95% purity, yield: 13%).

The isolated product was identified by LC-MS (system 1) and NMR (system 4): [M+H]$^+$=270, retention time=2.16 min, $^1$H NMR (400 MHz, DMSO-d$_6$) δ ppm 1.28 (d, J=6.32 Hz, 3H) 2.43 (s, 3H) 5.07 (q, J=6.36 Hz, 1H) 7.23 (d, J=8.21 Hz, 1H) 7.45 (s, 1H) 7.68-7.72 (m, 2H) 7.87 (d, J=8.21 Hz, 1H) 8.58 (s, 1H) 8.62 (d, J=5.18 Hz, 1H).

It can be seen that the compounds of this invention are useful as inhibitors of aldosterone synthase activity and therefore useful in the treatment of diseases and conditions mediated by aldosterone synthase such as the metabolic disorders disclosed herein.

It will be understood that the invention has been described by way of example only and modifications may be made whilst remaining within the scope and spirit of the invention.

What is claimed is:

1. A compound of Formula I:

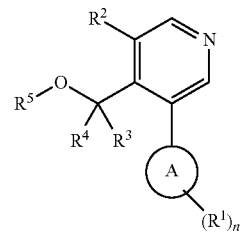

wherein:
A is phenyl, naphthyl or a heteroaryl selected from the group consisting of benzimidazolyl, azaindolyl, quinolinyl, benzothienyl, benzoxazolyl, thienyl, benzothiazolyl and benzofuranyl;

R$^1$ for each occurrence, is independently halogen, C$_{1-6}$-alkyl, C$_{3-7}$-cycloalkyl, C$_{1-6}$-alkoxy, —S—C$_{1-6}$-alkyl, S—C$_{6-10}$-aryl, C$_{6-10}$-aryl, C$_{6-10}$-aryl-C$_{1-6}$-alkyloxy, heteroaryl, heterocyclyl, C$_{6-10}$aryloxy, heteroaryloxy, heterocyclyloxy, cyano, NR$^a$R$^b$, nitro, C(O)—C$_{1-6}$-alkyl, C(O)O—C$_{1-6}$-alkyl, C(O)O—C$_{6-10}$aryl, C(O)O-heteroaryl, C(O)NR$^a$R$^b$, NR$^a$C(O)—C$_{1-6}$-alkyl, NR$^a$C(O)—C$_{6-10}$aryl, NR$^a$C(O)-heteroaryl, NR$^a$-heterocyclyl, carboxy, sulfonyl, sulfamoyl or sulfonamido, in which each alkyl, alkoxy, aryl, heteroaryl and heterocyclyl are optionally substituted with one or more groups selected from the group consisting of halo, C$_{1-6}$-alkyl, C$_{1-6}$-alkoxy, hydroxy, halo-C$_{1-6}$-alkyl, C$_{6-10}$-aryl, heteroaryl, C$_{6-10}$-aryloxy and C$_{3-7}$cycloalkyl; or two adjacent R$^1$ form together with the atoms to which they are attached a 5- or 6-membered saturated heterocyclyl; with the proviso that two adjacent R$^1$ do not form together with A ring an indolinone, a benzoxazolone, a benzimidazolone or a benzothiazolone;

$R^a$ and $R^b$ for each occurrence, are independently H, $C_{1-6}$-alkyl, $C_{3-7}$-cycloalkyl, $C_{6-10}$-aryl, heterocyclyl, heteroaryl or $R^a$ and $R^b$ which are attached to the same nitrogen may form together with the nitrogen to which they are attached a 5- to 7-membered saturated heterocyclyl;

$R^2$ is H, $C_{1-6}$-alkyl, $C_{1-6}$-alkoxy, halo-$C_{1-6}$-alkyl, $C_{3-7}$-cycloalkyl, cyano, or halogen;

$R^3$ and $R^4$ are independently H, $C_{1-6}$-alkyl or $C_{3-7}$-cycloalkyl; wherein alkyl can be optionally substituted with $C_{1-6}$alkoxy, halogen, hydroxy, or $R^3$ and $R^4$ can form together with the atoms to which they are attached a 4- to 7-membered heterocyclyl or a 3- to 7-membered cycloalkyl; and when A is naphthyl or benzothiazolyl then one of $R^3$, $R^4$ is other than H;

$R^5$ is H or $C_{1-6}$-alkyl; or $R^5$ and $R^3$ or $R^5$ and $R^4$ form together with the atoms to which they are attached a 4- to 7-membered saturated heterocyclyl; or $R^5$ and $R^2$ form together with the atoms to which they are attached a 5- to 7-membered ring saturated heterocyclyl which may be optionally substituted with oxo;

n is 0, 1, 2, 3, 4 or 5;

with the proviso that compound of Formula I is not (3-o-tolylpyridin-4-yl)methanol; (3-methoxy-5-phenylpyridin-4-yl)methanol, (3-(2-fluorophenyl)-5-methoxypyridin-4-yl)methanol, (3-(4-fluorophenyl)-5-methoxypyridin-4-yl)methanol, (3-fluoro-5-(4-fluorophenyl)pyridin-4-yl)methanol, (3-(4-fluorophenyl)pyridin-4-yl)methanol, (3-fluoro-5-phenylpyridin-4-yl)methanol, (3-chloro-5-phenylpyridin-yl)methanol, (3-chloro-5-(2-fluorophenyl)pyridin-4-yl)methanol, (3-fluoro-5-(2-fluorophenyl)pyridin-4-yl)methanol, (3-(2-fluorophenyl)pyridin-4-yl)methanol, (3-phenylpyridin-4-yl)methanol, (3-chloro-5-(4-fluorophenyl)pyridin-4-yl)methanol, (3-chloro-5-(3-fluorophenyl)pyridin-4-yl)methanol, (3-fluoro-5-(3-fluorophenyl)pyridin-4-yl)methanol, (3-(3-fluorophenyl)-5-methoxypyridin-4-yl)methanol or (3-(3-fluorophenyl)pyridin-4-yl)methanol, or a pharmaceutically acceptable salt thereof.

2. The compound according to claim 1 wherein:

A is phenyl, naphthyl or benzofuranyl;

$R^1$ for each occurrence, is independently halogen, $C_{1-6}$-alkyl, $C_{3-7}$-cycloalkyl, $C_{1-6}$-alkoxy, S—$C_{1-6}$-alkyl, —S—$C_{6-10}$-aryl, $C_{6-10}$-aryl, $C_{6-10}$-aryl-$C_{1-6}$-alkyloxy, heteroaryl, heterocyclyl, $C_{6-10}$aryloxy, heteroaryloxy, heterocyclyloxy, cyano, $NR^aR^b$, nitro, C(O)—$C_{1-6}$-alkyl, C(O)O—$C_{1-6}$-alkyl, C(O)O—$C_{6-10}$aryl, C(O)O-heteroaryl, C(O)$NR^aR^b$, $NR^aC(O)$—$C_{1-6}$-alkyl, $NR^aC(O)$—$C_{6-10}$-aryl, $NR^aC(O)$-heteroaryl, $NR^a$-heterocyclyl, carboxy, sulfonyl, sulfamoyl or sulfonamido, in which each alkyl, alkoxy, aryl, heteroaryl and heterocyclyl are optionally substituted with halo, $C_{1-6}$-alkyl, $C_{1-6}$-alkoxy, hydroxy, halo-$C_{1-6}$-alkyl, $C_{6-10}$-aryl, heteroaryl, $C_{6-10}$-aryloxy or $C_{3-7}$cycloalkyl;

$R^a$ and $R^b$ for each occurrence, are independently H, $C_{1-6}$-alkyl, $C_{3-7}$-cycloalkyl, $C_{6-10}$-aryl, heterocyclyl, heteroaryl or $R^a$ and $R^b$ which are attached to the same nitrogen may form together with the nitrogen to which they are attached a 5- to 7-membered saturated heterocyclyl;

$R^2$ is H, $C_{1-6}$-alkyl, $C_{1-6}$-alkoxy, halo-$C_{1-6}$-alkyl or halogen;

$R^3$ and $R^4$ are independently H, $C_{1-6}$-alkyl or $C_{3-7}$-cycloalkyl; wherein alkyl can be optionally substituted with $C_{1-6}$alkoxy, halogen, hydroxy, or $R^3$ and $R^4$ can form together with the atoms to which they are attached a 4- to 7-membered heterocyclyl or a 3- to 7-membered cycloalkyl; and when A is naphthyl then one of $R^3$, $R^4$ is other than H;

$R^5$ is H or $C_{1-6}$-alkyl; or $R^5$ and $R^3$ or $R^5$ and $R^4$ form together with the atoms to which they are attached a 4- to 7-membered saturated heterocyclyl; or $R^5$ and $R^2$ form together with the atoms to which they are attached a 5- to 7-membered ring saturated heterocyclyl which may be optionally substituted with oxo;

n is 0, 1, 2, 3, 4 or 5;

with the proviso that compound of Formula I is not (3-o-tolylpyridin-4-yl)methanol; (3-methoxy-5-phenylpyridin-4-yl)methanol, (3-(2-fluorophenyl)-5-methoxypyridin-4-yl)methanol, (3-(4-fluorophenyl)-5-methoxypyridin-4-yl)methanol, (3-fluoro-5-(4-fluorophenyl)pyridin-4-yl)methanol, (3-(4-fluorophenyl)pyridin-4-yl)methanol, (3-fluoro-5-phenylpyridin-4-yl)methanol, (3-chloro-5-phenylpyridin-yl)methanol, (3-chloro-5-(2-fluorophenyl)pyridin-4-yl)methanol, (3-fluoro-5-(2-fluorophenyl)pyridin-4-yl)methanol, (3-(2-fluorophenyl)pyridin-4-yl)methanol, (3-phenylpyridin-4-yl)methanol, (3-chloro-5-(4-fluorophenyl)pyridin-4-yl)methanol, (3-chloro-5-(3-fluorophenyl)pyridin-4-yl)methanol, (3-fluoro-5-(3-fluorophenyl)pyridin-4-yl)methanol, (3-(3-fluorophenyl)-5-methoxypyridin-4-yl)methanol or (3-(3-fluorophenyl)pyridin-4-yl)methanol; or a pharmaceutically acceptable salt thereof.

3. The compound according to claim 1 of Formula II:

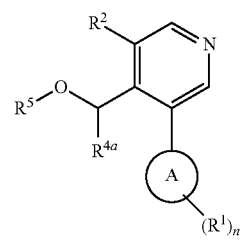

II wherein:

$R^1$ for each occurrence, is independently halogen, $C_{1-6}$-alkyl, $C_{3-7}$-cycloalkyl, $C_{1-6}$-alkoxy, S—$C_{1-6}$-alkyl, —S—$C_{6-10}$-aryl, $C_{6-10}$-aryl, $C_{6-10}$-aryl-$C_{1-6}$-alkyloxy, heteroaryl, heterocyclyl, $C_{6-10}$aryloxy, heteroaryloxy, heterocyclyloxy, cyano, $NR^aR^b$, nitro, C(O)—$C_{1-6}$-alkyl, C(O)O—$C_{1-6}$-alkyl, C(O)O—$C_{6-10}$aryl, C(O)O-heteroaryl, C(O)$NR^aR^b$, $NR^aC(O)$—$C_{1-6}$-alkyl, $NR^aC(O)$—$C_{6-10}$-aryl, $NR^aC(O)$-heteroaryl, $NR^a$-heterocyclyl, carboxy, sulfonyl, sulfamoyl or sulfonamido, in which each alkyl, alkoxy, aryl, heteroaryl and heterocyclyl are optionally substituted with halo, $C_{1-6}$-alkyl, $C_{1-6}$-alkoxy, hydroxy, halo-$C_{1-6}$-alkyl, $C_{6-10}$-aryl, heteroaryl, $C_{6-10}$-aryloxy or $C_{3-7}$cycloalkyl;

$R^a$ and $R^b$ for each occurrence, are independently H, $C_{3-7}$-cycloalkyl, $C_{6-10}$-aryl, heterocyclyl, heteroaryl or $R^a$ and $R^b$ which are attached to the same nitrogen, may form together with the nitrogen to which they are attached a 5- to 7-membered saturated heterocyclyl;

$R^2$ is H, $C_{1-6}$-alkyl, $C_{1-6}$-alkoxy, halo-$C_{1-6}$-alkyl or halogen;

$R^{4a}$ is $C_{1-6}$-alkyl or $C_{3-7}$cycloalkyl; wherein alkyl can be optionally substituted with alkoxy, halogen, hydroxy;

$R^5$ is H or $C_{1-6}$-alkyl; or or $R^5$ and $R^{4a}$ form together with the atoms to which they are attached a 4- to 7-membered saturated heterocyclyl;

n is 0, 1, 2, 3, 4 or 5;

or a pharmaceutically acceptable salt thereof.

4. The compound according to claim 1 having Formula III:

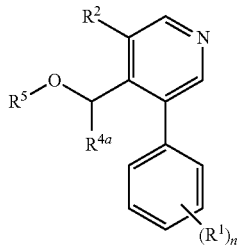

wherein:
- $R^1$ for each occurrence, is independently halogen, $C_{1-6}$-alkyl, $C_{3-7}$-cycloalkyl, $C_{1-6}$-alkoxy, S—$C_{1-6}$-alkyl, —S—$C_{6-10}$-aryl, $C_{6-10}$-aryl, $C_{6-10}$-aryl-$C_{1-6}$-alkyloxy, heteroaryl, heterocyclyl, $C_{6-10}$aryloxy, heteroaryloxy, heterocyclyloxy, cyano, $NR^aR^b$, nitro, C(O)—$C_{1-6}$-alkyl, C(O)O—$C_{1-6}$-alkyl, C(O)O—$C_{6-10}$aryl, C(O)O-heteroaryl, C(O)$NR^aR^b$, $NR^aC(O)$—$C_{1-6}$-alkyl, $NR^aC(O)$—$C_{6-10}$-aryl, $NR^aC(O)$-heteroaryl, $NR^a$-heterocyclyl, carboxy, sulfonyl, sulfamoyl or sulfonamido, in which each alkyl, alkoxy, aryl, heteroaryl and heterocyclyl are optionally substituted with halo, $C_{1-6}$-alkyl, $C_{1-6}$-alkoxy, hydroxy, halo-$C_{1-6}$-alkyl, $C_{6-10}$-aryl, heteroaryl, $C_{6-10}$-aryloxy or $C_{3-7}$cycloalkyl;
- $R^a$ and $R^b$ for each occurrence, are independently H, $C_{1-6}$-alkyl, $C_{3-7}$-cycloalkyl, $C_{6-10}$-aryl, heterocyclyl, heteroaryl or $R^a$ and $R^b$ which are attached to the same nitrogen, may form together with the nitrogen to which they are attached a 5- to 7-membered saturated heterocyclyl;
- $R^2$ is H, $C_{1-6}$-alkyl, $C_{1-6}$-alkoxy, halo-$C_{1-6}$-alkyl or halogen;
- $R^{4a}$ is H, $C_{1-6}$-alkyl or $C_{3-7}$cycloalkyl; wherein alkyl can be optionally substituted with alkoxy, halogen, hydroxy;
- $R^5$ is H or $C_{1-6}$-alkyl; or $R^5$ and $R^{4a}$ form together with the atoms to which they are attached a 4- to 7-membered ring saturated heterocyclyl;
- n is 0, 1, 2, 3, 4 or 5;

or a pharmaceutically acceptable salt thereof.

5. The compound according to claim 1 having Formula IV:

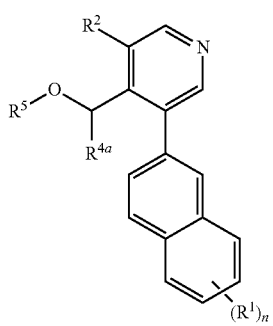

$R^1$ for each occurrence, is independently halogen, $C_{1-6}$-alkyl, $C_{3-7}$-cycloalkyl, $C_{1-6}$-alkoxy, —S—$C_{1-6}$-alkyl, S—$C_{6-10}$-aryl, $C_{6-10}$-aryl, $C_{6-10}$-aryl-$C_{1-6}$-alkyloxy, heteroaryl, heterocyclyl, $C_{6-10}$aryloxy, heteroaryloxy, heterocyclyloxy, cyano, $NR^aR^b$, nitro, C(O)—$C_{1-6}$-alkyl, C(O)O—$C_{1-6}$-alkyl, C(O)O—$C_{6-10}$aryl, C(O)O-heteroaryl, C(O)$NR^aR^b$, $NR^aC(O)$—$C_{1-6}$-alkyl, $NR^aC(O)$—$C_{6-10}$-aryl, $NR^aC(O)$-heteroaryl, $NR^a$-heterocyclyl, carboxy, sulfonyl, sulfamoyl or sulfonamido, in which each alkyl, alkoxy, aryl, heteroaryl and heterocyclyl are optionally substituted with halo, $C_{1-6}$-alkyl, $C_{1-6}$-alkoxy, hydroxy, halo-$C_{1-6}$-alkyl, $C_{6-10}$-aryl, heteroaryl, $C_{6-10}$-aryloxy or $C_{3-7}$cycloalkyl;

$R^a$ and $R^b$ for each occurrence, are independently H, $C_{1-6}$-alkyl, $C_{3-7}$-cycloalkyl, $C_{6-10}$-aryl, heterocyclyl, heteroaryl or $R^a$ and $R^b$ which are attached to the same nitrogen, may form together with the nitrogen to which they are attached a 5- to 7-membered saturated heterocyclyl;

$R^2$ is H, $C_{1-6}$-alkyl, $C_{1-6}$-alkoxy, halo-$C_{1-6}$-alkyl or halogen;

$R^{4a}$ is H, $C_{1-6}$-alkyl or $C_{3-7}$cycloalkyl; wherein alkyl can be optionally substituted with alkoxy, halogen, hydroxy;

$R^5$ is H or $C_{1-6}$-alkyl; or $R^5$ and $R^{4a}$ form together with the atoms to which they are attached a 4- to 7-membered ring saturated heterocyclyl;

n is 0, 1, 2, 3, 4 or 5;

or a pharmaceutically acceptable salt thereof.

6. The compound according to claim 1 having Formula V:

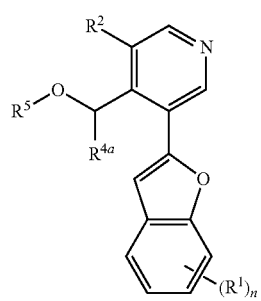

$R^1$ for each occurrence, is independently halogen, $C_{1-6}$-alkyl, $C_{3-7}$-cycloalkyl, $C_{1-6}$-alkoxy, S—$C_{1-6}$-alkyl, S—$C_{6-10}$-aryl, $C_{6-10}$-aryl, $C_{6-10}$-aryl-$C_{1-6}$-alkyloxy, heteroaryl, heterocyclyl, $C_{6-10}$aryloxy, heteroaryloxy, heterocyclyloxy, cyano, $NR^aR^b$, nitro, C(O)—$C_{1-6}$-alkyl, C(O)O—$C_{1-6}$-alkyl, C(O)O—$C_{6-10}$aryl, C(O)O-heteroaryl, C(O)$NR^aR^b$, $NR^aC(O)$—$C_{1-6}$-alkyl, $NR^aC(O)$—$C_{6-10}$-aryl, $NR^aC(O)$-heteroaryl, $NR^a$-heterocyclyl, carboxy, sulfonyl, sulfamoyl or sulfonamido, in which each alkyl, alkoxy, aryl, heteroaryl and heterocyclyl are optionally substituted with halo, $C_{1-6}$-alkyl, $C_{1-6}$-alkoxy, hydroxy, halo-$C_{1-6}$-alkyl, $C_{6-10}$-aryl, heteroaryl, $C_{6-10}$-aryloxy or $C_{3-7}$cycloalkyl;

$R^a$ and $R^b$ for each occurrence, are independently H, $C_{1-6}$-alkyl, $C_{3-7}$-cycloalkyl, $C_{6-10}$-aryl, heterocyclyl, heteroaryl or $R^a$ and $R^b$ which are attached to the same nitrogen may form together with the nitrogen to which they are attached a 5- to 7-membered saturated heterocyclyl;

$R^2$ is H, $C_{1-6}$-alkyl, $C_{1-6}$-alkoxy, halo-$C_{1-6}$-alkyl or halogen;

$R^{4a}$ is H, $C_{1-6}$-alkyl or $C_{3-7}$cycloalkyl; wherein alkyl can be optionally substituted with alkoxy, halogen, hydroxy;

$R^5$ is H or $C_{1-6}$-alkyl; or $R^5$ and $R^{4a}$ form together with the atoms to which they are attached a 4- to 7-membered ring saturated heterocyclyl;

n is 0, 1, 2, 3, 4 or 5.

or a pharmaceutically acceptable salt thereof.

7. The compound of claim 1 wherein $R^2$ is H or halo, or a pharmaceutically acceptable salt thereof.

8. The compound of claim 1 wherein $R^5$ is H, or a pharmaceutically acceptable salt thereof.

9. The compound of claim 1 wherein $R^4$ is methyl, or a pharmaceutically acceptable salt thereof.

10. The compound of claim 1 wherein n is 1 or 2 and each $R^1$ is independently halo, $C_{1-6}$-alkyl, cyano, —S—$C_{1-6}$-alkyl, $C_{1-6}$-alkoxy, halo-$C_{1-6}$-alkyl, halo-$C_{1-6}$-alkoxy, $C_{1-6}$-alkoxy-$C_{1-6}$-alkoxy, s-alkyl, di-$C_{1-6}$-alkylamino, $C_{1-6}$-alkylamino or heterocyclyl, or a pharmaceutically acceptable salt thereof.

11. A pharmaceutical composition comprising a therapeutically effective amount of a compound according to claim 1, or a pharmaceutically acceptable salt thereof, and one or more pharmaceutically acceptable carriers.

12. A combination comprising a therapeutically effective amount of the compound according to claim 1, or a pharmaceutically acceptable salt thereof, and one or more therapeutically active agents selected from an HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker, or a CETP inhibitor.

13. A method of treating a disorder or a disease in a subject mediated by aldosterone synthase wherein the method comprises administering to the subject a therapeutically effective amount of the compound according to claim 1, or a pharmaceutically acceptable salt thereof wherein disease or disorder is hypertension.

* * * * *